(12) United States Patent
Rothenhaeusler et al.

(10) Patent No.: US 10,246,460 B2
(45) Date of Patent: Apr. 2, 2019

(54) SYNTHESIS OF TRANS-8-CHLORO-5-METHYL-1-[4-(PYRIDIN-2-YLOXY)-CYCLOHEXYL]-5,6-DIHYDRO-4H-2,3,5,10B-TETRAAZA-BENZO[E]AZULENE AND CRYTALLINE FORMS THEREOF

(71) Applicant: Hoffmann-La Roche Inc., Little Falls, NJ (US)

(72) Inventors: Benno Rothenhaeusler, Loerrach (DE); Rene Trussardi, Birsfelden (CH); Fabienne Hoffmann-Emery, Weil am Rhein (DE); Urs Schwitter, Reinach (CH); Jean-Michel Adam, Village-Neuf (FR); Olaf Grassmann, Loerrach (DE); Thomas Hartung, Loerrach (DE); Frederic Ran, Kembs (FR); Ralph Diodone, Breisach (DE); Christophe Pfleger, Mulhouse (FR); Bjorn Bartels, Schopfheim (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/172,542

(22) Filed: Jun. 3, 2016

(65) Prior Publication Data

US 2016/0280712 A1 Sep. 29, 2016

Related U.S. Application Data

(63) Continuation of application No. PCT/EP2014/076041, filed on Dec. 1, 2014.

(30) Foreign Application Priority Data

Dec. 5, 2013 (EP) .................................. 13195864

(51) Int. Cl.
*C07D 487/04* (2006.01)
*C07D 243/14* (2006.01)

(52) U.S. Cl.
CPC ......... *C07D 487/04* (2013.01); *C07D 243/14* (2013.01); *C07B 2200/13* (2013.01)

(58) Field of Classification Search
CPC ........................... C07D 487/04; C07D 243/14
See application file for complete search history.

(56) References Cited

FOREIGN PATENT DOCUMENTS

| CA | 1197242 | 11/1985 |
|---|---|---|
| WO | 2004/074291 | 9/2004 |
| WO | 2005/068466 | 7/2005 |
| WO | 2007/002308 | 1/2007 |
| WO | 2010060836 A1 | 3/2010 |
| WO | 2011/131596 | 10/2011 |
| WO | 2015/024819 | 2/2015 |

OTHER PUBLICATIONS

Guillory, J. K. Polymorphis in Pharmaceutical Solids "Generation of Polymorphs, Hydrates, Solvates, and Amorphous Solids" Harry G. Brittain, New York:Marcel Dekker, Inc., vol. 95:183-225 ( 1999).
Written Opinion of the International Searching Authority for International Patent Application No. PC/EP2014/076041.
Beal et al., "Preparation of triazolobenzodiazepine derivatives as Vasopressin Vla antagonists" Tetrahedron Letters 52:5913-5917 (2011).
Frank et al., "Cyclizations of Substituted Benzylidene-3-alkenylamines: Synthesis of the Tricyclic Core of the Martinellines" J. Org Chem 65:655-666 (2000).

Primary Examiner — Alexander R Pagano
Assistant Examiner — Ebenezer O Sackey
(74) Attorney, Agent, or Firm — Robert C. Hall

(57) ABSTRACT

The present invention provides processes to manufacture substituted 1-[4-(Pyridin-2-yloxy)-cyclohexyl]-5,6-dihydro-4H-2,3,5,10b-tetraaza-benzo[e]azulenes. Also disclosed are compounds useful as intermediates in the methods of the invention.

6 Claims, 23 Drawing Sheets

Figure 1: XRPD pattern of Form A
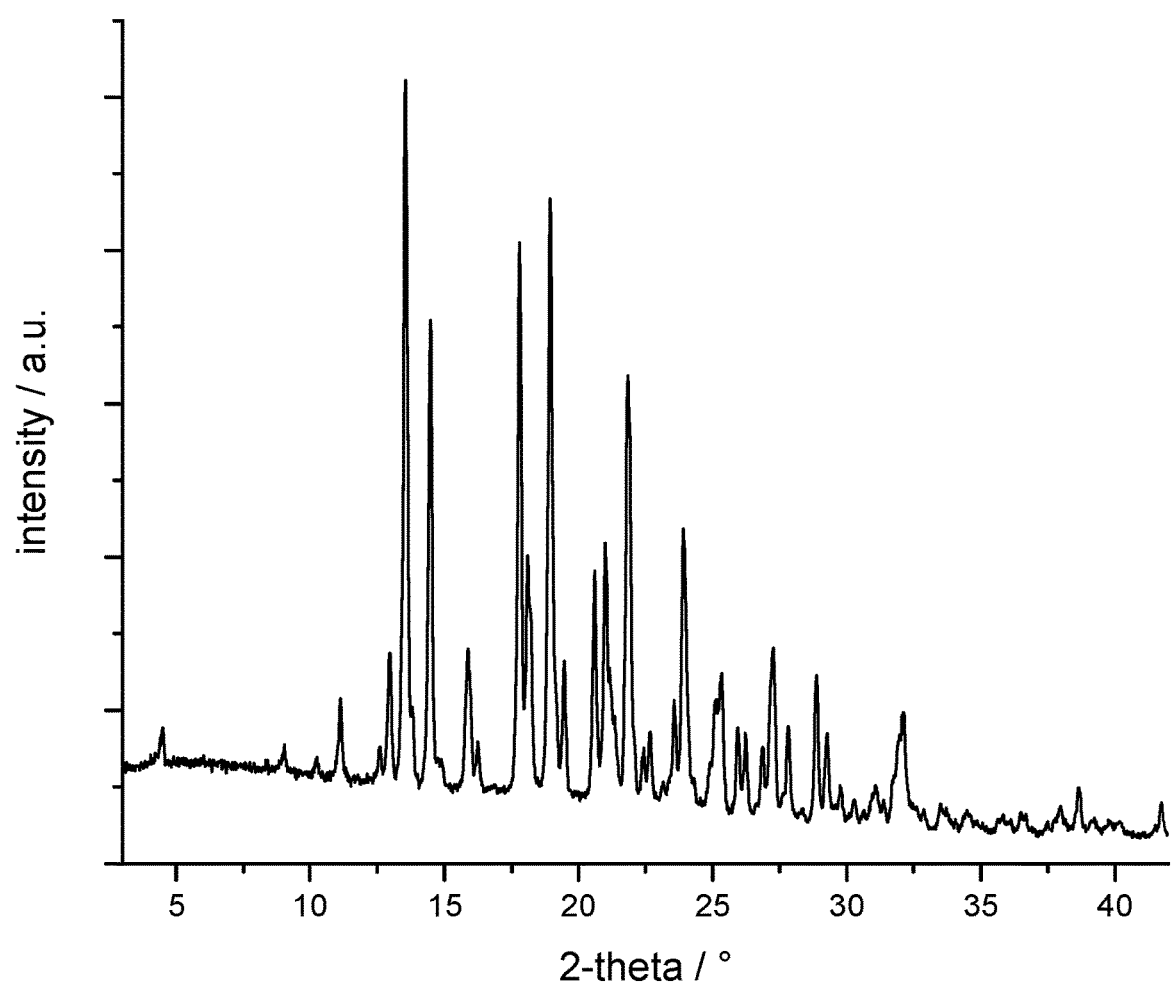

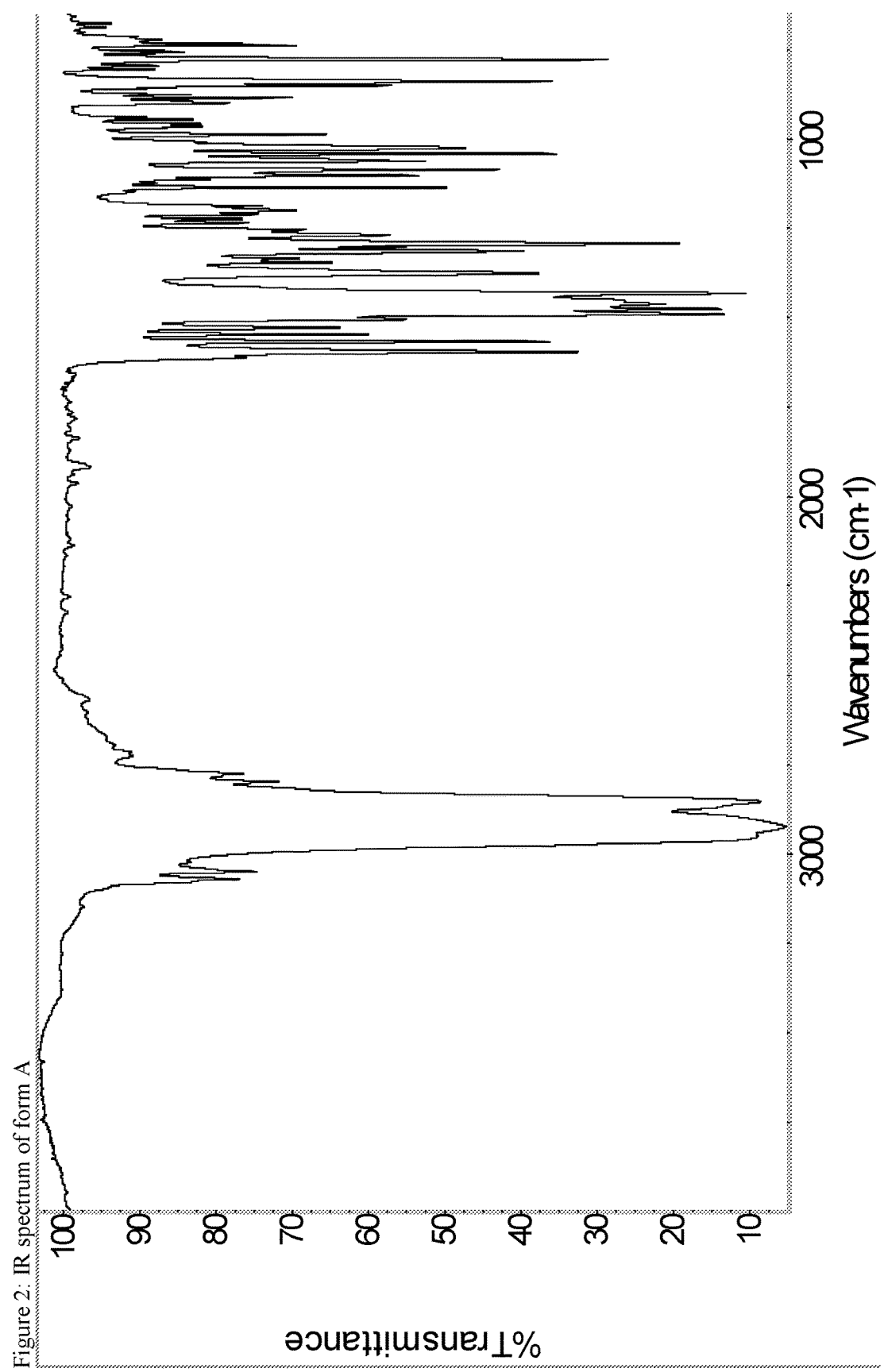
Figure 2: IR spectrum of form A

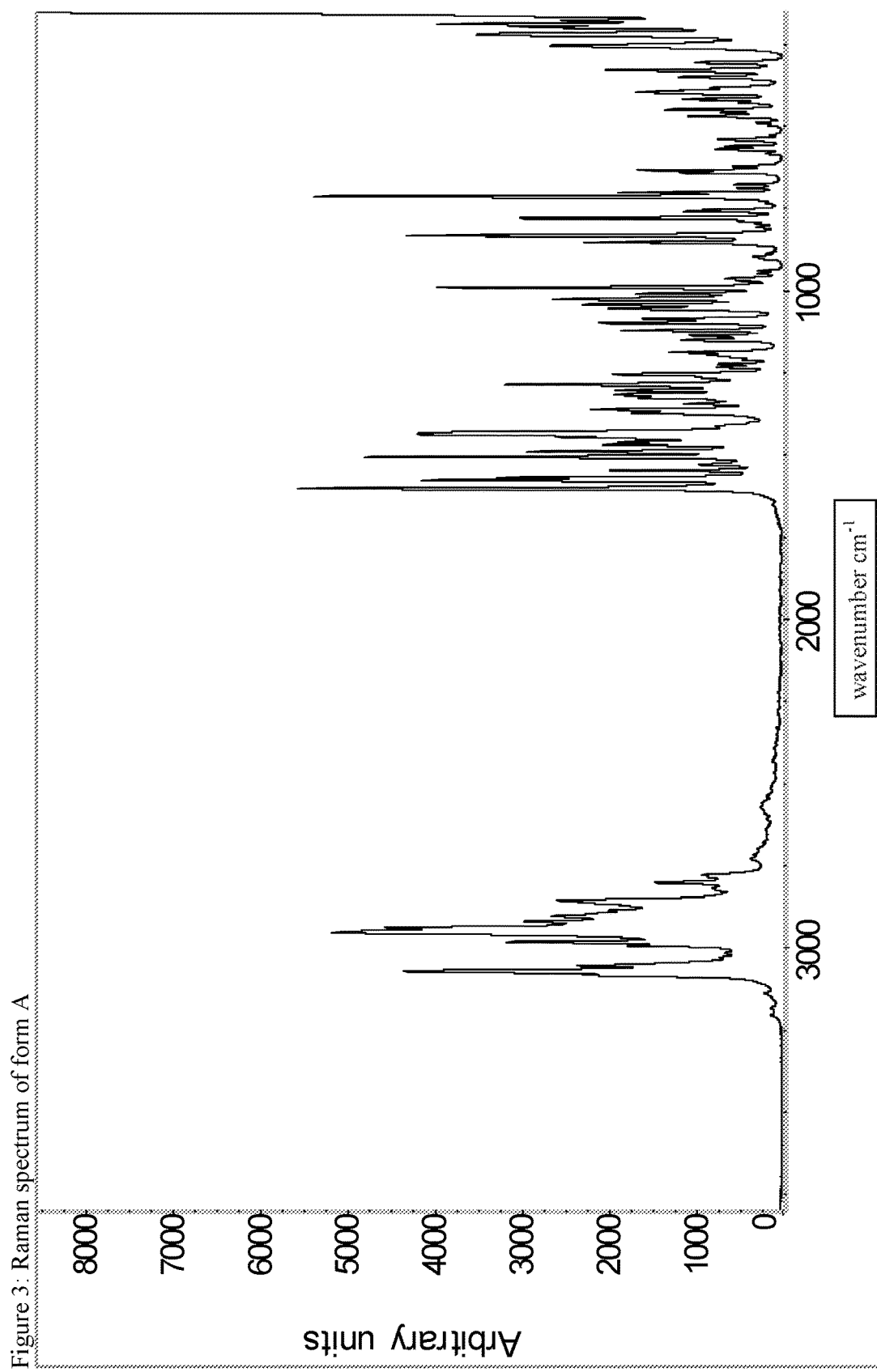
Figure 3: Raman spectrum of form A

Figure 4: XRPD pattern of Form B
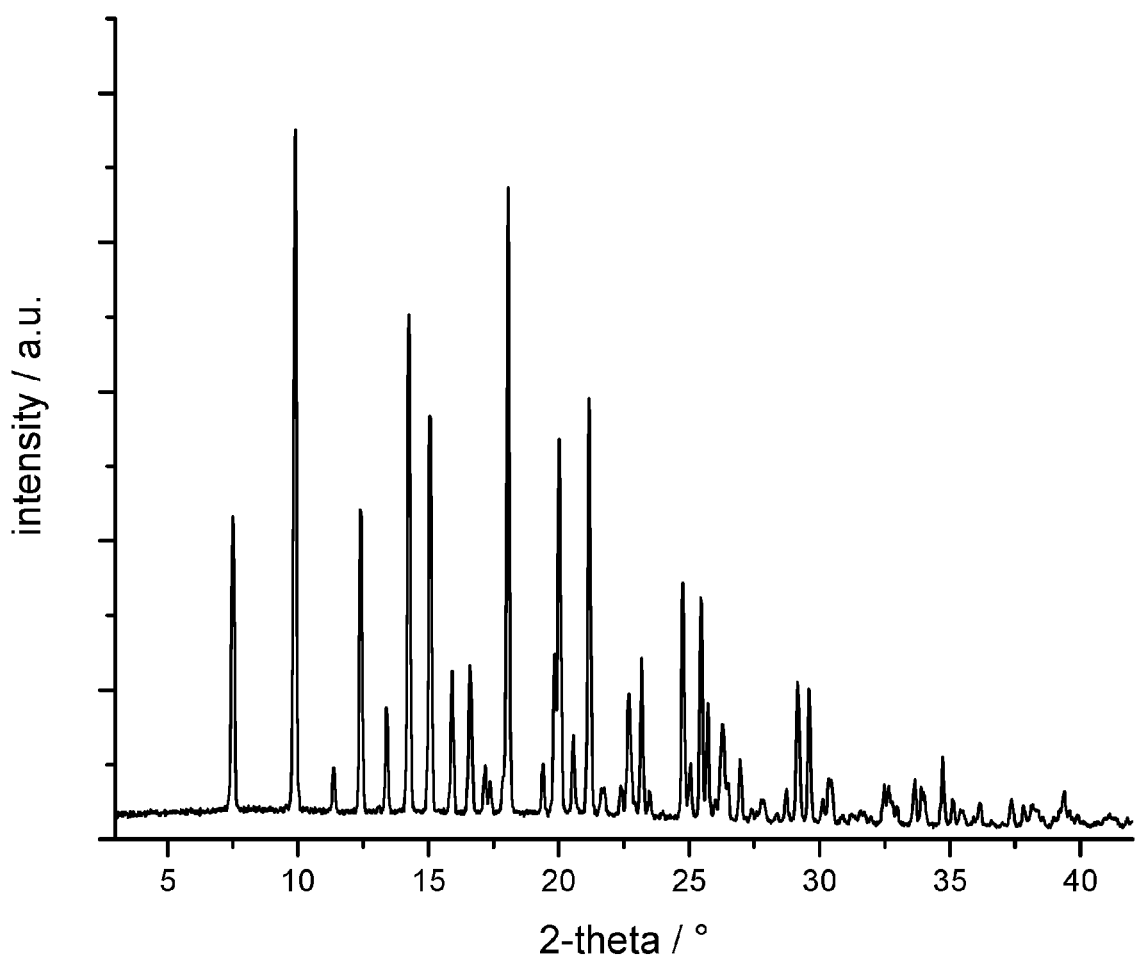

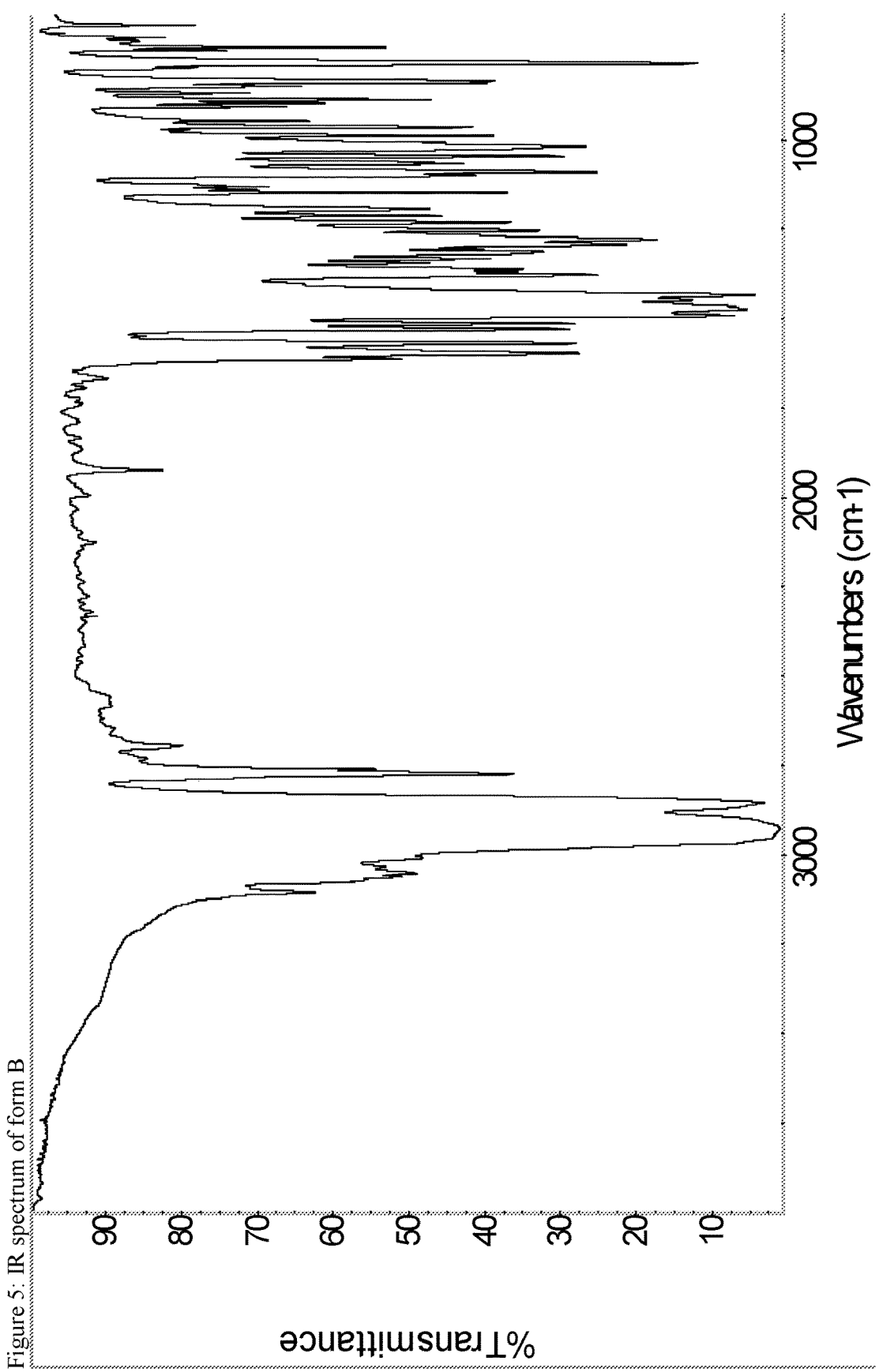
Figure 5: IR spectrum of form B

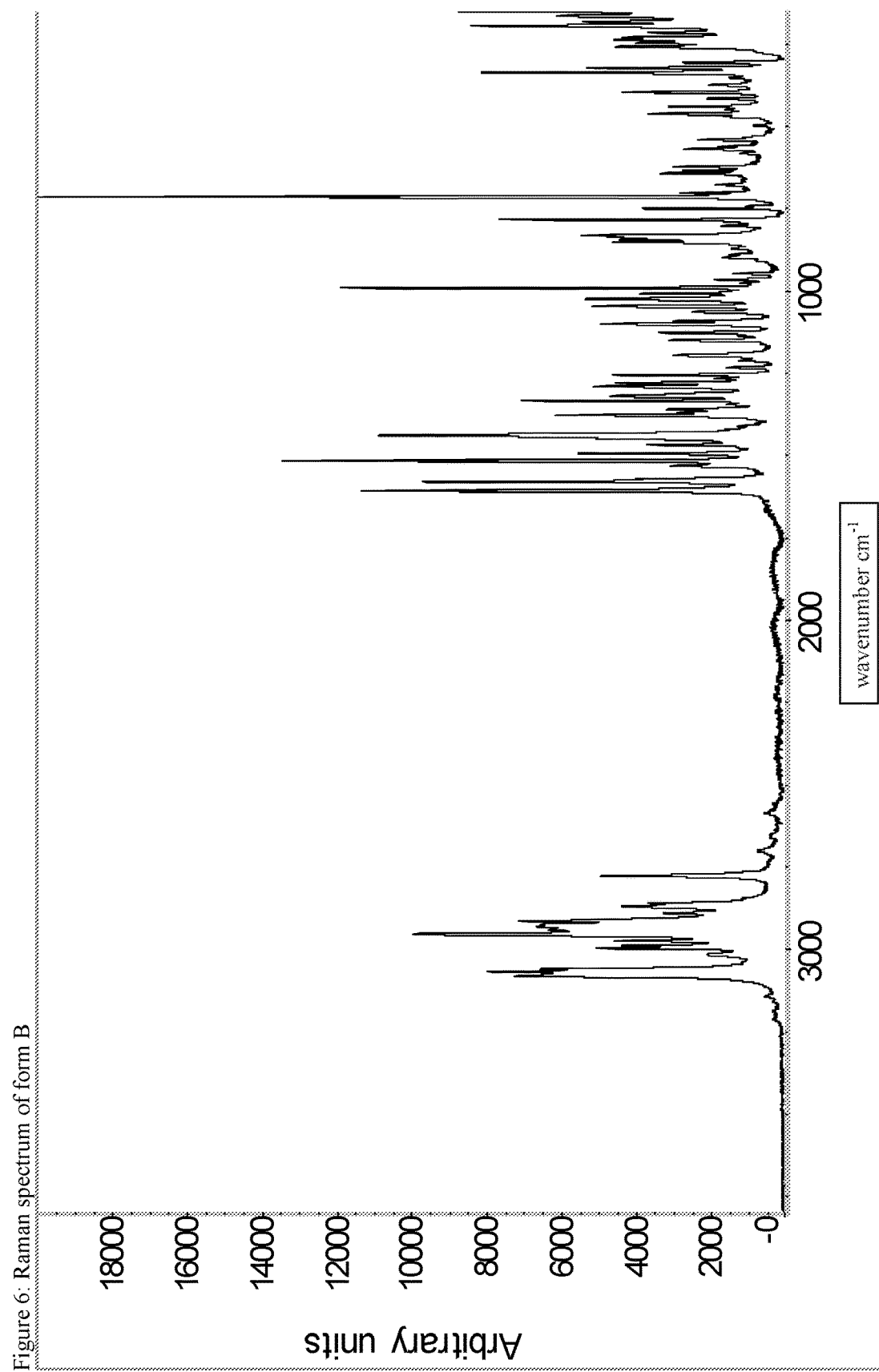
Figure 6: Raman spectrum of form B

Figure 7: XRPD pattern of Form C
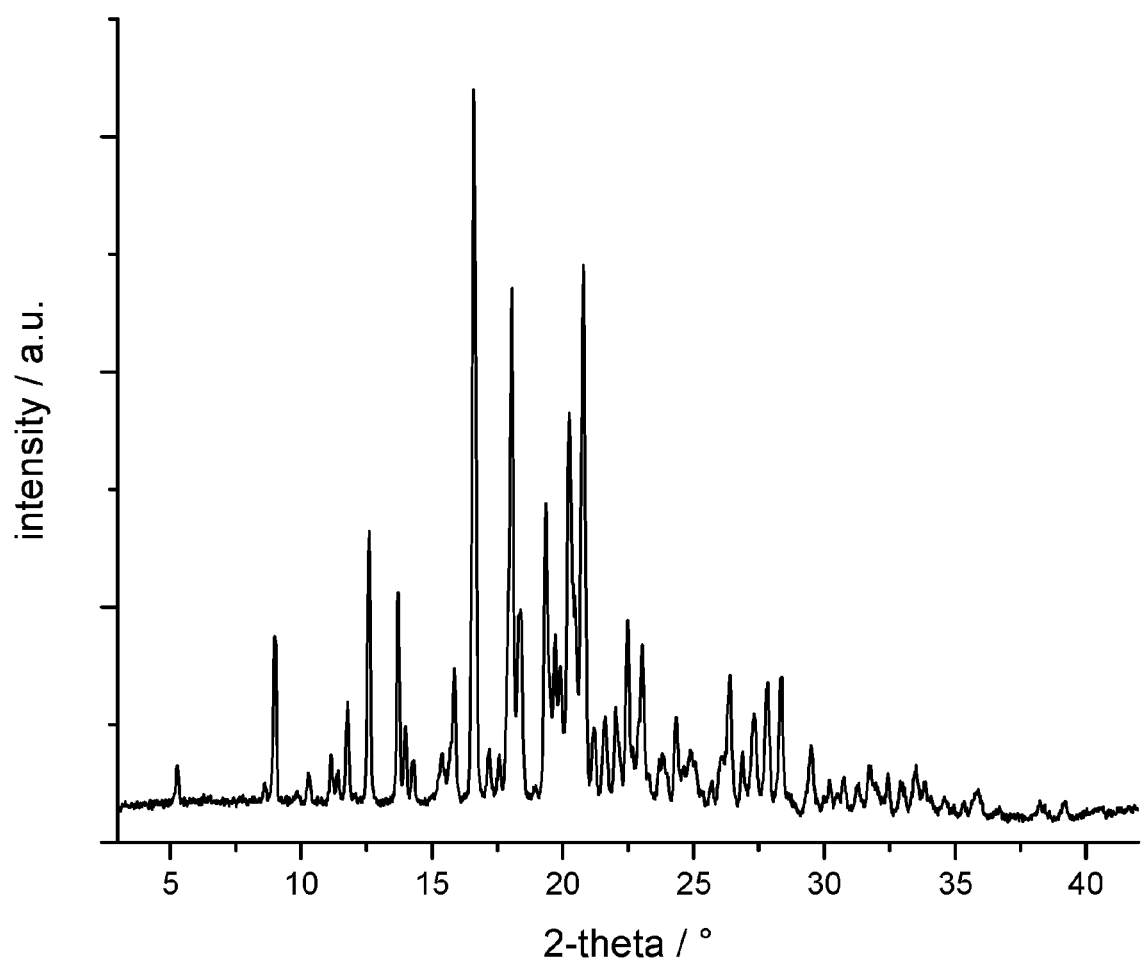

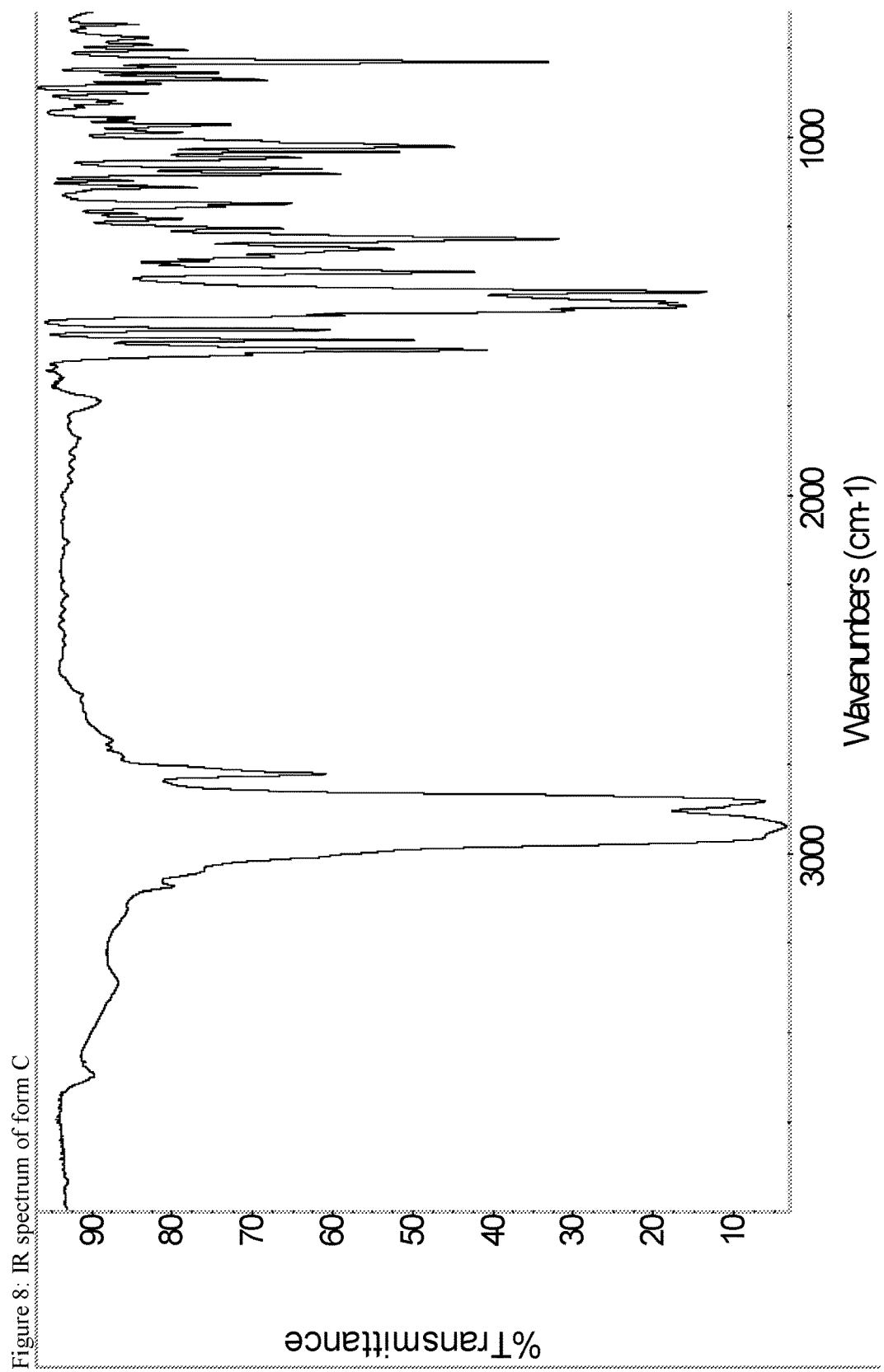

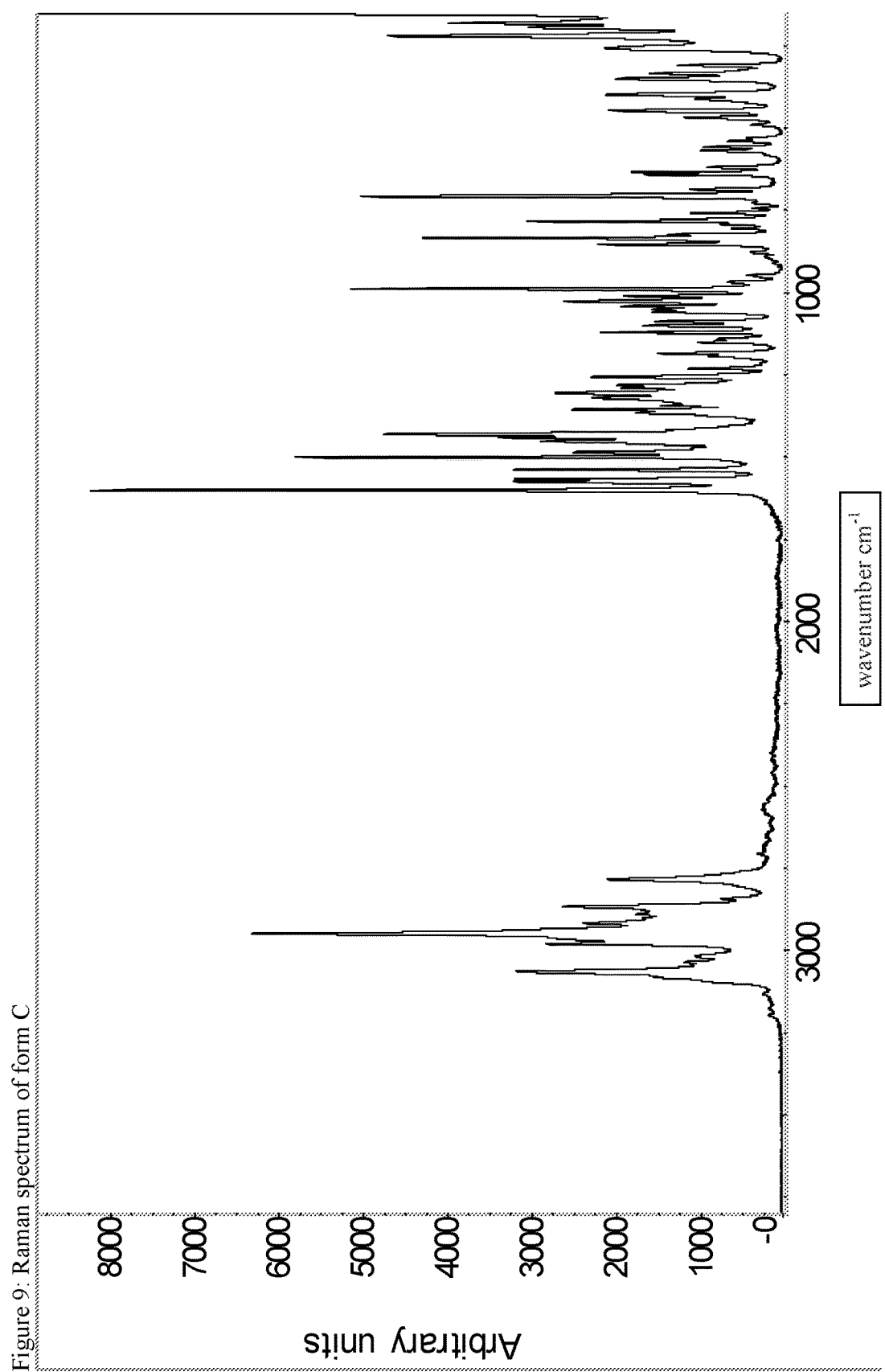
Figure 9: Raman spectrum of form C

Figure 10: XRPD pattern of Form D
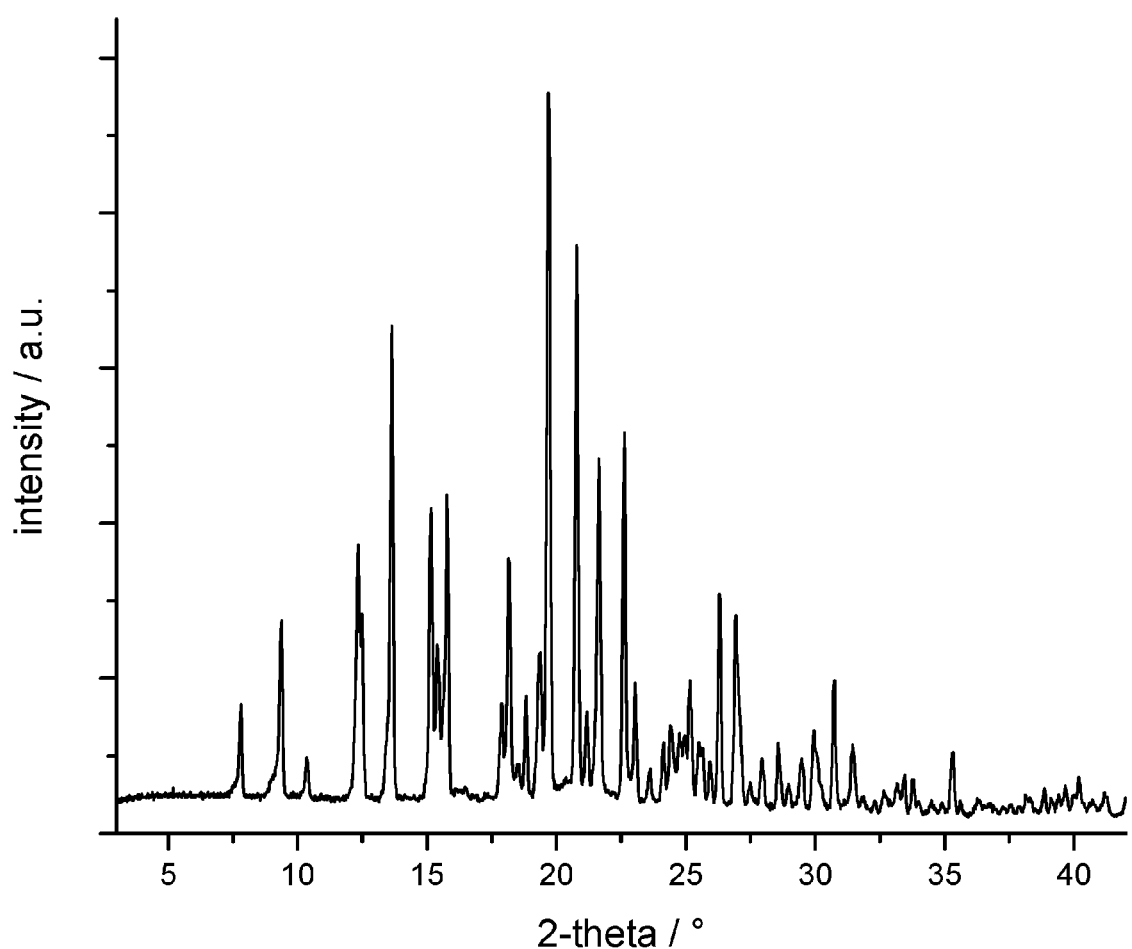

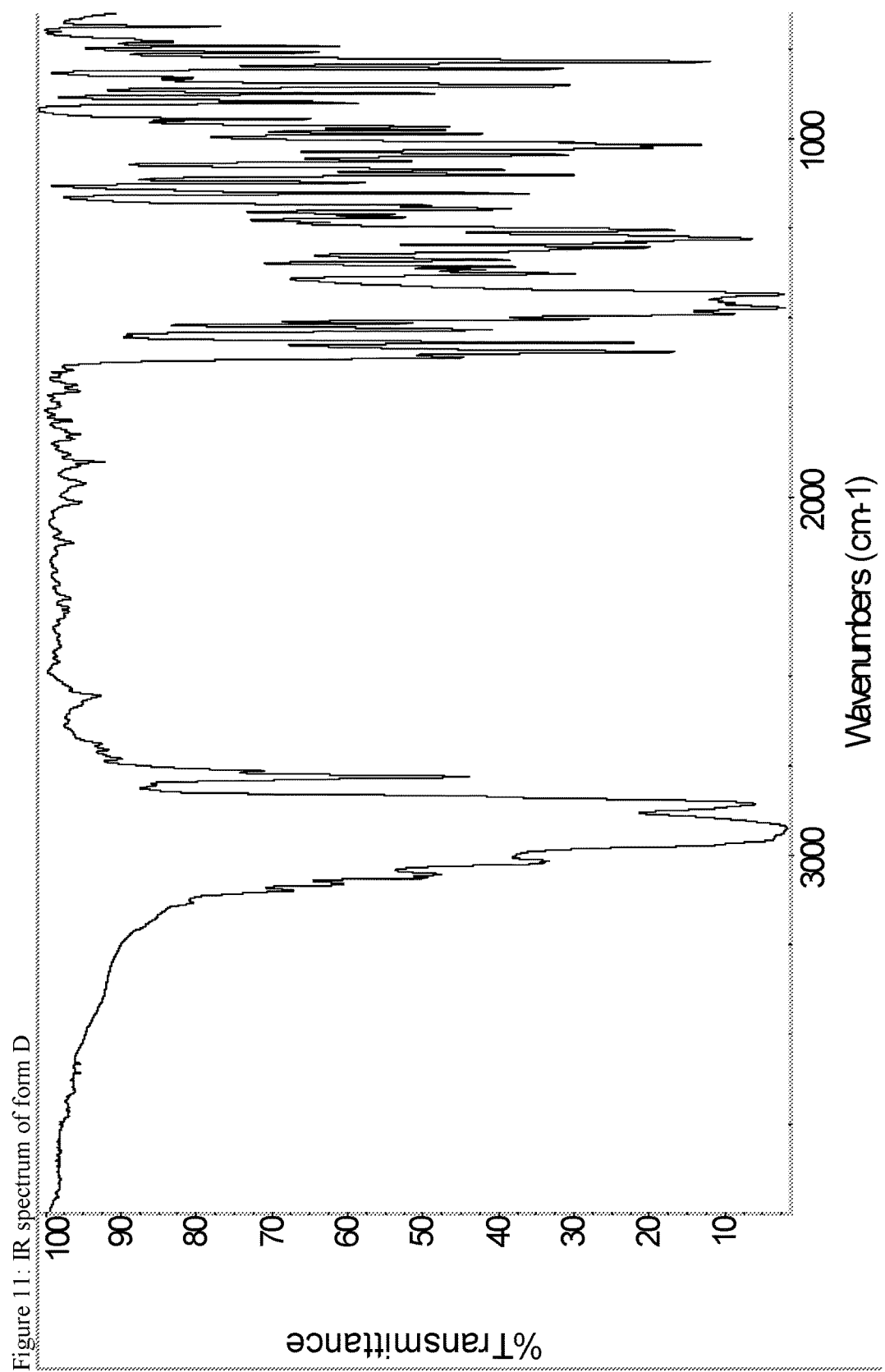
Figure 11: IR spectrum of form D

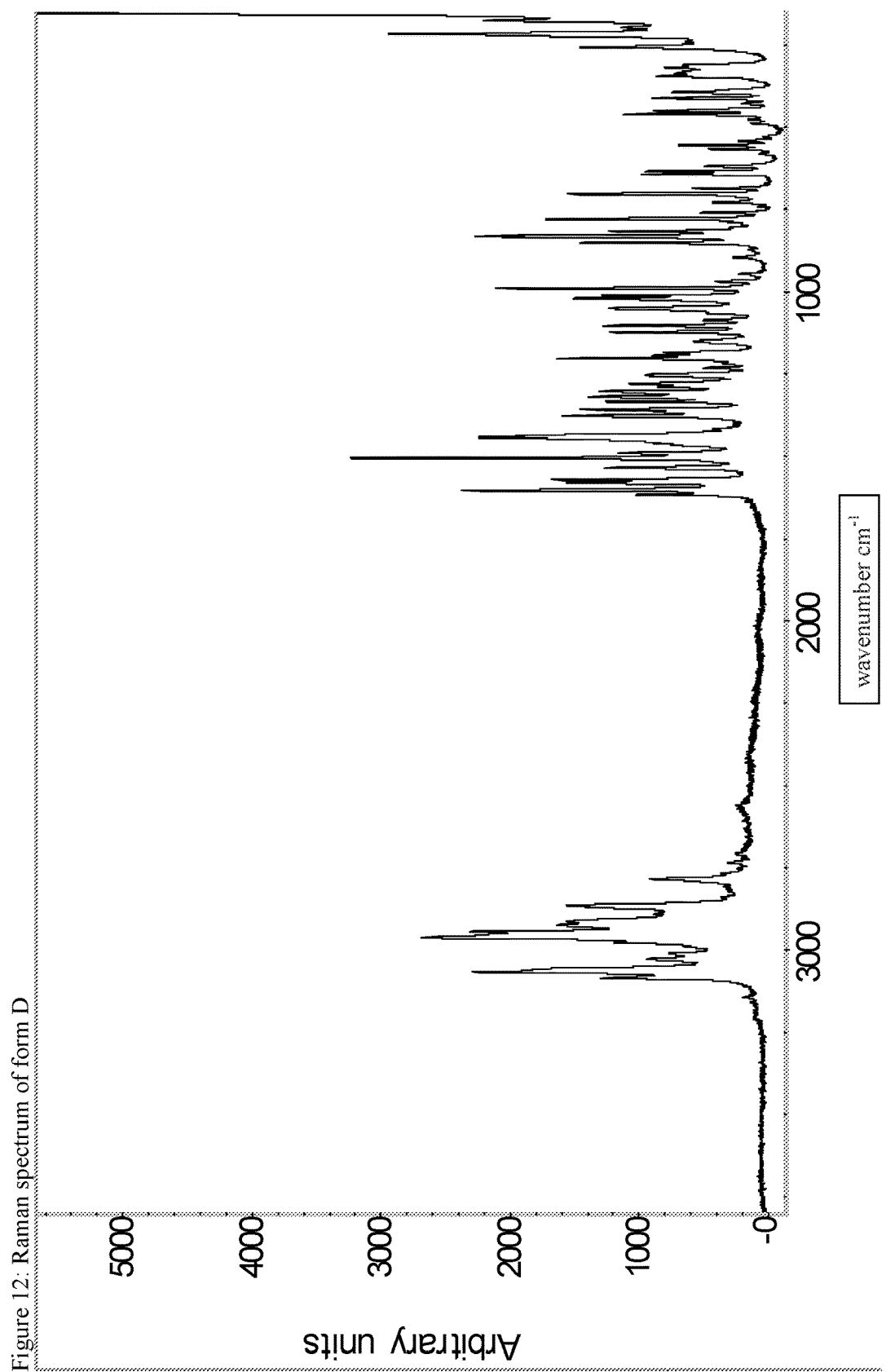
Figure 12: Raman spectrum of form D

Figure 13: XRPD pattern of Form E
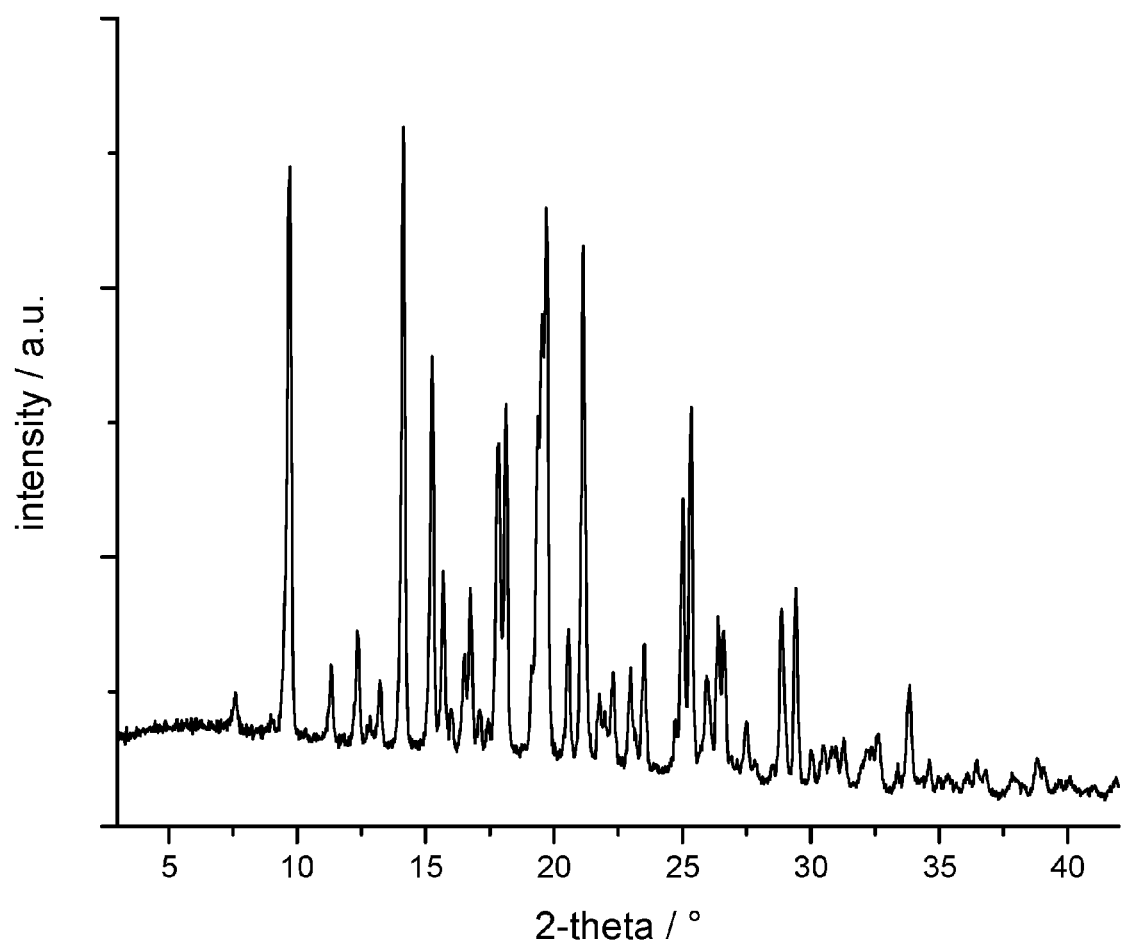

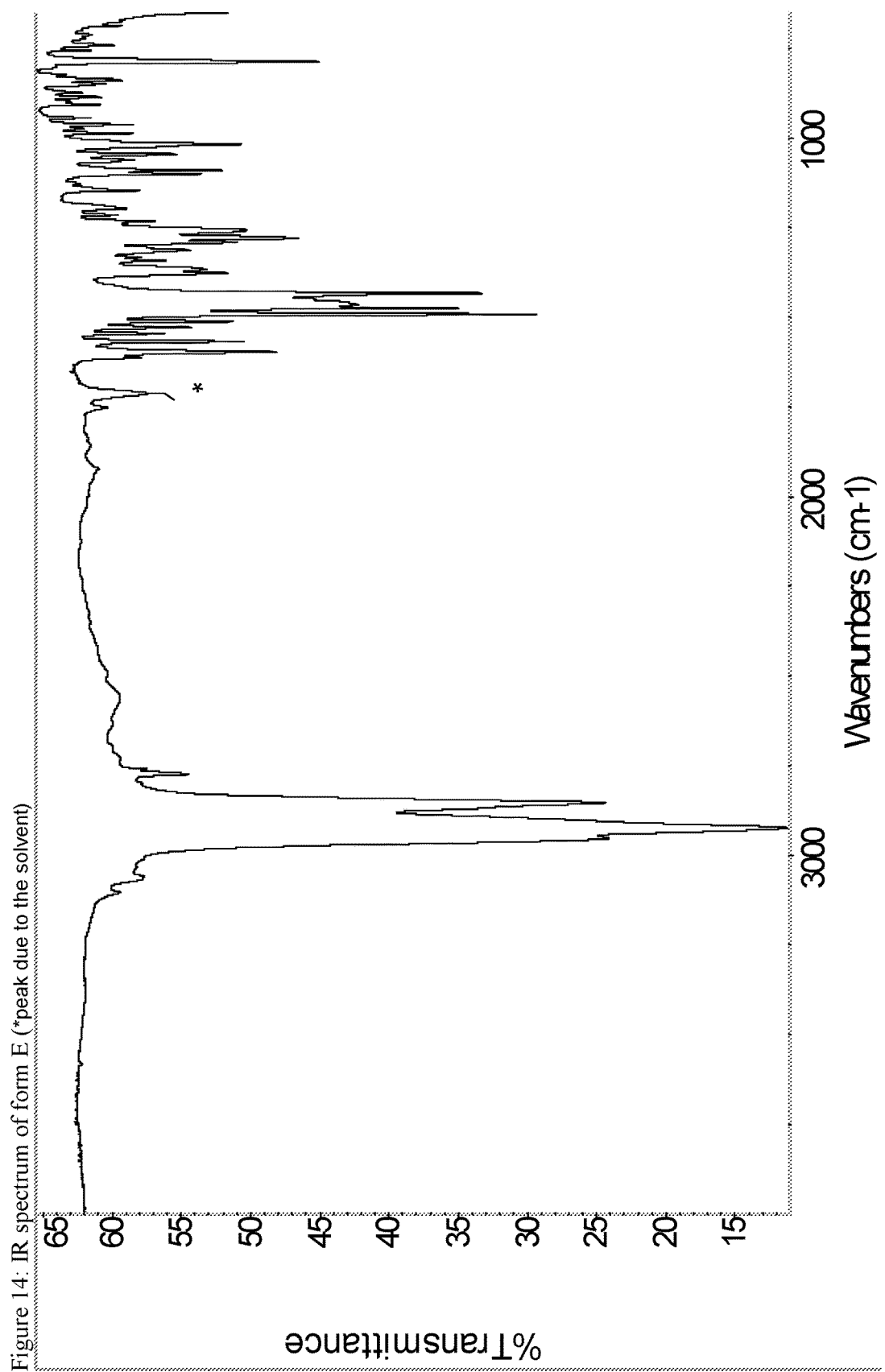
Figure 14: IR spectrum of form E (*peak due to the solvent)

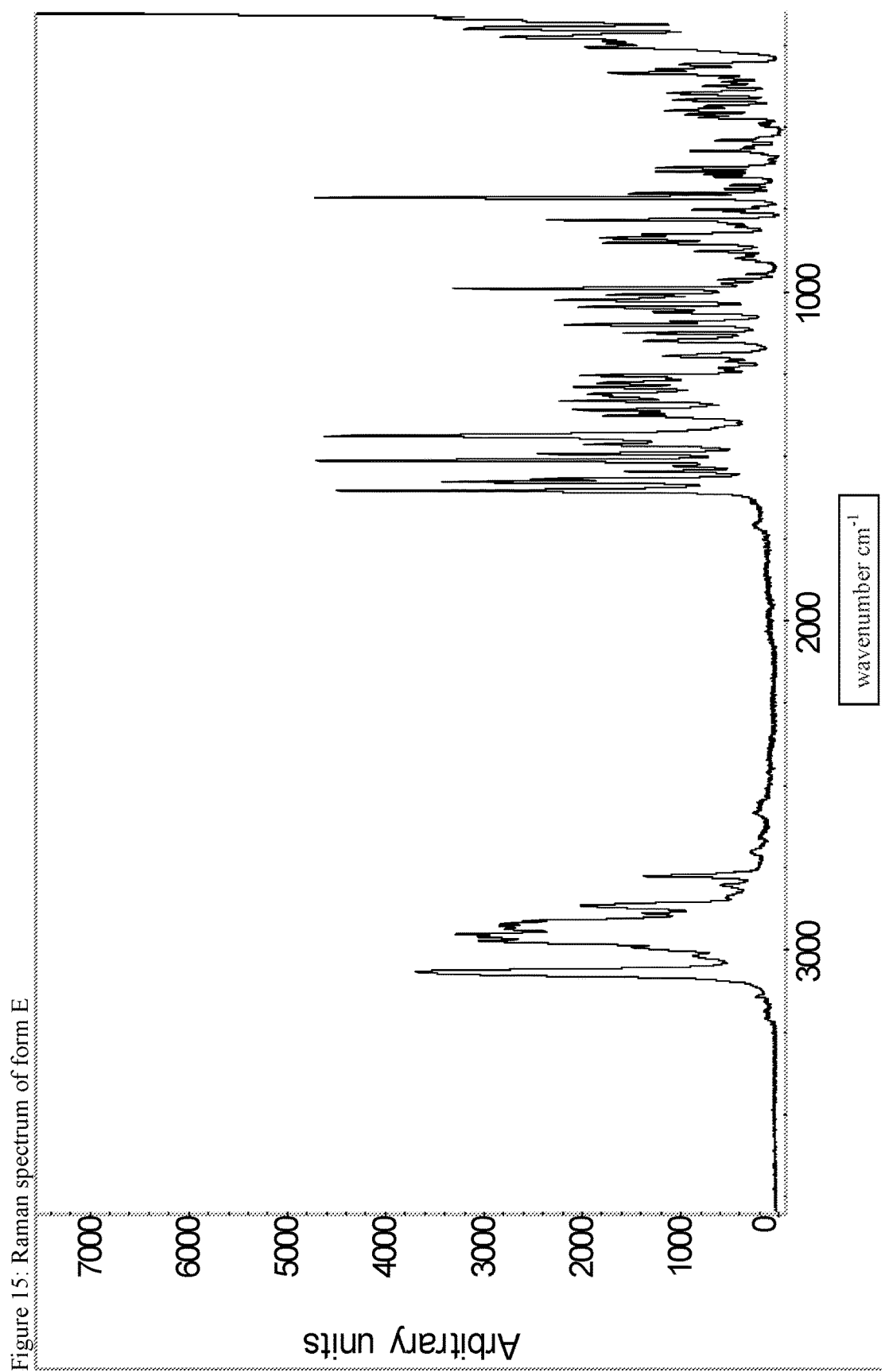
Figure 15: Raman spectrum of form E

Figure 16: XRPD pattern of Form F
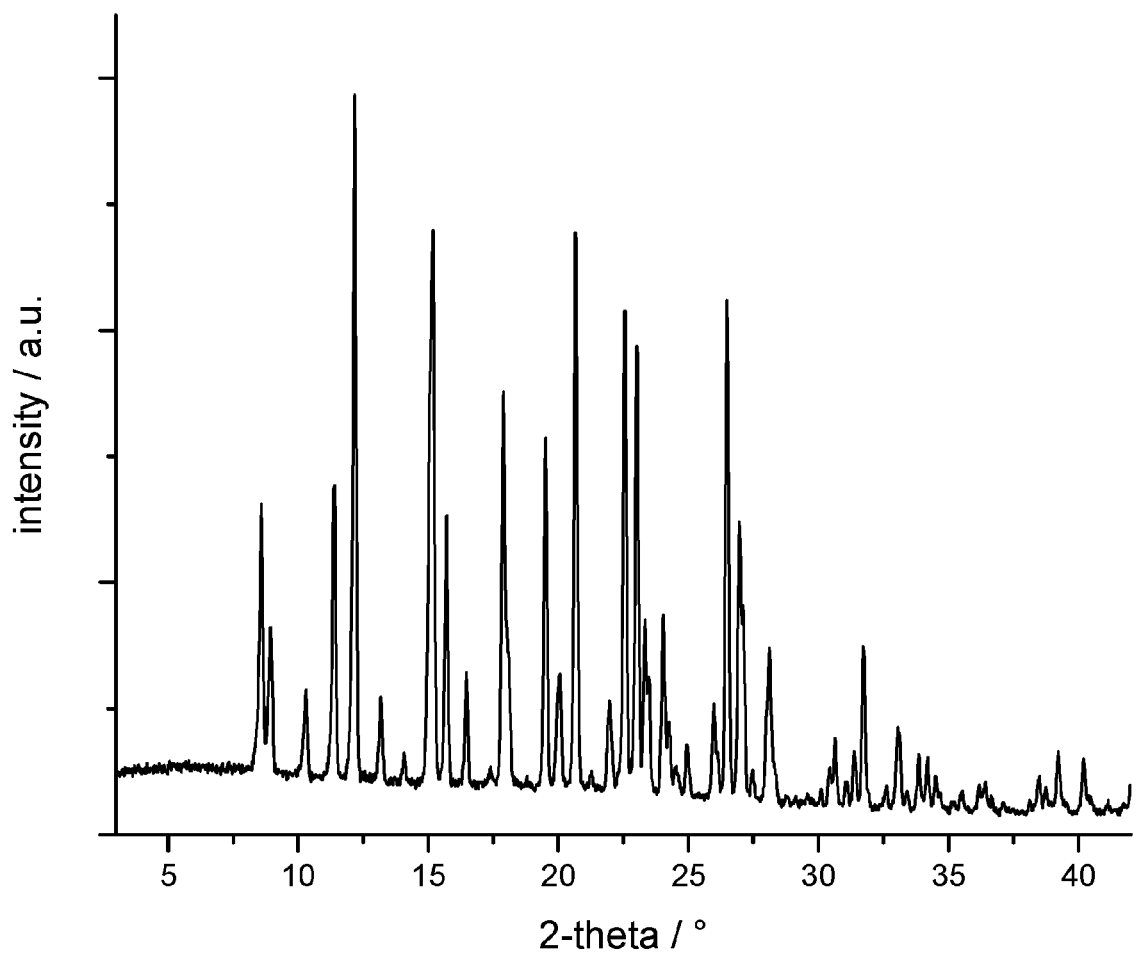

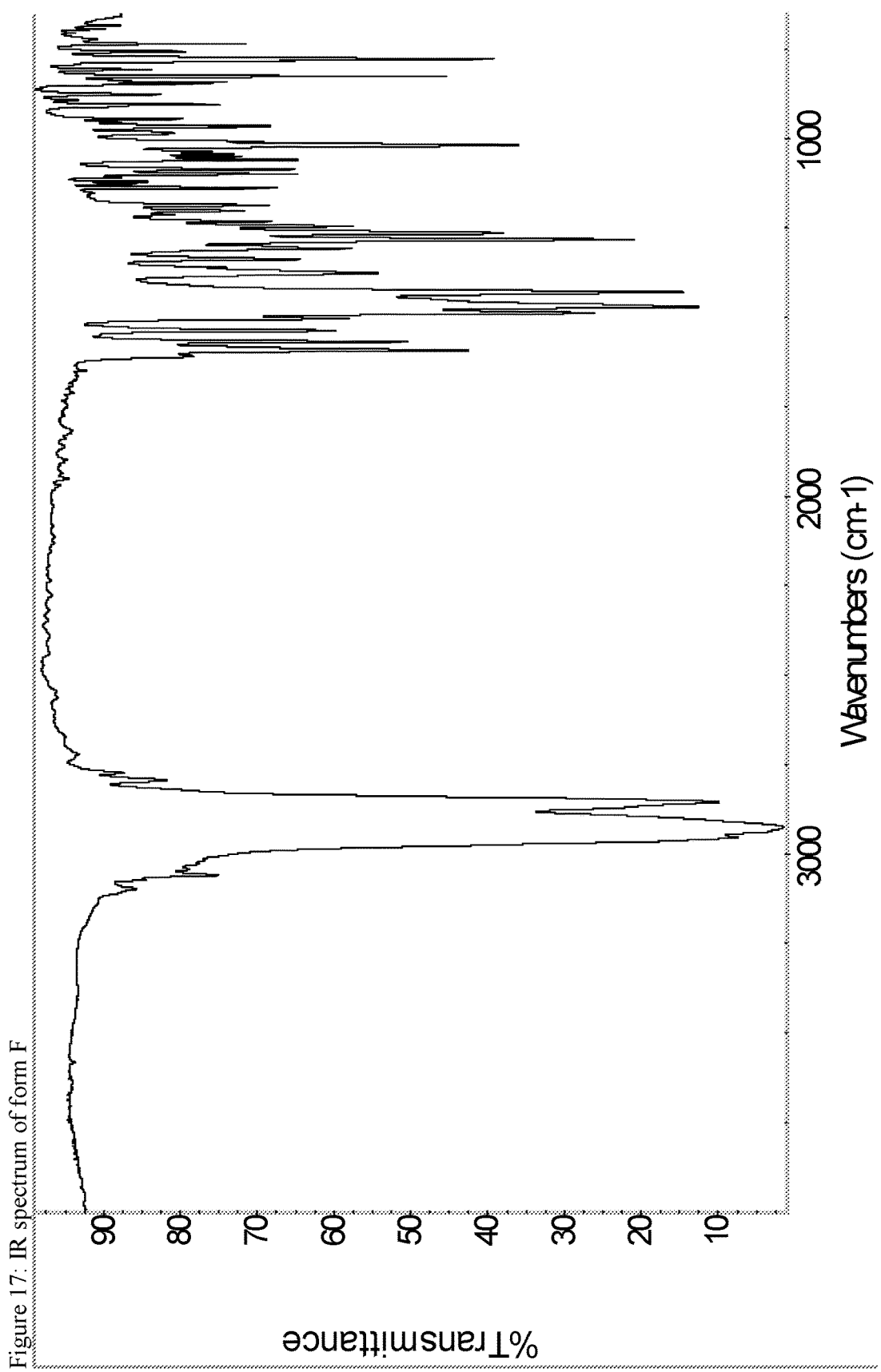
Figure 17: IR spectrum of form F

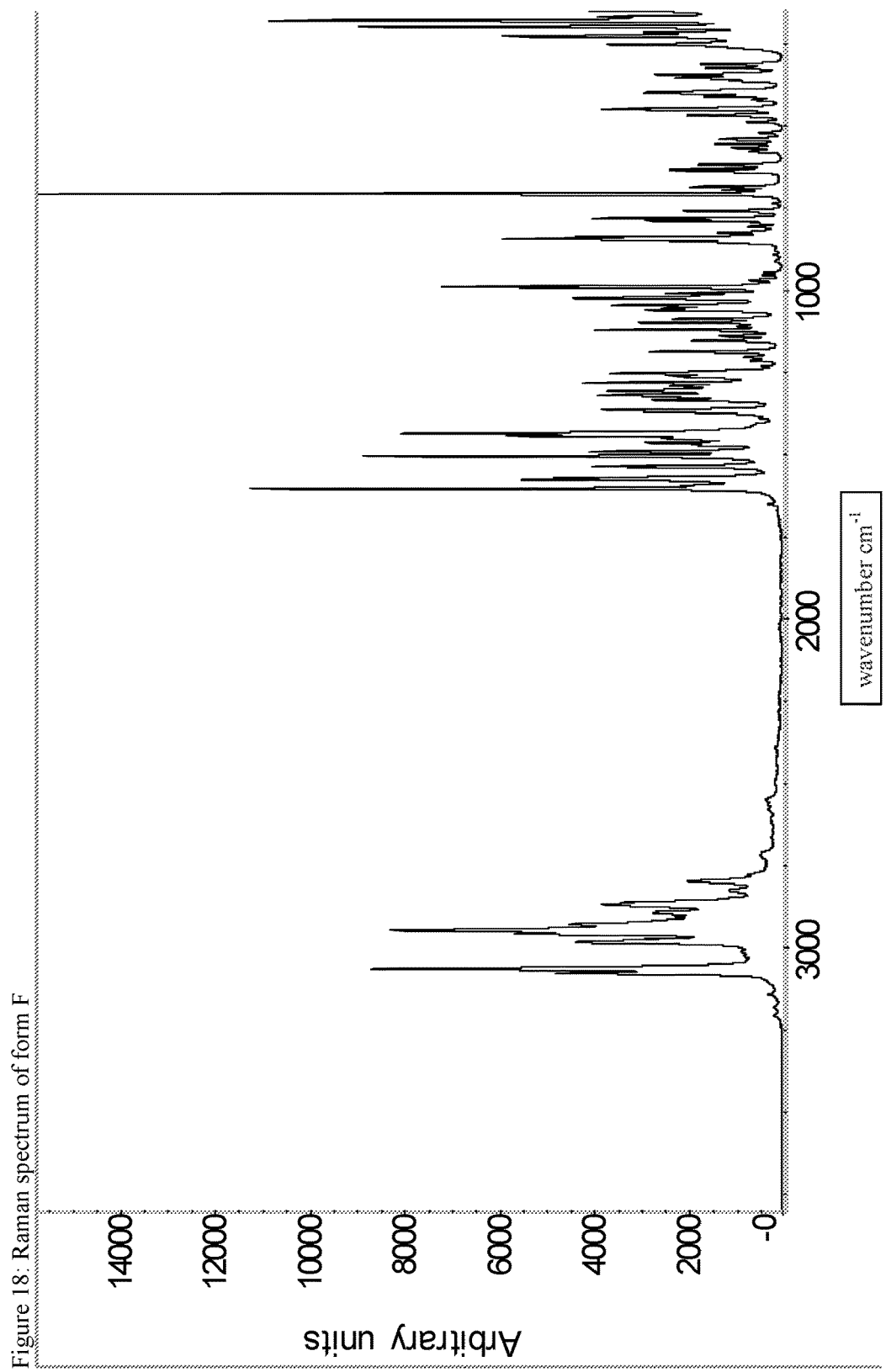
Figure 18: Raman spectrum of form F

Figure 19: XRPD pattern of Form G
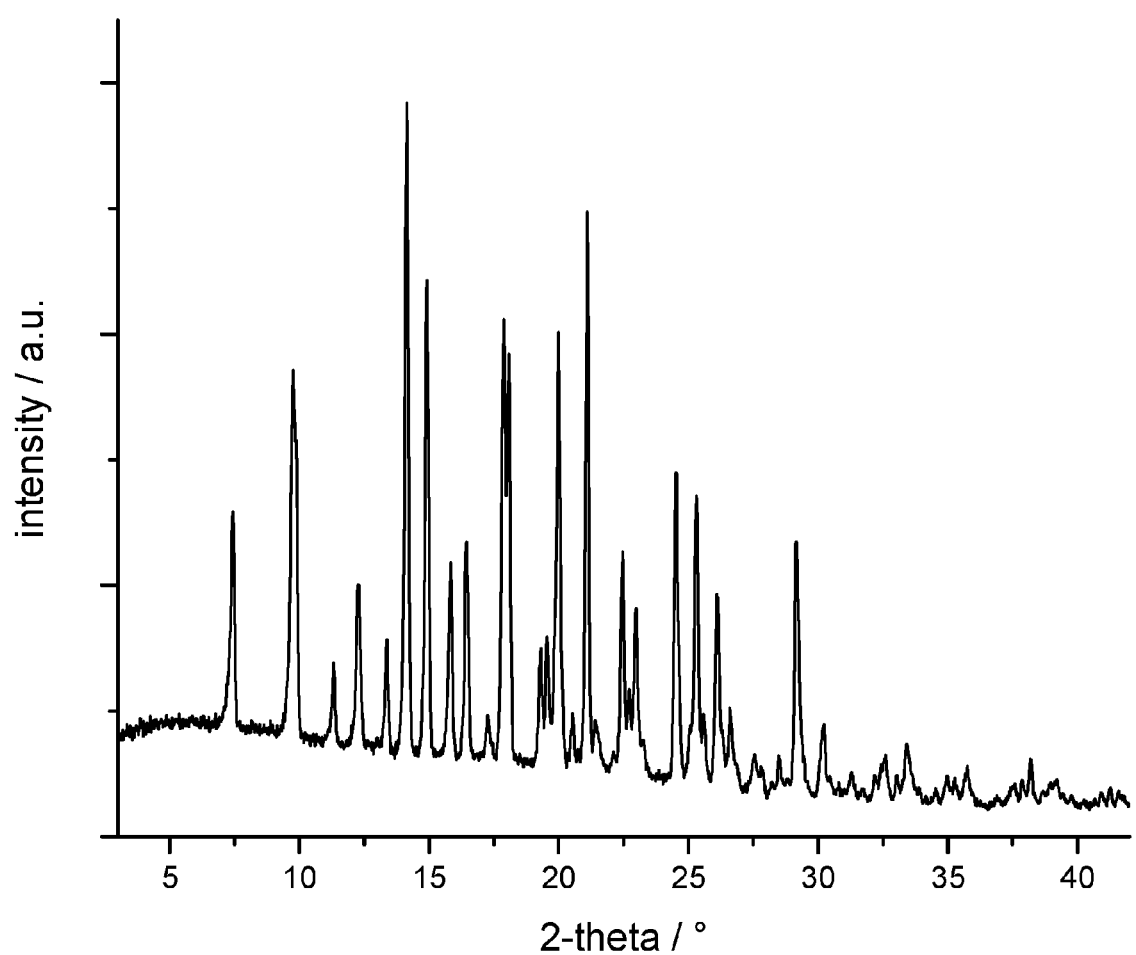

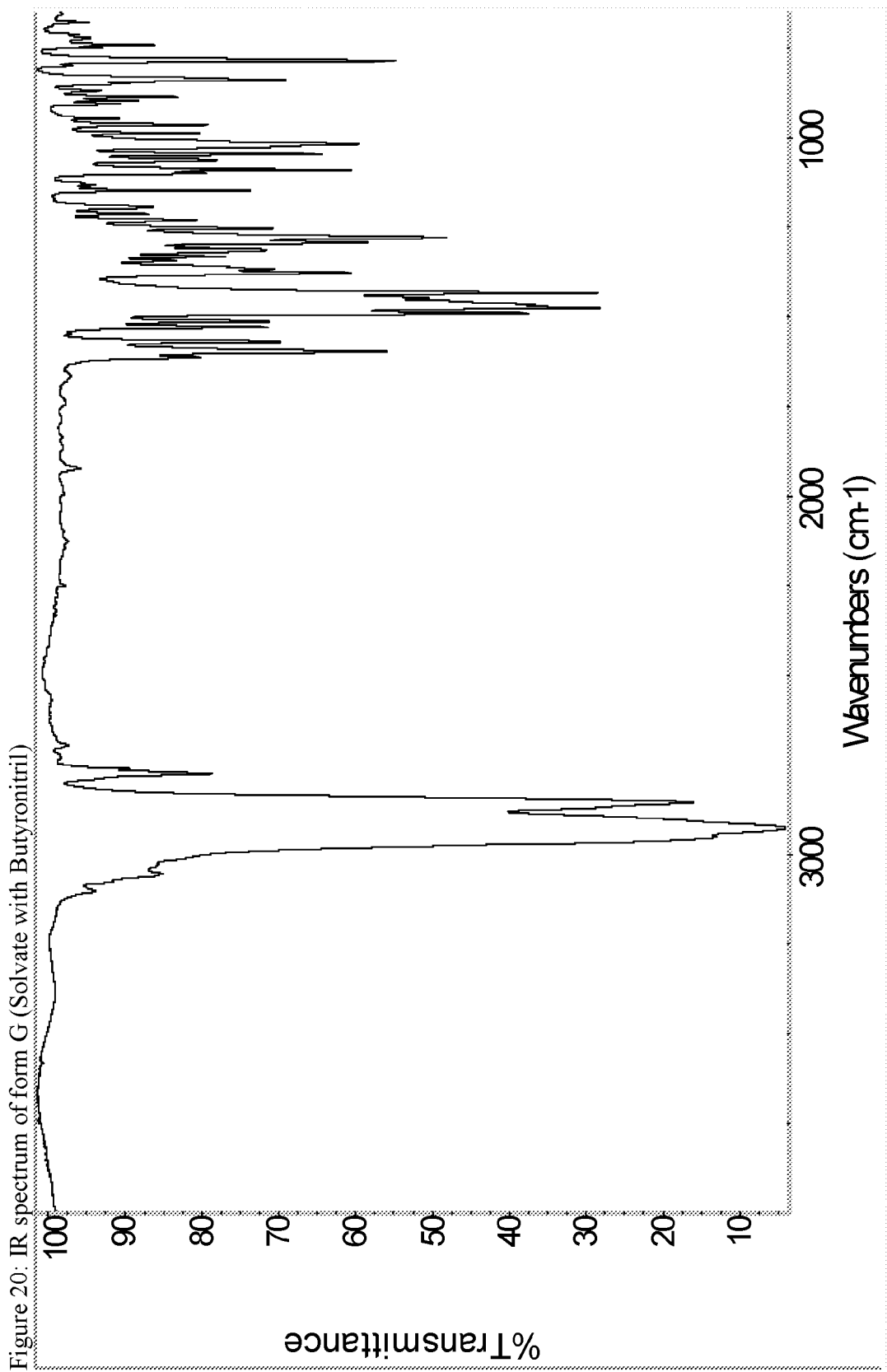
Figure 20: IR spectrum of form G (Solvate with Butyronitril)

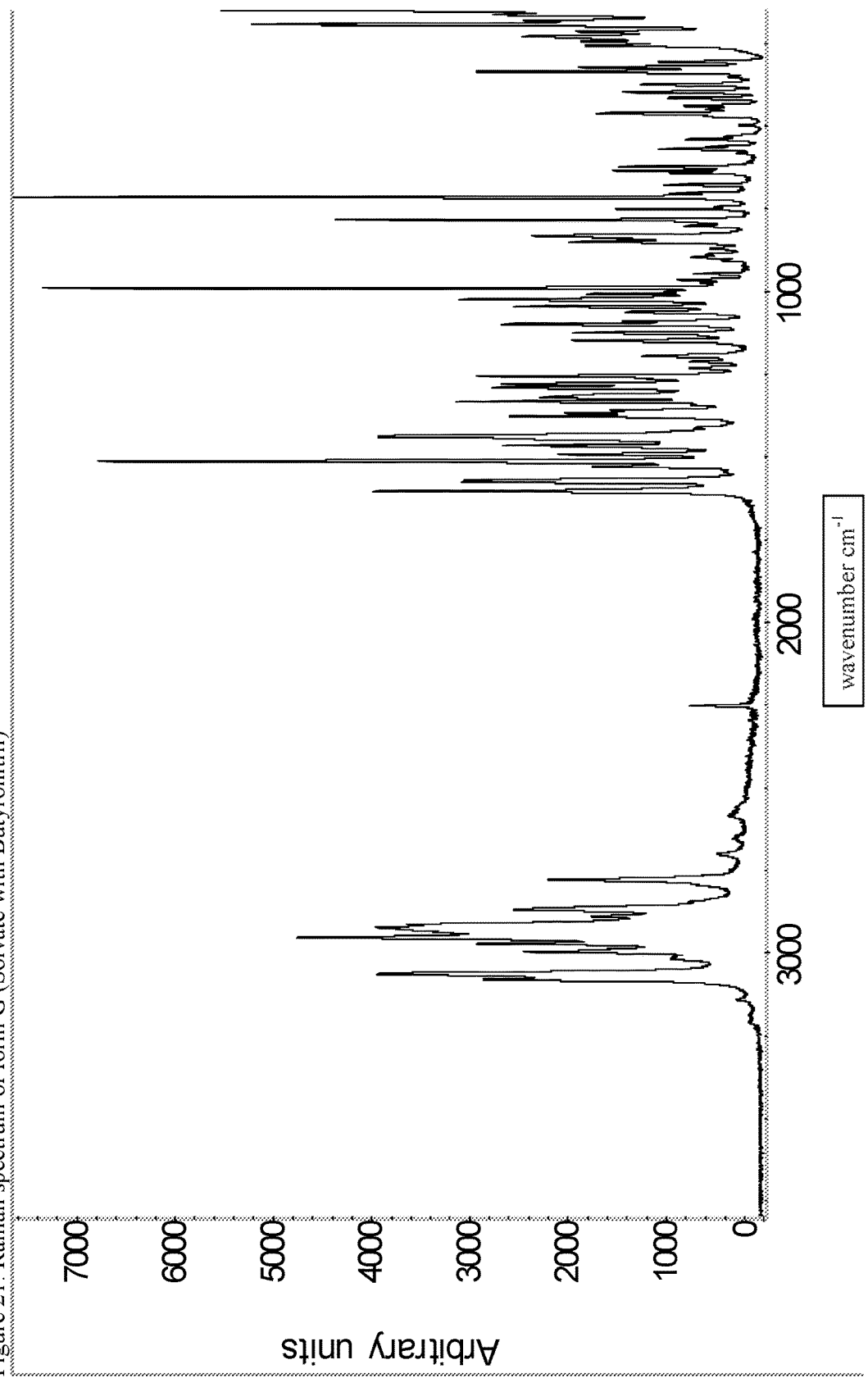
Figure 21: Raman spectrum of form G (Solvate with Butyronitril)

Figure 22: XRPD pattern of Form H
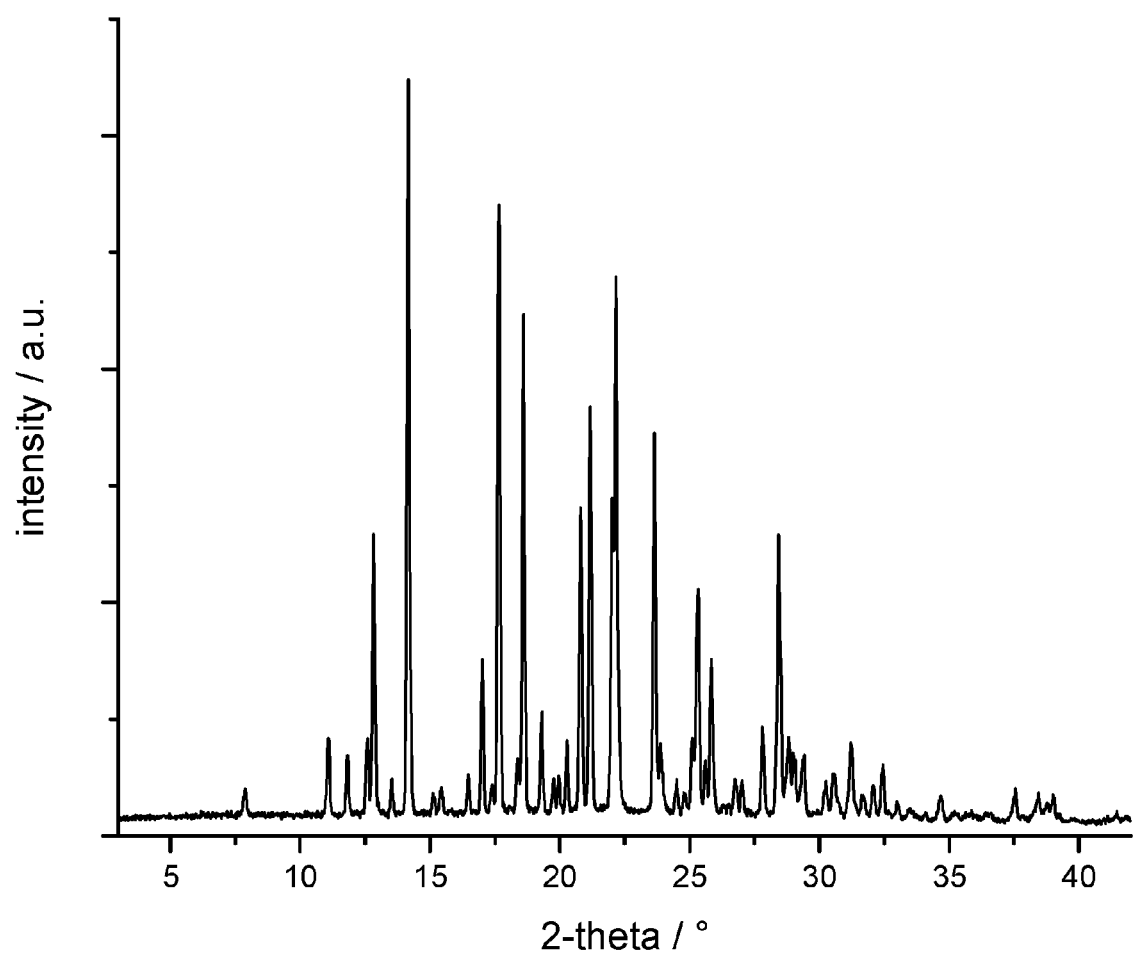

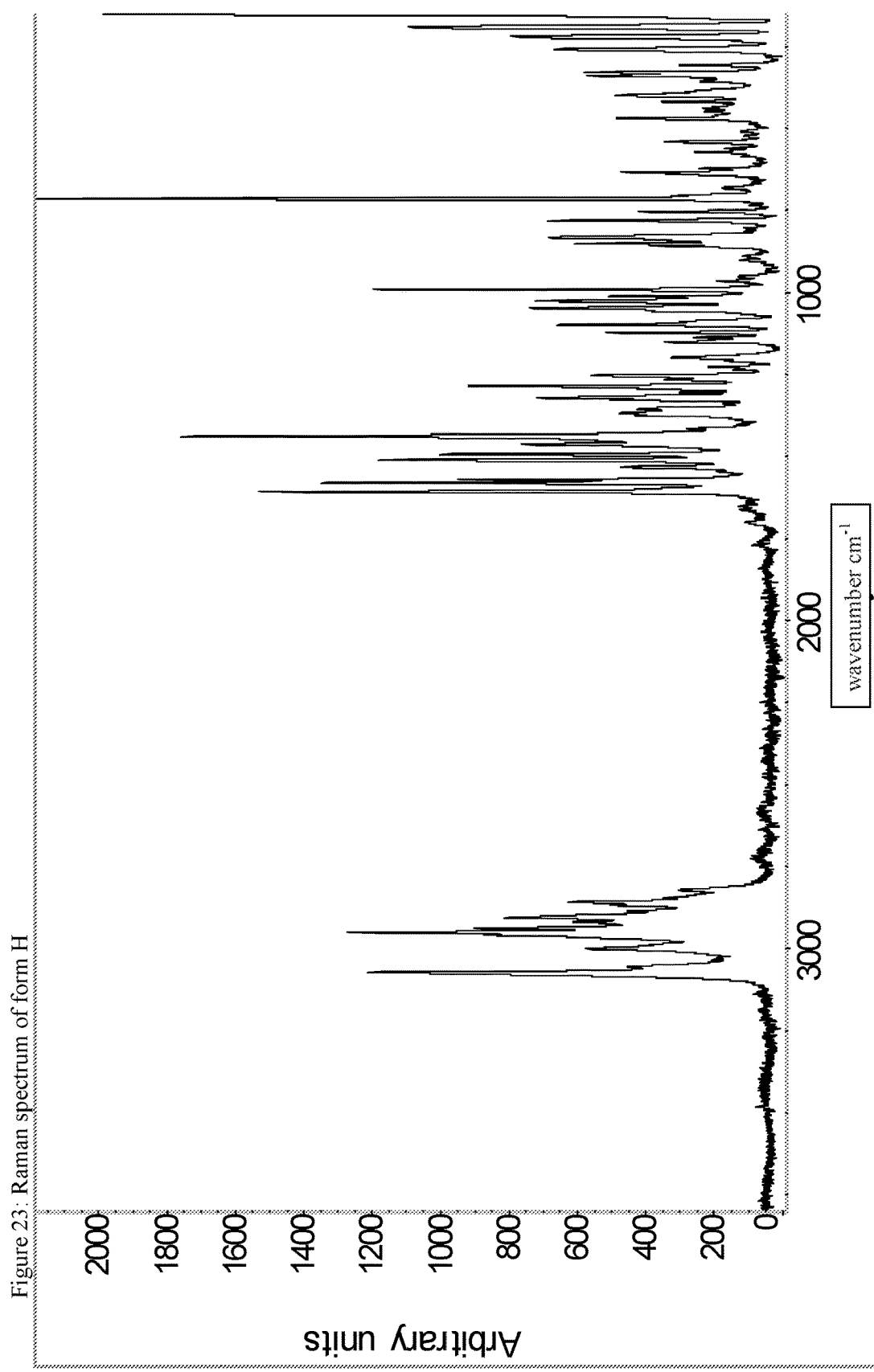
Figure 23: Raman spectrum of form H ically heterogeneous condition characterized by defects in socialization and language. ASD include a wide range of abnormalities including a genuine incapacity to organize affective relations, behavioral anomalies in reciprocal social interactions, verbal and non-verbal communication, limited interest in the surrounding environment associated with stereotyped movements and repetitive plays (Bourreau et al, 2009)[1]. Research to date indicates that a genetic predisposition may be involved, but also environmental factors have to be taken into consideration (Bourgeron, 2009)[2]. There is at present no efficient biological/pharmaceutical treatment of ASD.

[1] Genes, Brain and Behavior (2011) 10: 228-235
[2] Curr. Opin. Neurobiol. 19, 231-234 (2009)

1-[4-(Pyridin-2-yloxy)-cyclohexyl]-5,6-dihydro-4H-2,3,5,10b-tetraaza-benzo[e]azulenes have previously been described in the art[3].

[3] WO2010060836

Further WO2004074291 and WO2005068466[4] describe triazole compounds and a process of manufacturing the same.

[4] WO2004074291 and WO2005068466

It has surprisingly been found that by using the processes according to the present invention 8-chloro-5-methyl-1-[4-(2-pyridyloxy)cyclohexyl]-4,6-dihydro-[1,2,4]triazolo[4,3-a][1,4]benzodiazepine and its pharmaceutically acceptable salts can be prepared more economically with less process steps under moderate reaction conditions with an outstanding yield. Further, crude intermediate products can mostly be used in subsequent reaction steps without the need of any additional purification steps.

Further, several forms have been identified and it has surprisingly been found that form F is the most preferred one.

DEFINITIONS

The following definitions of the general terms used in the present description apply irrespectively of whether the terms in question appear alone or in combination with other groups.

The term "room temperature" (RT) refers to 18-30° C., in particular 20-25° C., more particular to 20° C.

"Solution" as used herein is meant to encompass liquids wherein a reagent or reactant is present in a solvent in dissolved form (as a solute) or is present in particulate, un-dissolved form, or both. Thus, in a "solution", it is contemplated that the solute may not be entirely dissolved therein and solid solute may be present in dispersion or slurry form. Accordingly, a "solution" of a particular reagent or reactant is meant to encompass slurries and dispersions, as well as solutions, of such reagents or reactants. "Solution" and "Slurry" may be used interchangeable herein.

"Solvent" as used herein is meant to encompass liquids that fully dissolve a reagent or reactant exposed to the solvent, as well as liquids which only partially dissolve the reagent or reactant or which act as dispersants for the reagent or reactant. Thus, when a particular reaction is carried out in a "solvent", it is contemplated that some or all of the reagents or reactants present may not be in dissolved form.

The term "approximately" in connection with degrees 2-theta values refers to ±0.2 degrees 2-theta.

The terms "crystalline form" or "form" refer to polymorphic forms and solvates of a compound.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Preferred are formic acid, trifluoroacetic acid and hydrochloric acid. Most preferred is hydrochloric acid.

The terms "Autistic Spectrum" and "Autistic Spectrum Disorders" summarize conditions classified as pervasive developmental disorders, which include but are not limited to autism, Asperger syndrome, pervasive developmental disorder not otherwise specified (PDD-NOS), childhood disintegrative disorder, Rett syndrome and Fragile X, in particular autism. These disorders are typically characterized by social deficits, communication difficulties, stereotyped or repetitive behaviors and interests, and cognitive delays.

The nomenclature used in this Application is based on IUPAC systematic nomenclature, unless indicated otherwise.

DETAILED DESCRIPTION OF THE INVENTION

In detail, the present invention is concerned with a process to synthesize a crystalline form of a compound of formula I

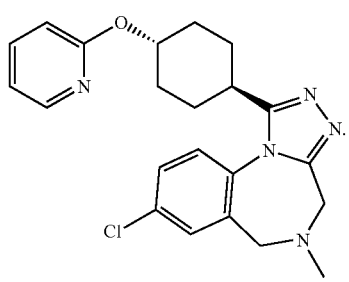

A certain embodiment of the invention relates to the crystalline form A of the compound of formula I as described herein, characterized by a X-ray powder diffraction pattern having the characteristic peaks expressed in values of degrees 2-theta at approximately

| degree 2-theta |
| --- |
| 13.0 |
| 13.5 |
| 14.5 |
| 15.9 |
| 17.8 |
| 18.1 |
| 18.9 |
| 19.5 |
| 20.6 |
| 21.0 |
| 21.9 |
| 23.9 |
| 27.2 |

A certain embodiment of the invention relates to the crystalline form A of the compound of formula I as described herein, characterized by the X-ray powder diffraction pattern as shown in FIG. 1.

A certain embodiment of the invention relates to the crystalline form A of the compound of formula I as described herein, characterized by the Infrared spectrum shown in as shown in FIG. 2.

A certain embodiment of the invention relates to the crystalline form A of the compound of formula I as described herein, characterized by the Raman spectrum shown in as shown in FIG. 3.

A certain embodiment of the invention relates to the crystalline form B of the compound of formula I as described herein, characterized by a X-ray powder diffraction pattern having the characteristic peaks expressed in values of degrees 2-theta at approximately

| degree 2-theta |
| --- |
| 7.5 |
| 9.9 |
| 12.4 |
| 14.3 |
| 15.1 |
| 15.9 |
| 16.6 |
| 18.1 |
| 20.0 |
| 21.2 |
| 24.8 |
| 25.5 |

A certain embodiment of the invention relates to the crystalline form B of the compound of formula I as described herein, characterized by the X-ray powder diffraction pattern as shown in FIG. 4.

A certain embodiment of the invention relates to the crystalline form B of the compound of formula I as described herein, characterized by the Infrared spectrum shown in as shown in FIG. 5.

A certain embodiment of the invention relates to the crystalline form B of the compound of formula I as described herein, characterized by the Raman spectrum shown in as shown in FIG. 6.

A certain embodiment of the invention relates to the crystalline form B of the compound of formula I as described herein, characterized by the following unit cell parameters

| A | 12.01 Å |
| --- | --- |
| B | 17.91 Å |
| C | 10.52 Å |
| alpha | 90 deg |
| beta | 101.14 deg |
| gamma | 90 deg |

A certain embodiment of the invention relates to the crystalline form C of the compound of formula I as described herein, characterized by a X-ray powder diffraction pattern having the characteristic peaks expressed in values of degrees 2-theta at approximately

| degree 2-theta |
| --- |
| 9.0 |
| 12.6 |
| 13.7 |
| 16.6 |
| 18.1 |
| 18.4 |
| 19.4 |
| 19.7 |
| 20.2 |
| 20.8 |
| 22.5 |
| 23.0 |

A certain embodiment of the invention relates to the crystalline form C of the compound of formula I as described herein, characterized by the X-ray powder diffraction pattern as shown in FIG. 7.

A certain embodiment of the invention relates to the crystalline form C of the compound of formula I as described herein, characterized by the Infrared spectrum shown in as shown in FIG. 8.

A certain embodiment of the invention relates to the crystalline form C of the compound of formula I as described herein, characterized by the Raman spectrum shown in as shown in FIG. 9.

A certain embodiment of the invention relates to the crystalline form C of the compound of formula I as described herein, characterized by the following unit cell parameters

| A | 10.80 Å |
| --- | --- |
| B | 18.16 Å |
| C | 18.42 Å |
| alpha | 108.64 deg |
| beta | 99.57 deg |
| gamma | 106.79 deg |

A certain embodiment of the invention relates to the crystalline form D of the compound of formula I as described herein, characterized by a X-ray powder diffraction pattern having the characteristic peaks expressed in values of degrees 2-theta at approximately

| degree 2-theta |
| --- |
| 7.8 |
| 9.4 |
| 12.3 |
| 13.6 |
| 15.2 |
| 15.8 |
| 18.2 |

-continued

| degree 2-theta |
|---|
| 19.7 |
| 20.8 |
| 21.6 |
| 22.6 |
| 26.3 |
| 26.9 |

A certain embodiment of the invention relates to the crystalline form D of the compound of formula I as described herein, characterized by the X-ray powder diffraction pattern as shown in FIG. 10.

A certain embodiment of the invention relates to the crystalline form D of the compound of formula I as described herein, characterized by the Infrared spectrum shown in as shown in FIG. 11.

A certain embodiment of the invention relates to the crystalline form D of the compound of formula I as described herein, characterized by the Raman spectrum shown in as shown in FIG. 12.

A certain embodiment of the invention relates to the crystalline form D of the

| | |
|---|---|
| A | 11.74 Å |
| B | 9.08 Å |
| C | 22.93 Å |
| alpha | 90 deg |
| beta | 103.84 deg |
| gamma | 90 deg |

A certain embodiment of the invention relates to the crystalline form E of the compound of formula I as described herein, characterized by a X-ray powder diffraction pattern having the characteristic peaks expressed in values of degrees 2-theta at approximately

| degree 2-theta |
|---|
| 9.7 |
| 12.4 |
| 14.1 |
| 15.2 |
| 15.7 |
| 16.7 |
| 17.8 |
| 18.1 |
| 19.7 |
| 21.1 |
| 25.0 |
| 23.3 |
| 28.9 |
| 29.4 |

A certain embodiment of the invention relates to the crystalline form E of the compound of formula I as described herein, characterized by the X-ray powder diffraction pattern as shown in FIG. 13.

A certain embodiment of the invention relates to the crystalline form E of the compound of formula I as described herein, characterized by the Infrared spectrum shown in as shown in FIG. 14.

A certain embodiment of the invention relates to the crystalline form E of the compound of formula I as described herein, characterized by the Raman spectrum shown in as shown in FIG. 15.

A certain embodiment of the invention relates to the crystalline form F of the compound of formula I as described herein, characterized by a X-ray powder diffraction pattern having the characteristic peaks expressed in values of degrees 2-theta at approximately

| degree 2-theta |
|---|
| 8.6 |
| 8.9 |
| 11.4 |
| 12.2 |
| 15.2 |
| 15.7 |
| 17.9 |
| 19.5 |
| 20.7 |
| 22.6 |
| 23.0 |
| 24.0 |
| 26.5 |
| 27.0 |

A certain embodiment of the invention relates to the crystalline form F of the compound of formula I as described herein, characterized by the X-ray powder diffraction pattern as shown in FIG. 16.

A certain embodiment of the invention relates to the crystalline form F of the compound of formula I as described herein, characterized by the Infrared spectrum shown in as shown in FIG. 17.

A certain embodiment of the invention relates to the crystalline form F of the compound of formula I as described herein, characterized by the Raman spectrum shown in as shown in FIG. 18.

A certain embodiment of the invention relates to the crystalline form F of the compound of formula I as described herein, characterized by the following unit cell parameters

| | |
|---|---|
| A | 8.98 Å |
| B | 11.30 Å |
| C | 12.02 Å |
| alpha | 117.01 deg |
| beta | 102.48 deg |
| gamma | 94.76 deg |

A certain embodiment of the invention relates to the crystalline form G of the compound of formula I as described herein, characterized by a X-ray powder diffraction pattern having the characteristic peaks expressed in values of degrees 2-theta at approximately

| degree 2-theta |
|---|
| 7.4 |
| 9.8 |
| 12.3 |
| 14.1 |
| 14.9 |
| 15.8 |
| 16.4 |
| 17.9 |
| 18.1 |
| 20.0 |
| 21.1 |
| 22.5 |
| 24.5 |
| 25.3 |
| 29.2 |

A certain embodiment of the invention relates to the crystalline form G of the compound of formula I as described herein, characterized by the X-ray powder diffraction pattern as shown in FIG. 19.

A certain embodiment of the invention relates to the crystalline form G of the compound of formula I as described herein, characterized by the Infrared spectrum shown in as shown in FIG. 20.

A certain embodiment of the invention relates to the crystalline form G of the compound of formula I as described herein, characterized by the Raman spectrum shown in as shown in FIG. 21.

A certain embodiment of the invention relates to the crystalline form G of the compound of formula I as described herein, characterized by the following unit cell parameters

| | |
|---|---|
| A | 12.02 Å |
| B | 18.04 Å |
| C | 10.29 Å |
| alpha | 90 deg. |
| beta | 100.63 deg. |
| gamma | 90 deg. |

A certain embodiment of the invention relates to the crystalline form H of the compound of formula I as described herein, characterized by a X-ray powder diffraction pattern having the characteristic peaks expressed in values of degrees 2-theta at approximately

| degree 2-theta |
|---|
| 12.8 |
| 14.2 |
| 17.0 |
| 17.7 |
| 18.6 |
| 20.8 |
| 21.2 |
| 22.2 |
| 23.6 |
| 25.3 |
| 28.4 |

A certain embodiment of the invention relates to the crystalline form H of the compound of formula I as described herein, characterized by the X-ray powder diffraction pattern as shown in FIG. 22.

A certain embodiment of the invention relates to the crystalline form H of the compound of formula I as described herein, characterized by the Raman spectrum shown in as shown in FIG. 23.

A certain embodiment of the invention relates to the crystalline form H of the compound of formula I as described herein, characterized by the following unit cell parameters

| | |
|---|---|
| A | 22.76 Å |
| B | 8.52 Å |
| C | 12.55 Å |
| alpha | 90 deg |
| beta | 99.18 deg |
| gamma | 90 deg |

A certain embodiment of the invention relates to a process to transform form A to form F.

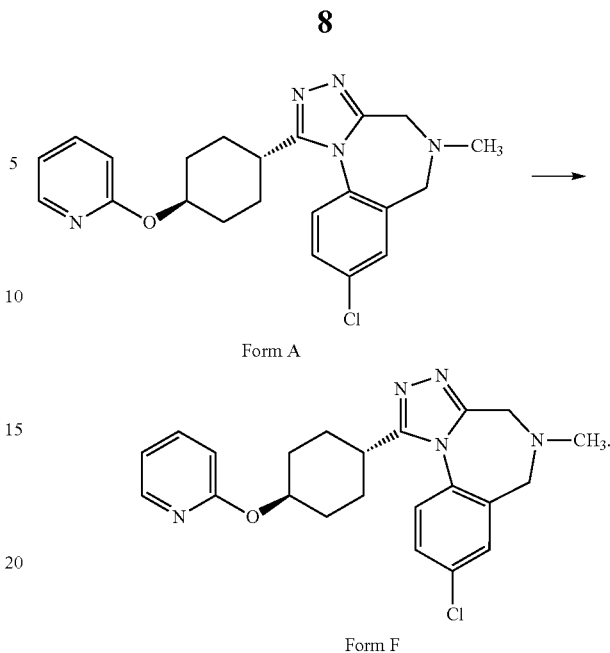

Form A

Form F

A certain embodiment of the invention relates to the trihydrate of a compound of formula I.

A certain embodiment of the invention relates to a process to synthesize a compound of formula I as described herein, comprising reacting a compound of formula II with a compound of formula VI

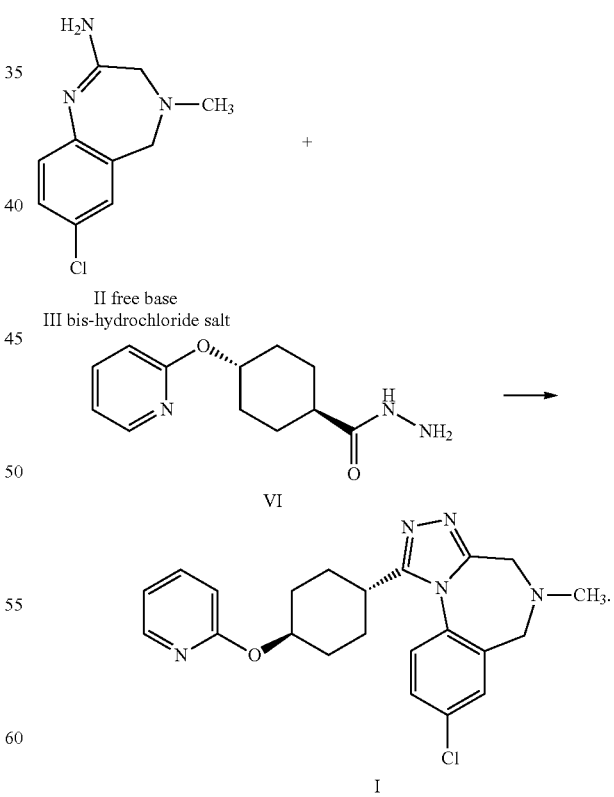

II free base
III bis-hydrochloride salt

VI

I

The amidine free base II can be reacted thermally with the compound of formula VI to provide the compound of formula I. The presence of an acid enhances the reactivity and the purity of the crude API. This is conveniently achieved by using the amidine bis-hydrochloride III as a substrate. III can be isolated as crystalline intermediate which thus provides a good purification point in that synthesis.

A certain embodiment of the invention relates to a process to synthesize a compound of formula I as described herein, comprising reacting a compound of formula III with a compound of formula VI.

A certain embodiment of the invention relates to a process to synthesize a compound of formula I as described herein, comprising reacting a compound of formula III with a compound of formula VI, whereby they are reacted thermally, in particular at a temperature of 95° C.±35° C., more particular 85° C.±15° C., most particular 80° C.±5° C. Specific temperatures are 75° C., 76° C., 77° C., 78° C., 79° C., 80° C., 81° C., 82° C., 83° C., 84° C. and 85° C.

A certain embodiment of the invention relates to a process to synthesize a compound of formula I as described herein, comprising reacting a compound of formula III with a compound of formula VI in an organic solvent like THF, dioxane, DMF, NMP, acetonitrile and alcohols, in particular an alcoholic solvent like ethanol, n-propanol, isopropanol, n-butanol, more particularly isopropanol and n-propanol, even more particularly isopropanol. Compound I can be directly isolated as hydrochloride by filtration when the reaction is performed in a suitable solvent like isopropanol. Alternatively, I as free base can be isolated by addition of an aqueous base like aqueous sodium hydroxide, aqueous potassium hydroxide, aqueous sodium bicarbonate, aqueous potassium bicarbonate, aqueous sodium carbonate, aqueous potassium carbonate, in particular, aqueous sodium hydroxide, aqueous potassium hydroxide, more particular aqueous sodium hydroxide. The compound I is then isolated as trihydrate (form H) which leads to the anhydrous form A upon drying.

A certain embodiment of the invention relates to a process to synthesize a compound of formula I as described herein, comprising reacting a compound of formula II with a compound of formula VI, whereby the free base of the product I is isolated at pH>8, in particular, at pH>10, more particularly at pH>12.

A certain embodiment of the invention relates to isolation of the free base of the product I at pH>8, in particular, at pH>10, more particularly at pH>12 using an appropriate solvent mixture like an alcohol/water mixture, in particular ethanol/water, isopropanol/water, n-propanol/water, more particular isopropanol/water, free of un-desired byproduct 4-(2-pyridyloxy)-N'-[4-(2-pyridyloxy) cyclohexanecarbonyl]cyclohexane-carbohydrazide (VI').

A certain embodiment of the invention relates to a process to synthesize a compound of formula I as described herein, comprising reacting a compound of formula II with a compound of formula VI, whereby 4-(2-pyridyloxy)-N'-[4-(2-pyridyloxy) cyclohexanecarbonyl]cyclohexane-carbohydrazide VI' is the byproduct.

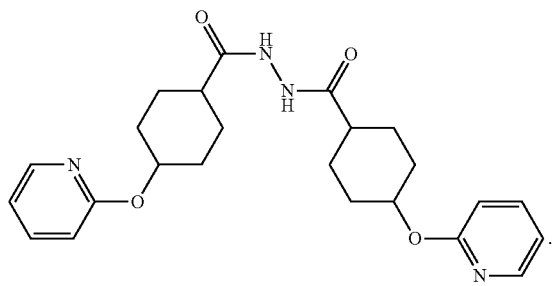

VI'

A certain embodiment of the invention relates to the process as described above, further comprising reacting a compound of formula XI or a hydrochloride salt thereof to a compound of formula III:

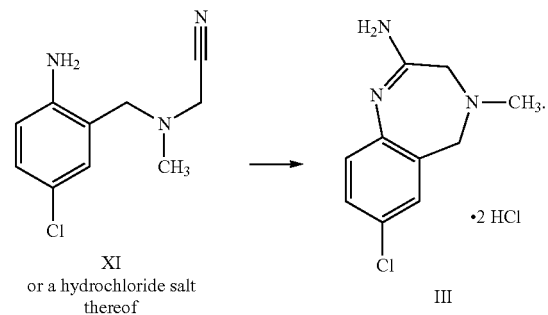

XI
or a hydrochloride salt thereof

III

A certain embodiment of the invention relates to the process as described above further comprising reacting a compound of formula X to a compound of formula XI via the following steps:

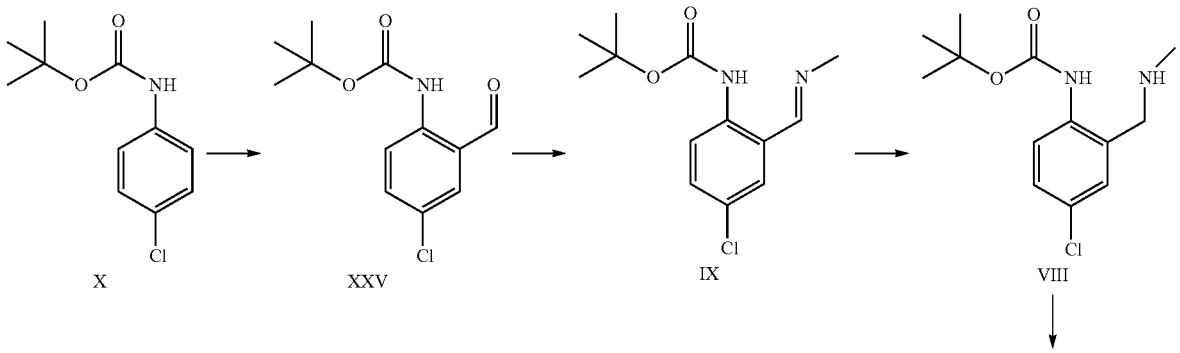

-continued

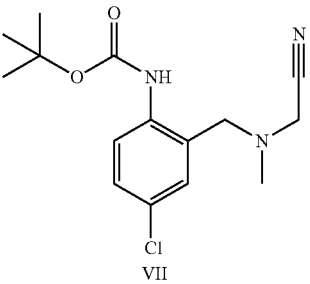

Compound of formula XI can be isolated as a bis-hydrochloride. Alternatively, it can be prepared in-situ and directly further converted to compound of formula III.

A certain embodiment of the invention relates to the process as described above further comprising reacting a compound of formula X to a compound of formula III via the following steps:

-continued

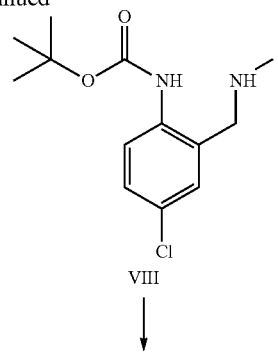

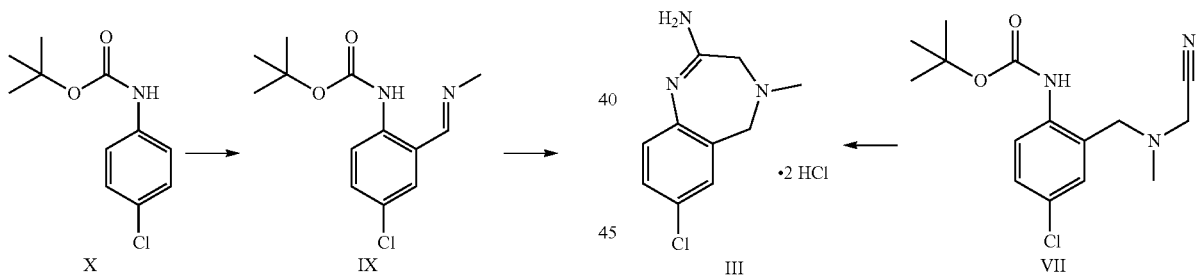

A certain embodiment of the invention relates to the process to synthesize a compound of formula I comprising the following steps:

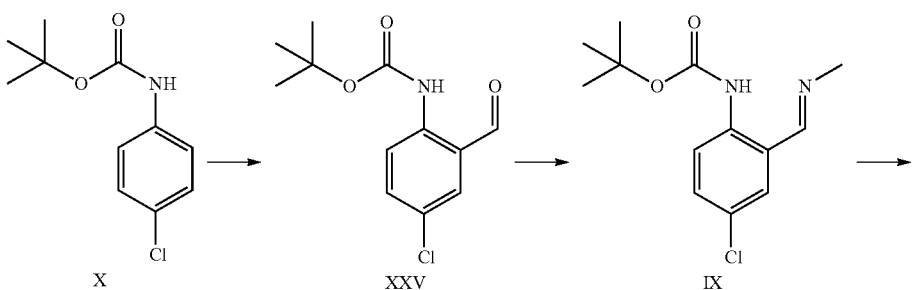

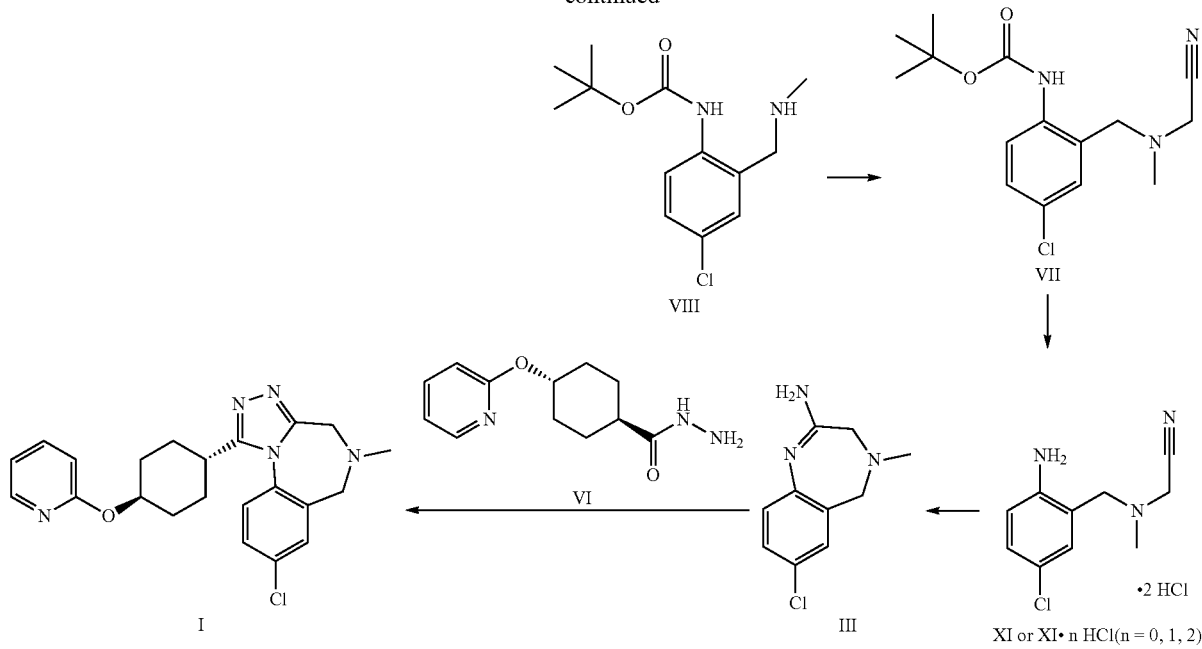

Aldehyde of formula XXV has been described in the art (Aubé et al.)[5] being prepared by ortho-lithiation with sec-butyl lithium (s-BuLi) at −78° C. then raising the temperature to −20° C. prior to quenching with DMF. The product was obtained in 54% yield after chromatography. Present reaction is performed at higher temperature (up to −30° C.) and with n-butyl lithium (n-BuLi) to obtain a higher yield of >80% yield without chromatography and after crystallization. The process described herein is much more efficient and scalable.

[5] Aubé et al, J. Org. Chem., Vol. 65, No. 3, 2000

A certain embodiment of the invention relates to the process to synthesize a compound of formula XXV from a compound of formula X, whereby the lithiation takes place in tetrahydrofuran (THF), 2-methyl-tetrahydrofuran (2-Me-THF) or methyl tert-butyl ether (MBTE), in particular THF and MBTE, most particular MTBE.

A certain embodiment of the invention relates to the process to synthesize a compound of formula XXV from a compound of formula X, whereby the lithiation takes place at −60° C. to −10° C., in particular between −40° C. and −20° C., most particular at −30±2° C.

A certain embodiment of the invention relates to the process to synthesize a compound of formula XXV from a compound of formula X, whereby the lithiation takes place in the presence of an additive like (but not limited to) tetramethylethylendiamine (TMEDA) or pentamethyldiethylenetriamine (PMDTA), in particular TMEDA.

A certain embodiment of the invention relates to the process to synthesize a compound of formula XXV from a compound of formula X, whereby the lithiation takes place with n-butyl lithium, n-hexyl lithium or s-butyl lithium, in particular n-butyl lithium.

A certain embodiment of the invention relates to the process to synthesize a compound of formula XXV from a compound of formula X, whereby the lithiation takes place with n-BuLi, in the presence of tetramethylethylendiamine (TMEDA) in MTBE and at −30±2° C.

Compound of formula XXV can be isolated as a crystalline intermediate and then converted in a second step to the imine of formula IX. The crystallization can be performed for example in ethanol or isopropanol.

Alternatively, the crude extract of compound XXV can be telescoped with the imine formation step by performing a solvent exchange to the target solvent followed by imine formation and isolation of compound of formula IX.

A certain embodiment of the invention relates to the process as described above comprising reacting a compound of formula XXV to a compound of formula IX, whereby imine formation is conducted in an alcohol like methanol, ethanol, isopropanol or n-propanol, in particular ethanol or methanol or mixture thereof.

The imine of formula IX is isolated as a crystalline intermediate by direct crystallization from the reaction mixture. It was gratifyingly found that the imine crystallization provides a very efficient purification point in the synthesis.

The imine of formula IX can be reduced by catalytic hydrogenation to provide the intermediate of formula VIII.

A certain embodiment of the invention relates to the process as described above comprising reacting a compound of formula IX to a compound of formula VIII whereby the reduction is performed with hydrogen in a the presence of a catalyst like Platinum on charcoal, in particular with hydrogen and Pt/C in methanol.

A certain embodiment of the invention relates to the process as described above comprising reacting a compound of formula IX to a compound of formula VIII whereby the reduction is performed with hydrogen over Pt/C at a temperature between 15° C. and 50° C., in particular between 20 and 30° C., most particular between 20 and 25° C.

A certain embodiment of the invention relates to the process as described above comprising reacting a compound of formula IX to a compound of formula VIII whereby the reduction is performed with hydrogen over Pt/C at a pressure between 1 and 10 bar, in particular at 5 bar.

A certain embodiment of the invention relates to the process as described above comprising reacting a compound of formula IX to a compound of formula VIII whereby the reduction is performed with hydrogen over Pt/C in methanol at a pressure of 5 bar and at room temperature.

Alternatively, the imine of formula IX can be reduced to the intermediate of formula VIII by the use of sodium borohydride.

Although the reduction does proceed in an aprotic solvent like THF in the presence of a carboxylic acid (acetic acid, caproic acid, 2-ethyl-hexanoic acid and pivalic acid, in particular acetic acid and pivalic acid), better results can be obtained in protic organic solvents like methanol or ethanol, in particular methanol.

Working in a homogenous reaction system like THF/methanol mixtures, and in the presence of methyl amine as additive minimizes the formation of the following 2 major byproducts dimer 1 and dimer 2.

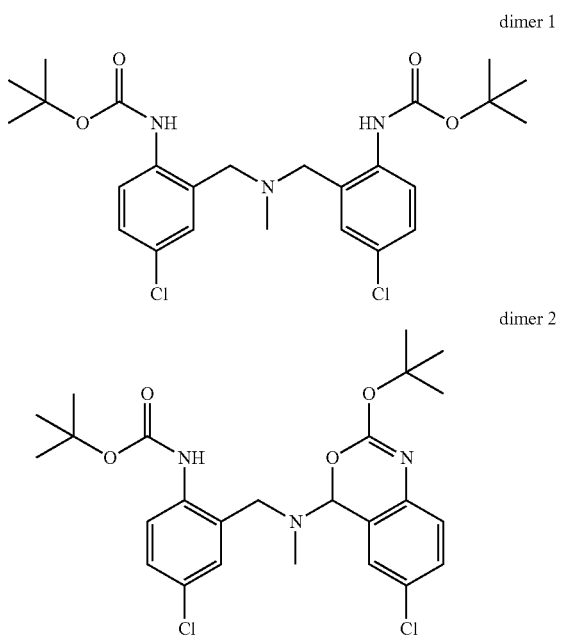

dimer 1 dimer 2

The homogenous system maximizes the concentration of the imine of formula IX in solution, hence increasing the rate of the productive reduction vs dimer formation. Due to the moderate to low solubility of the imine substrate in methanol, an additive like for example THF is used to provide a clear solution prior to the dosing of the reducing agent.

The presence of methyl amine competes with the product of formula VIII for the reaction with the imine substrate of formula IX hence decreasing the amount of side products dimer 1 and/or dimer 2.

A certain embodiment of the invention relates to the process as described above comprising reacting a compound of formula IX to a compound of formula VIII whereby the reduction is performed with sodium borohydride in a mixture of THF and methanol, in particular with enough methanol to ensure reactivity and enough THF to ensure solubility of the imine substrate.

A certain embodiment of the invention relates to the process as described above comprising reacting a compound of formula IX to a compound of formula VIII whereby the reduction is performed with sodium borohydride in methanol or a mixture of THF and methanol, in particular a mixture of THF and methanol, most particular in a 2:1 mixture of methanol and THF.

A certain embodiment of the invention relates to the process as described above comprising reacting a compound of formula IX to a compound of formula VIII whereby the reduction with sodium borohydride is conducted in the presence of a carboxylic acid like (but not limited to) acetic acid or pivalic acid, in particular acetic acid.

A certain embodiment of the invention relates to the process as described above comprising reacting a compound of formula IX to a compound of formula VIII whereby the reduction with sodium borohydride is conducted in the presence methyl amine. A certain embodiment of the invention relates to the process as described above comprising reacting a compound of formula IX to a compound of formula VIII whereby the reduction with sodium borohydride is conducted in a 2:1 methanol/THF mixture, in the presence of acetic acid and methyl amine.

A certain embodiment of the invention relates to the process comprising the reduction of the imine of formula IX to the intermediate of formula VIII whereby dimer 1 and dimer 2 are formed as by-products in amounts of <1%. The intermediate of formula VIII can be isolated by crystallization for example from a mixture of iPrOH and water or as a salt, for example its acetic acid salt.

Extraction of the crude product of formula VIII (from the sodium borohydride reduction) in the aqueous phase at acidic pH (for example but not limited to pH from 4-6), followed by a wash-out of the impurities with an organic solvent, followed by an extraction of the product in an organic solvent at neutral to basic pH gives a product of very high purity. The extract can then be introduced in the next step (alkylation) without the need of crystallization and drying steps.

A certain embodiment of the invention relates to the process as described above comprising reacting a compound of formula IX to a compound of formula VIII whereby the purification of the crude intermediate of formula is performed by an extractive work-up, in particular an acid extraction of the product in the aqueous phase, followed by a wash with an organic solvent, followed by extracting the product with an organic solvent at neutral to basic pH.

The alkylation of a compound of formula VIII to provide a compound of formula VII can be performed with chloro-, bromo-, or iodo-acetonitrile. The reactivity of the chloroacetonitrile can be enhanced by using a bromide or iodide source like for example potassium iodide or bromide.

A certain embodiment of the invention relates to the process as described above comprising reacting a compound of formula VIII to a compound of formula VII whereby the alkylation is performed with chloroacetonitrile, in particular with chloroacetonitrile in the presence of potassium iodide or potassium bromide, most particular with chloroacetonitrile in the presence of potassium iodide.

Although the alkylation can be performed in polar aprotic solvents like DMF, NMP, DMA or DMSO, alternative solvents are preferred for better waste stream processing. Suitable solvents are THF, 2-Me-THF, acetone, toluene, acetonitrile, or ethyl acetate. For kinetic reasons, acetonitrile, acetone and ethyl acetate are used in particular, more particularly ethyl acetate.

A certain embodiment of the invention relates to the process as described above comprising reacting a compound of formula VIII to a compound of formula VII whereby the alkylation is performed with chloroacetonitrile and potassium iodide, in acetone, acetonitrile or ethyl acetate, in particular in ethyl acetate. Ethyl acetate offers the additional advantage of allowing a direct extractive work-up without any solvent exchange prior to the extraction, or the use of an additional phase splitting solvent.

A certain embodiment of the invention relates to the process as described above comprising reacting a compound of formula VIII to a compound of formula VII whereby the alkylation is performed with chloroacetonitrile in the presence of a suitable base like sodium hydrogen carbonate, sodium carbonate, potassium hydrogen carbonate, sodium hydrogen carbonate, cesium hydrogen carbonate or cesium carbonate, in particular with sodium hydrogen carbonate or potassium hydrogen carbonate, most particularly with sodium hydrogen carbonate.

A certain embodiment of the invention relates to the process as described above comprising reacting a compound of formula VIII to a compound of formula VII whereby the alkylation is performed with chloroacetonitrile, in refluxing ethyl acetate, in the presence of potassium iodide and sodium hydrogen carbonate as base.

Product of formula VII can be isolated by crystallization for example in isopropanol or ethanol/water mixtures.

A certain embodiment of the invention relates to the process as described above comprising reacting a compound of formula VII to a compound of formula III, whereby the reaction takes place in the presence of excess HCl, in an alcohol like methanol, ethanol, trifluoroethanol, isopropanol, in particular isopropanol or trifluoroethanol, more particular isopropanol, or an alcohol/dichloromethane mixture, in particular trifluoroethanol/dichloromethane (for the use of trifluoroethanol as solvent for the preparation of amidines from nitrile see Caron et al.[6]).

Caron, L. Wei, J. Douville, A Ghosh, J. Org. Chem. 2010, 75, 945-947

A certain embodiment of the invention relates to the process as described above comprising reacting a compound of formula VII to a compound of formula III, whereby compound of formula VII is converted to compound of formula XI. 2 HCl which is not isolated but is in situ further converted to compound of formula III.

A certain embodiment of the invention relates to the process as described above comprising reacting a compound of formula VII to a compound of formula III, whereby an alkyl 2-[(2-amino-5-chloro-phenyl)methyl-methyl-amino] acetate, the corresponding imidate or othoester byproducts are formed, the RO fragment coming from the alcohol being used.

Compared to the use of linear alcohols like ethanol, the amount of these byproducts (III', III'', III''') is decreased by using less nucleophilic alcohols like isopropanol or trifluoroethanol. Isopropanol represents a greener and cheaper alternative to trifluoroethanol.

A certain embodiment of the invention relates to the process as described above comprising reacting a compound of formula VII to a compound of formula III, whereby the reaction takes place in the presence of excess HCl, in isopropanol.

A certain embodiment of the invention relates to the process as described above comprising reacting a compound of formula VII to a compound of formula III, whereby the starting material is dosed onto the solution upon which Boc deprotection to a compound of formula XI (as hydrochloride salt) occurs in a controlled manner allowing the control of the $CO_2$ off-gas.

A certain embodiment of the invention relates to the process to synthesize a compound of formula I further comprising reacting a compound of formula X to a compound of formula XI via the following steps:

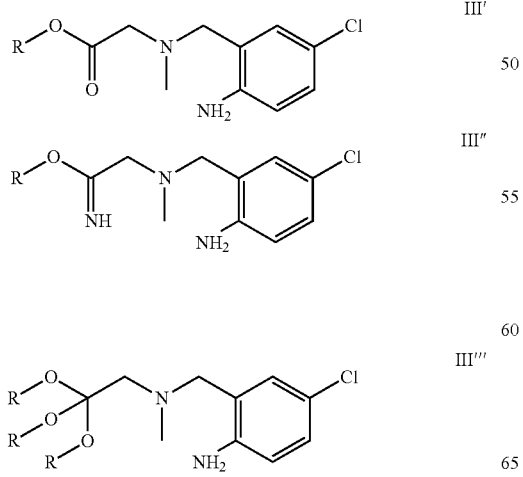

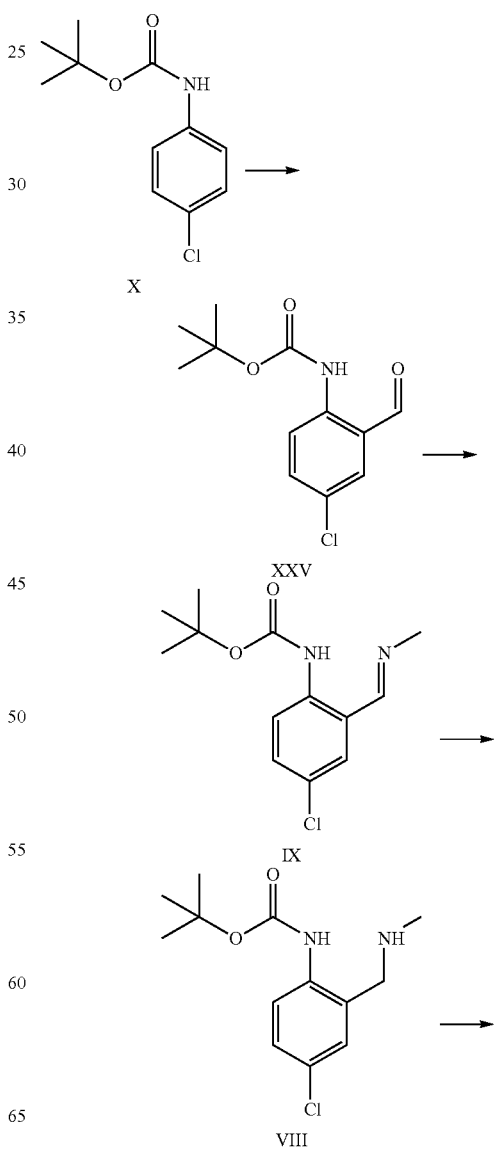

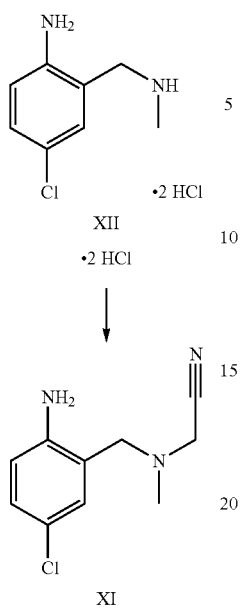
A certain embodiment of the invention relates to the process to synthesize a compound of formula I comprising the following steps:
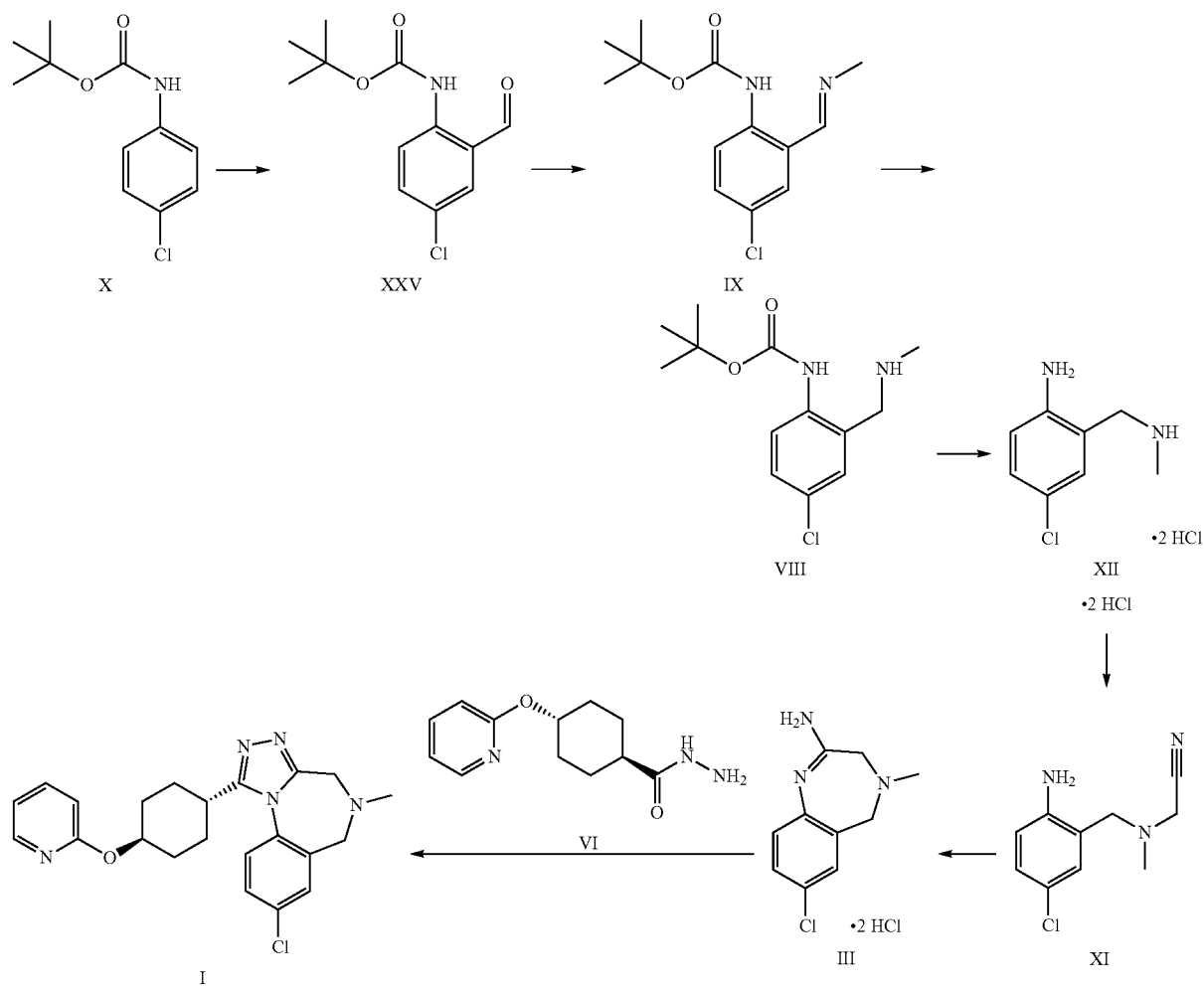

A certain embodiment of the invention relates to the process to synthesize a compound of formula I further comprising reacting a compound of formula XV to a compound of formula XI via the following steps:

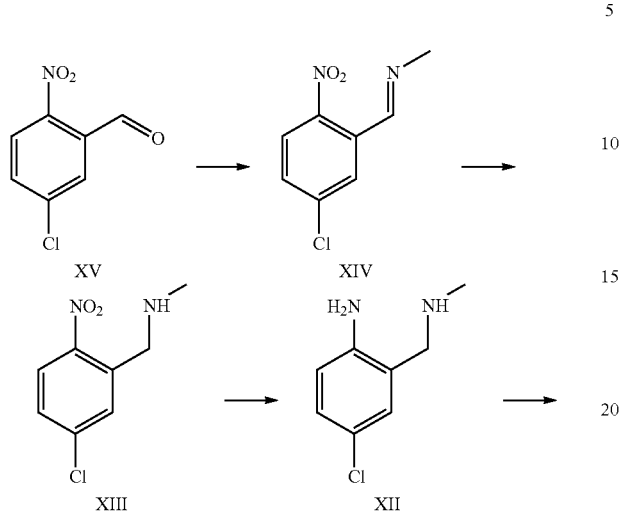

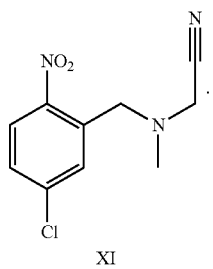

Compound of formula XII can also be isolated as a hydrochloride salt.

The transformation of compound of formula XV to compound of formula XII was adapted from WO2005/68466[7].

WO2005/68466

A certain embodiment of the invention relates to the process to synthesize a compound of formula I comprising the following steps:

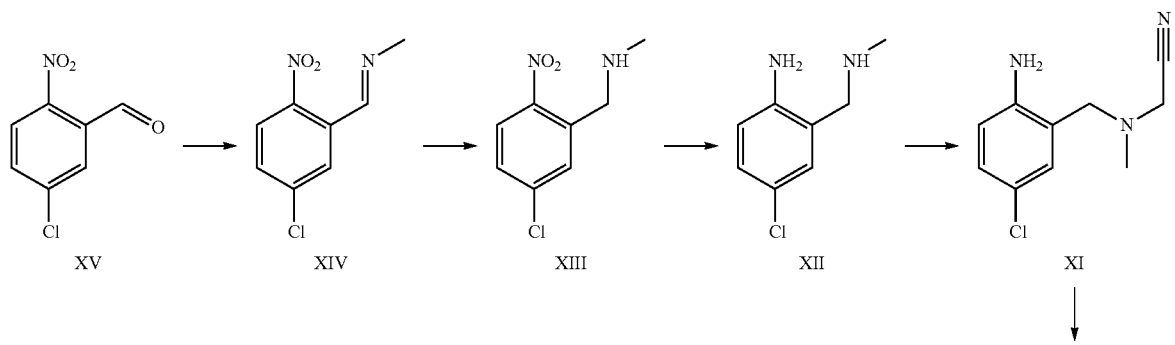

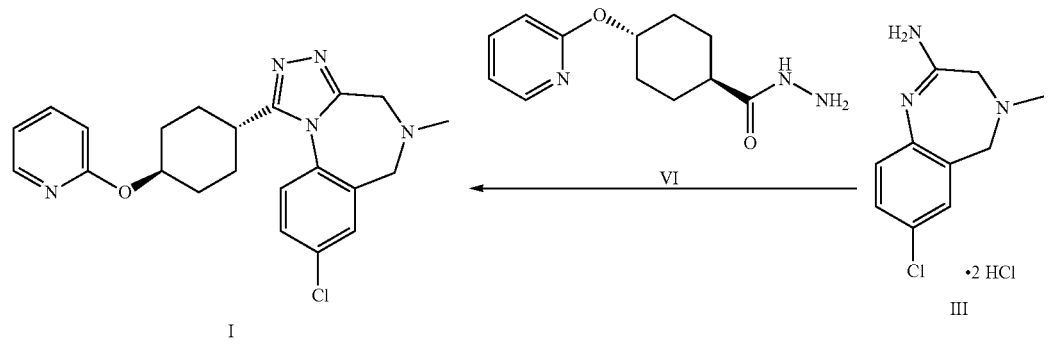

A certain embodiment of the invention relates to the process to synthesize a compound of formula I further comprising reacting a compound of formula XVI to a compound of formula XI via the following steps:

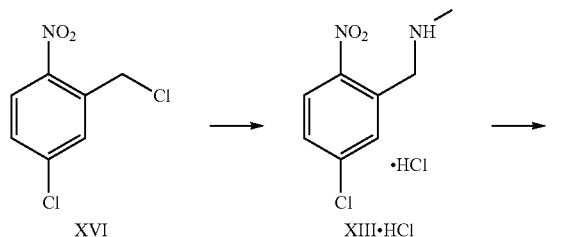

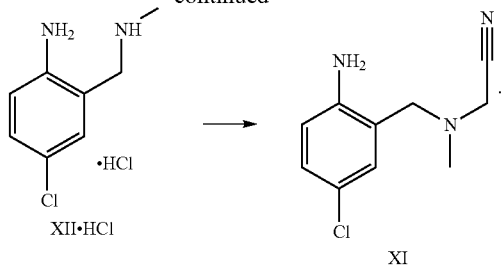

A certain embodiment of the invention relates to the process to synthesize a compound of formula I comprising the following steps:

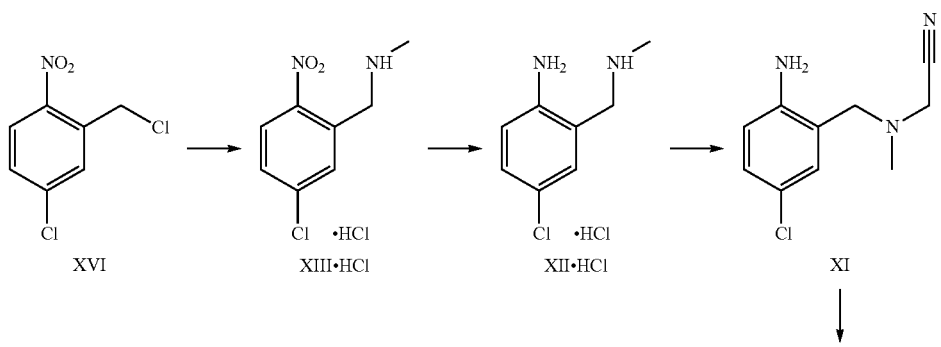

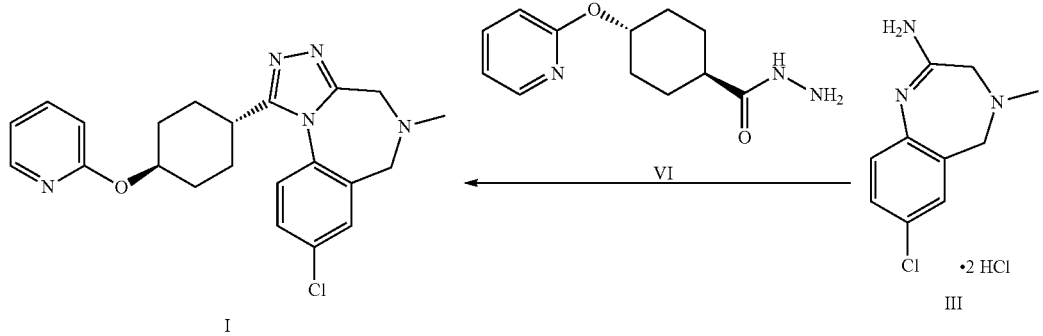

A certain embodiment of the invention relates to the synthesis of a compound of formula I comprising reacting a compound of formula XXVI to a compound of formula XI via the following steps

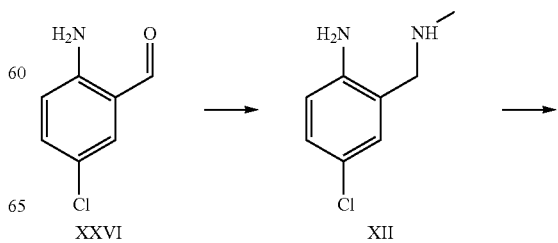

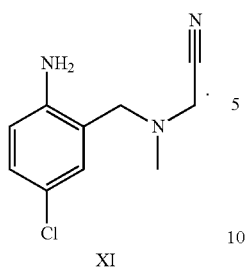

Compound of formula XII has been described in the art by Venkov et al.[8] as an intermediate which was not isolated and used directly in a subsequent reaction.

Venkov et al, Synthesis, 1990, 253

A certain embodiment of the invention relates to the process as described above comprising reacting a compound of formula XXVI to a compound of formula XII, whereby compound of formula XII is isolated from the reaction mixture.

A certain embodiment of the invention relates to the process as described above comprising reacting a compound of formula XXVI to a compound of formula XI, whereby the reductive amination and the alkylation step are conducted in one pot.

A certain embodiment of the invention relates to intermediate XI.

A certain embodiment of the invention relates to the process to synthesize a compound of formula I comprising the following steps:

A certain embodiment of the invention relates to a process to synthesize a compound of formula I as described herein, comprising the following steps:

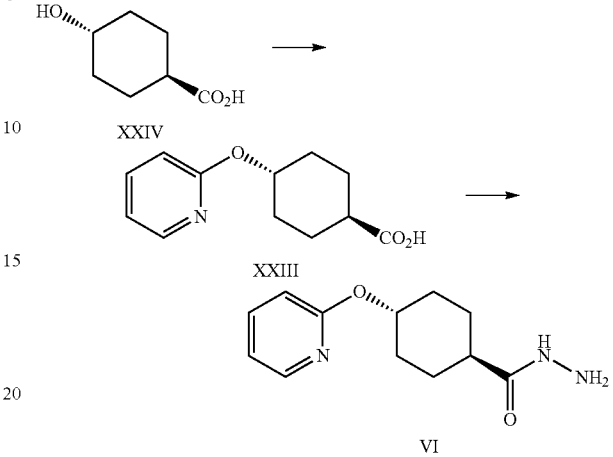

A certain embodiment of the invention relates to a process to synthesize a compound of formula I as described herein, comprising reacting a compound of formula XXIII to a compound of formula VI by aromatic nucleophilic substitution of a 2-halopyridine with 4-hydroxycyclohexanecarboxylic acid.

A certain embodiment of the invention relates to a process to synthesize a compound of formula I as described herein,

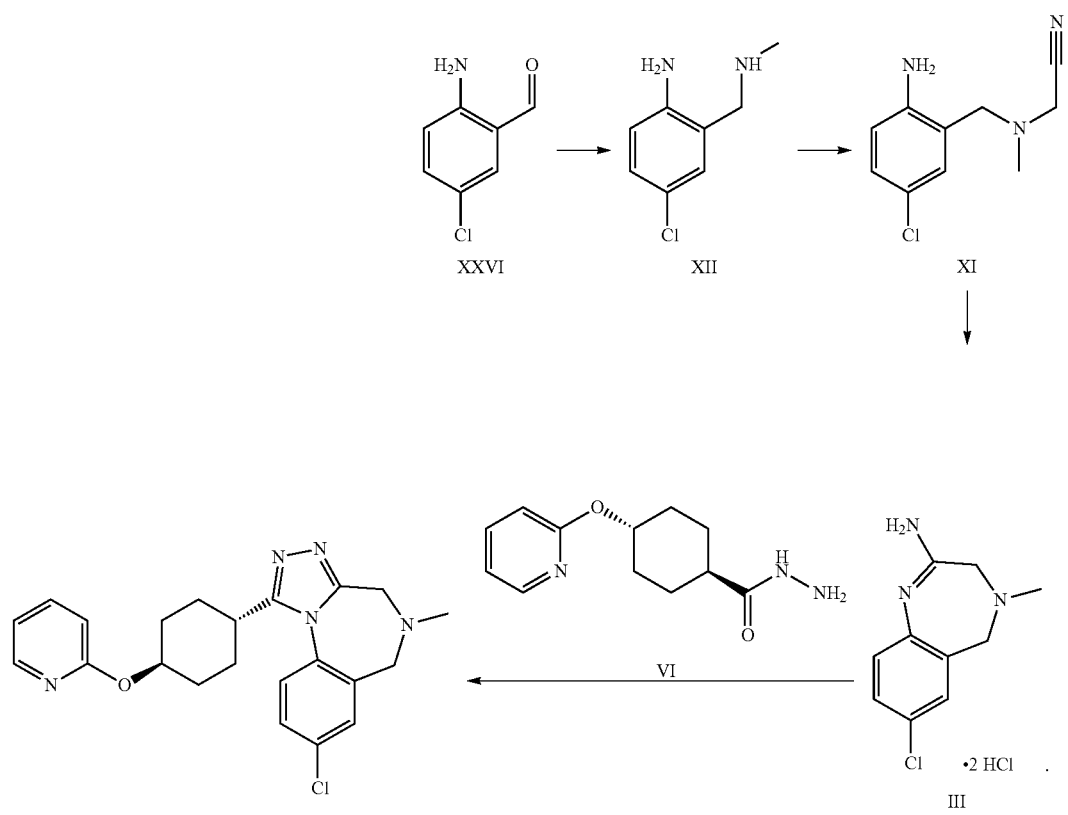

comprising reacting a compound of formula XXIV to a compound of formula XXIII, whereby bases like are sodium tert-amyl alcoholate (tAmONa), potassium tert-amyl alcoholate (tAmOK), sodium tert-butoxide (tBuONa), potassium tert-butoxide (tBuOK), in particular tAmONa can be used.

A certain embodiment of the invention relates to a process to synthesize a compound of formula I as described herein, comprising reacting a compound of formula XXIV to a compound of formula XXIII, whereby the solvent is N-methyl-2-pyrrolidone (NMP) or dimethylacetamide (DMA), in particular NMP.

A certain embodiment of the invention relates to a process to synthesize a compound of formula I as described herein, comprising reacting a compound of formula XXIV to a compound of formula XXIII, whereby the reaction is performed at 80-120° C., in particular at 88-92° C.

A certain embodiment of the invention relates to a process to synthesize a compound of formula I as described herein, comprising reacting a compound of formula XXIV to a compound of formula XXIII, whereby the 2-halopyridines are selected from 2-fluoropyridine and 2-chloropyridine, in particular 2-chloropyridine.

A certain embodiment of the invention relates to a process to synthesize a compound of formula I as described herein, comprising reacting a compound of formula XXIV to a compound of formula XXIII, whereby compound of formula XXIV is reacted with 2-chloropyridine, in NMP, in the presence of sodium tert-amyloxide at 85-95° C.

A certain embodiment of the invention relates to a process to synthesize a compound of formula I as described herein, comprising reacting a compound of formula XXIII to a compound of formula VI, whereby XXIII is activated by reaction with a suitable alkyl chloroformate like isobutyl-, ethyl or methyl chloroformate, in particular isobutyl chloroformate.

A certain embodiment of the invention relates to a process to synthesize a compound of formula I as described herein, comprising reacting a compound of formula XXIII to a compound of formula VI, whereby XXIII is activated with a suitable alkyl chloroformate in the presence of a suitable base like triethylamine, Hünig's base, pyridine, collidine or N-methylmorpholine, in particular N-methylmorpholine.

A certain embodiment of the invention relates to a process to synthesize a compound of formula I as described herein, comprising reacting a compound of formula XXIII to a compound of formula VI, whereby XXIII is activated with carbonyldimimidazole (CDI) to give the corresponding acyl imidazole intermediate which is further reacted with hydrazine.

A certain embodiment of the invention relates to a process to synthesize a compound of formula I as described herein, comprising reacting a compound of formula XXIII to a compound of formula VI, whereby the reaction takes place in a suitable solvent like DMF, NMP, THF, 2-MeTHF, in particular THF.

A certain embodiment of the invention relates to a process to synthesize a compound of formula I as described herein, comprising reacting a compound of formula XXIII to a compound of formula VI, whereby the activation with CDI is performed at 10° C. to 50° C., in particular between 20° C. and 30° C., more particular at 25° C.

A certain embodiment of the invention relates to a process to synthesize a compound of formula I as described herein, comprising reacting a compound of formula XXIII to a compound of formula VI, whereby the acyl imidazole intermediate is then reacted with hydrazine, in particular excess hydrazine is used, most particular at least 2 time the excess of CDI used in the activation step.

A certain embodiment of the invention relates to a process to synthesize a compound of formula I as described herein, comprising reacting a compound of formula XXIII to a compound of formula VI, whereby the order of addition involves the addition of the activated acid to hydrazine.

A certain embodiment of the invention relates to a process to synthesize a compound of formula I as described herein, comprising reacting a compound of formula XXIII to a compound of formula VI, whereby the acyl imidazole reaction mixture can be degassed after the activation and prior to the reaction with hydrazine to remove the solubilized $CO_2$.

A certain embodiment of the invention relates to a process to synthesize a compound of formula I as described herein, comprising reacting a compound of formula XXIII to a compound of formula VI, whereby 4-(2-pyridyloxy)-N'-[4-(2-pyridyloxy) cyclohexanecarbonyl]cyclohexane-carbohydrazide (VI') is formed as byproduct.

A certain embodiment of the invention relates to a process to synthesize a compound of formula I, comprising the following steps:

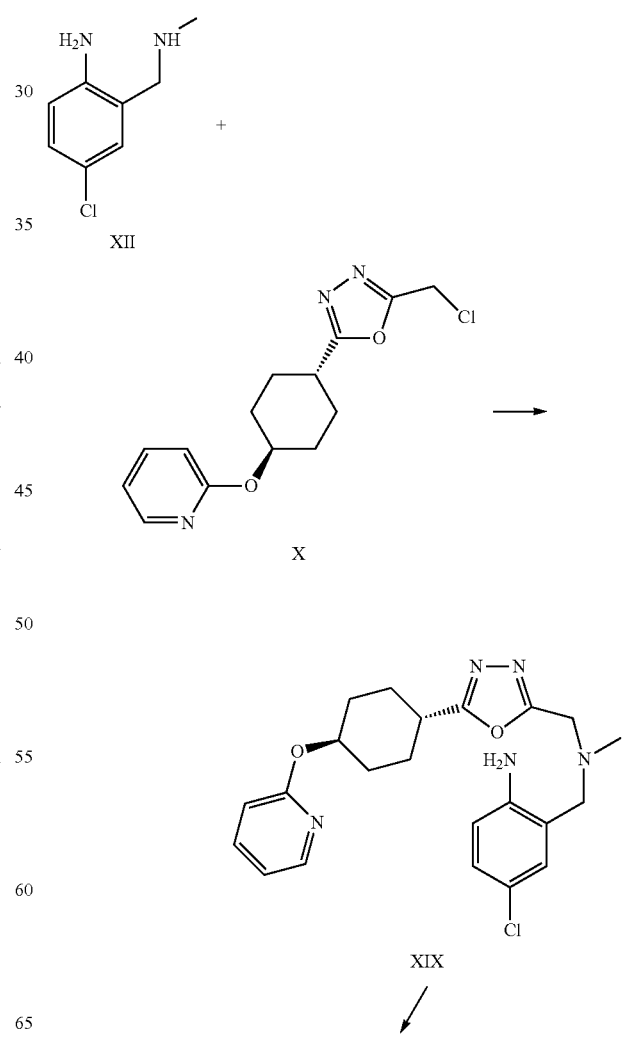

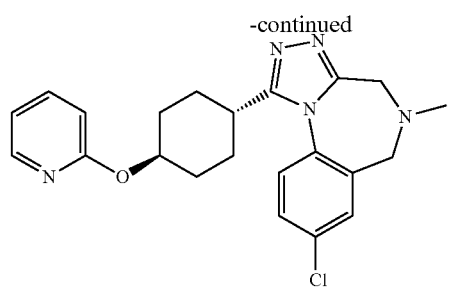
I
Certain oxadiazole precursors have been described in the art[9].
WO2004074291, WO2005068466 and WO2006021882
A certain embodiment of the invention relates to a process to synthesize a compound of formula I as described herein, comprising the following steps:
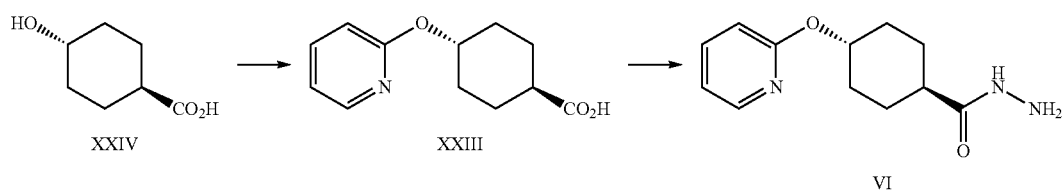
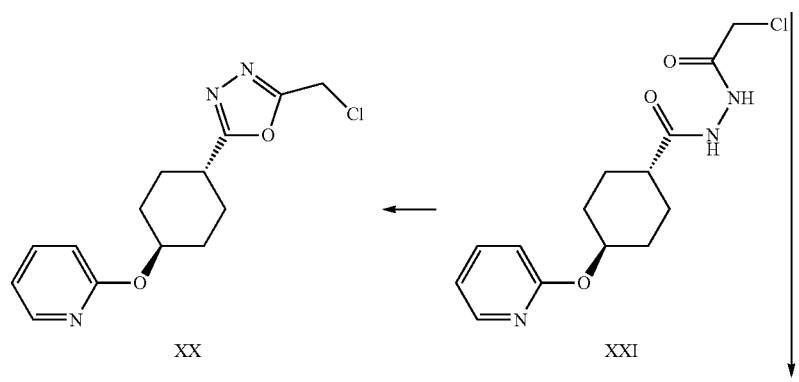
A certain embodiment of the invention relates to the process to synthesize a compound of formula I comprising the following steps:
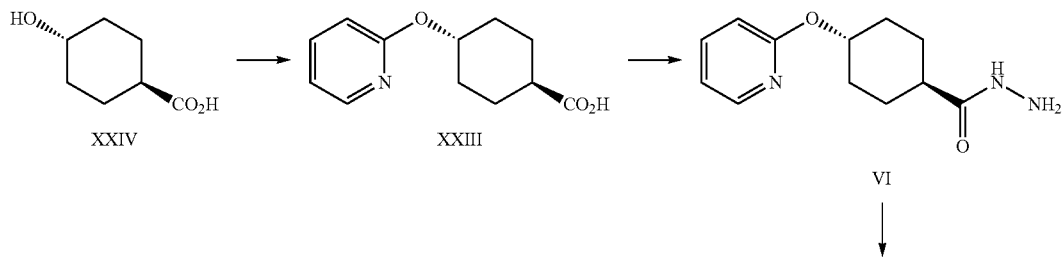

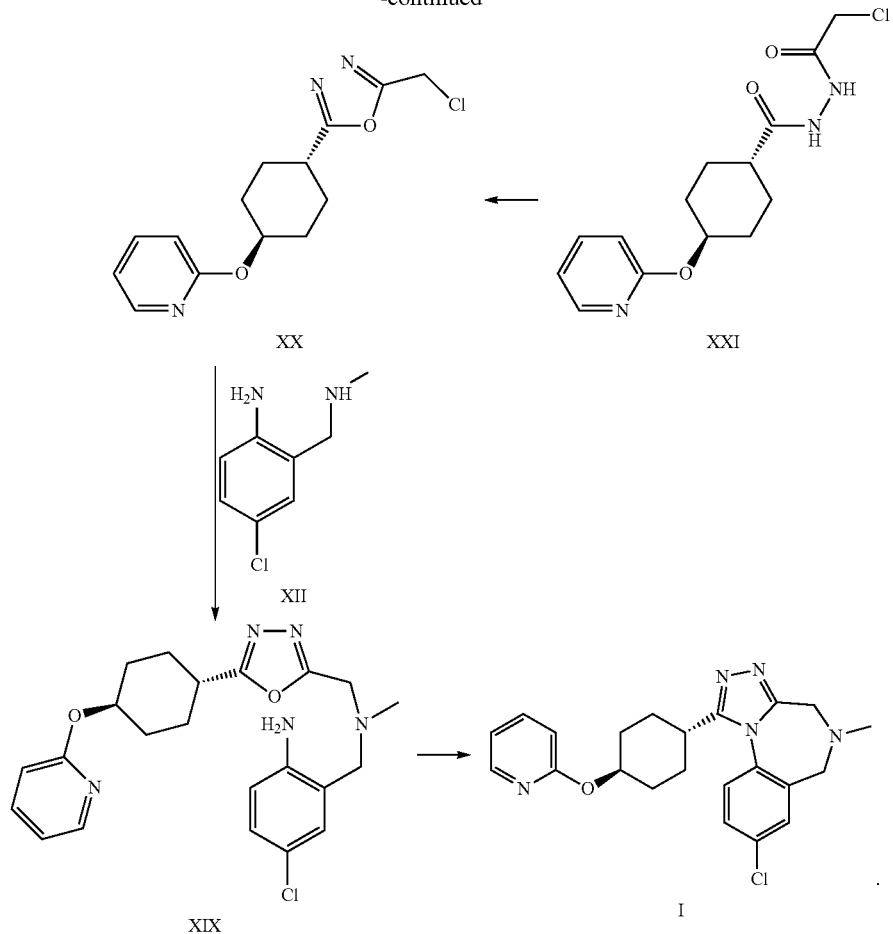

A certain embodiment of the invention relates to the process to synthesize a compound of formula I, whereby a compound of formula INT, a tautomer or a salt thereof, is formed as intermediate:

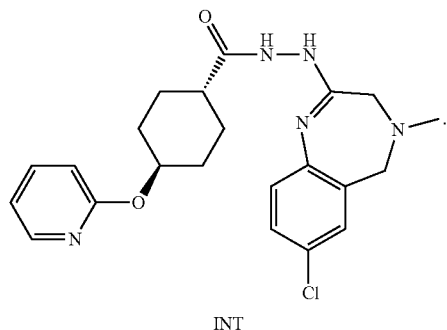 [SMILES: CN1CC(NNC(=O)[C@H]2CC[C@H](Oc3ccccn3)CC2)=Nc2ccc(Cl)cc2C1 ; "INT"]

INT

A certain embodiment of the invention relates to the intermediate compound INT, a tautomer or a salt thereof. A certain embodiment of the invention relates to the intermediate compound INT.

A certain embodiment of the invention relates to the process to synthesize a compound of formula I, whereby a compound of formula III is formed as intermediate.

A certain embodiment of the invention relates to the intermediate compound II, a tautomer or a salt thereof:

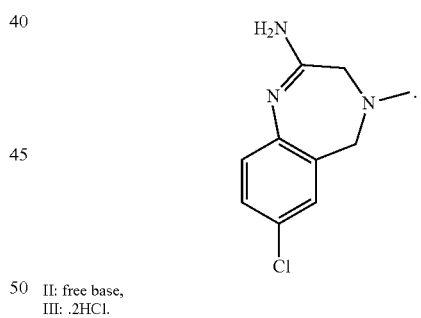

II: free base,
III: .2HCl.

A certain embodiment of the invention relates to the intermediate compound II, or a salt thereof.

A certain embodiment of the invention relates to the intermediate compound III.

A certain embodiment of the invention relates to a process to synthesize a compound of formula VI.

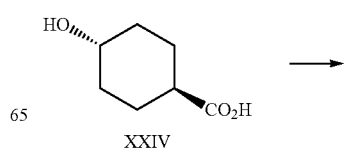

XXIV

A certain embodiment of the invention relates to a compound of formula I as described herein for use in the therapeutic and/or preventive treatment of inappropriate secretion of vasopressin, anxiety, depressive disorders, obsessive compulsive disorder, autistic spectrum disorders, schizophrenia, aggressive behavior and phase shift sleep disorders, in particular jetlag.

BRIEF DESCRIPTION OF THE FIGURES

The FTIR data has been collected as a Nujol mull so additional peaks due to the mineral oil dispersing agent are visible in the IR spectra.

FIG. 1: XRPD pattern of form A.
FIG. 2: IR spectrum of form A.
FIG. 3: Raman spectrum of form A.
FIG. 4: XRPD pattern of form B.
FIG. 5: IR spectrum of form B.
FIG. 6: Raman spectrum of form B.
FIG. 7: XRPD pattern of form C.
FIG. 8: IR spectrum of form C.
FIG. 9: Raman spectrum of form C.
FIG. 10: XRPD pattern of form D.
FIG. 11: IR spectrum of form D.
FIG. 12: Raman spectrum of form D.
FIG. 13: XRPD pattern of form E.
FIG. 14: IR spectrum of form E.
FIG. 15: Raman spectrum of form E.
FIG. 16: XRPD pattern of form F.
FIG. 17: IR spectrum of form F.
FIG. 18: Raman spectrum of form F.
FIG. 19: XRPD pattern of form G.
FIG. 20: IR spectrum of form G.
FIG. 21: Raman spectrum of form G.
FIG. 22: XRPD pattern of form H.
FIG. 23: Raman spectrum of form H.

EXPERIMENTAL PART

The following experiments are provided for illustration of the invention. They should not be considered as limiting the scope of the invention, but merely as being representative thereof.

Form A of I 100 mg of I were dissolved in a closed vial, at 22° C., in 5.0 mL of a mixture of ethanol/water 1:1 (v/v). After dissolution, the solution was filtered with a 0.45 μm filter unit. Subsequently, the clear solution was allowed to evaporate at 22° C. for 10 days. After complete evaporation the product was dried (50° C./<20 mbar for >24 h) and analyzed.

Form B of I 100 mg of I were dissolved in a closed vial, at 22° C., in 3.0 mL of ethyl acetate. After dissolution, the solution was filtered with a 0.45 μm filter unit. Subsequently, the clear solution was allowed to evaporate at 22° C. for 10 days. The experiment led to single crystals of form B suitable for single crystal structure analysis. After complete evaporation the product was dried (50° C./<20 mbar for >24 h) and analyzed.

Form C of I 100 mg of I were dissolved in a closed vial, at 22° C., in 1.4 mL of a mixture of water saturated butanol (ca. 20% v/v). After dissolution, the solution was filtered with a 0.45 μm filter unit. Subsequently, the clear solution was allowed to evaporate at 22° C. for 1 month. The experiment led to single crystals of form C suitable for single crystal structure A certain embodiment of the invention relates to the process to synthesize a compound of formula I comprising the following steps:

A certain embodiment of the invention relates to a compound of formula I or a pharmaceutically acceptable salt, whenever prepared by a process as described herein.

A certain embodiment of the invention relates to a compound of formula I as described herein for use as a medicament.

analysis. After complete evaporation the product was dried (50° C./<20 mbar for >24 h) and analyzed.

Form D (p-Xylene Hemi-Solvate) of I 100 mg of I were suspended in a closed vial, at 22° C., in 0.35 mL of p-xylene and allowed to agitate at 60° C. After 14 days equilibration at 60° C., the slurry was filtered and the product dried (50° C./<20 mbar for >24 h) and analyzed. The evaporation of the filtrate (3 days at 22° C.) led to single crystals of form D suitable for single crystal structure analysis.

Form E (Acetic Acid Hemi-Solvate) of I 100 mg of I were dissolved in a closed vial, at 22° C., in 0.4 mL of acetic acid. After dissolution, the solution was filtered with a 0.45 μm filter unit. Subsequently, the clear solution was allowed to evaporate at 22° C. for 14 days. The experiment led to an oily residuum which transform in to a powder after scraping with a spattel. The product was dried (50° C./<20 mbar for >24 h) and analyzed.

Form F of I 100 mg of Form B were suspended in a closed vial, at 22° C., in 0.3 mL of isopropanol and allowed to agitate at 22° C. After 1 day agitation, 10 mg of API/form C were added and the slurry still agitates at 22° C. After 14 days equilibration at 22° C., the slurry was filtered and the product dried (50° C./<20 mbar for >24 h) and analyzed.

Form G (Butyronitrile Solvate) of I 100 mg of I were dissolved in a closed vial, at 22° C., in 1.5 mL of butyronitrile. Immediately after dissolution, the solution began, under agitation, to precipitate. The slurry was allowed, still under agitation, to partially evaporate at 22° C. for 10 days. After partially evaporation (ca. 50%), the slurry was filtered and the product dried (50° C./<20 mbar for >24 h) and analyzed. The evaporation of the filtrate (2 weeks at 22° C.) led to single crystals of form G suitable for single crystal structure analysis.

Form H (Trihydrate) of I 100 mg of I were dissolved in 1.9 mL of a mixture of ethanol/water 1:1 (v/v) at 65° C. in a closed vial. The clear solution was linearly cooled from 65° C. to −20° C. within 8 h without agitation. The experiment led to single crystals of form H suitable for single crystal structure analysis. The product was isolated by removing the mother liquor with a pipette and analyzed in wet stage.

tert-Butyl N-(4-chloro-2-formyl-phenyl)carbamate XXV

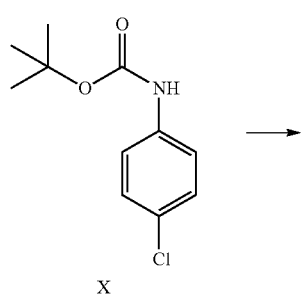

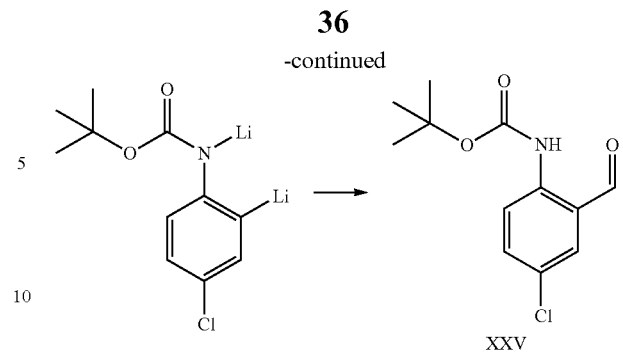

tert-Butyl 4-chlorophenylcarbamate (40 g, 175 mmol, Eq: 1.00) was dissolved in THF (248 g, 280 mL). The solution was cooled to −30° C. N,N,N',N'-tetramethylethylenediamine (44.5 g, 57.8 mL, 379 mmol, Eq: 2.17) was added dropwise. After 5 min, n-butyllithium 2.5 M in hexanes (210 mL, 524 mmol, Eq: 3.00) was added dropwise over 60 min at −30° C. to −20° C. After 5 h at −30°, DMF (38.4 g, 40.5 mL, 524 mmol, Eq: 3.00) were added over 35 min. After 1 h at −30° C., cold (0-5° C.) methyl t-butyl ether (MTBE) (207 g, 280 mL) was added (0° C.). 25% aqueous hydrogen chloride (HCl) (178 g, 149 mL, 1.22 mol, Eq: 7.0) was added over 30 min at −30° to 0° C. The aqueous phase was separated and extracted with MTBE (74.0 g, 100 mL). The organic phases were washed sequentially with 10% aqueous sodium chloride (NaCl) (100 mL), 5% aqueous sodium hydrogen carbonate (NaHCO₃) (100 mL) and half saturated aqueous NaCl (100 mL). The organic phases were combined, dried over magnesium sulfate (MgSO₄) and concentrated under reduced pressure (40° C./down to 10 mbar) to give 45.2 g of crude product. The crude product was dissolved in 2-propanol (157 g, 200 mL) at 80° C. The clear solution was slowly cooled to 0° C. during which product started to crystallize. The suspension was stirred 1 h at 0° C. and was filtered. The filter cake was washed with cold (0-5° C.) 2-propanol (15.7 g, 20 mL) dried at 50° C./10 mbar to give 38.8 g of title compound.

tert-Butyl N-[4-chloro-2-[(E)-methyliminomethyl]phenyl]carbamate IX

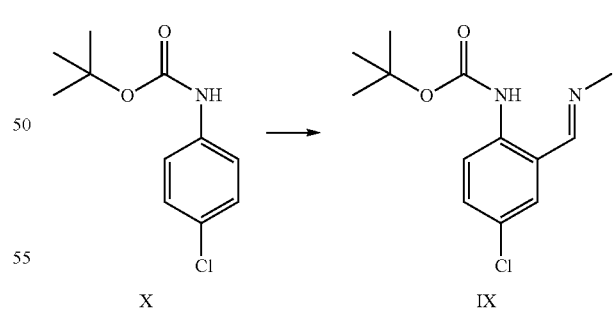

MTBE Process

N-Boc-4-chloroaniline (121 g, 531 mmol, Eq: 1.00) was dissolved in MTBE (648 g, 875 mL). The solution was cooled to −25° C. TMEDA (72 g, 92.9 mL, 620 mmol, Eq: 1.17) was added. 2.5 M n-Butyllithium (BuLi) in hexanes (398 g, 572 mL, 1.43 mol, Eq: 2.69) was added over 70 min, keeping the temperature below −20° C. After 2.5 h, dimethylformamide (DMF) (113 g, 120 mL, 1.55 mol, Eq: 2.91) was added over 30-45 min, keeping the temperature between −30° C. and −20° C. After 1 h, 25% aqueous HCl (526 g, 470 mL, 3.61 mol, Eq: 6.79) was added at a rate that the internal temperature is kept between −30° C. and 0° C. The reaction mixture was warmed up to room temperature (RT) over 30 min. The aqueous phase was separated and extracted with MTBE (333 g, 450 mL). The organic phases were combined and washed sequentially with saturated aqueous NaCl (600 mL), 10% aqueous NaHCO₃ (600 mL) and aqueous NaCl (600 mL). The organic phase was concentrated to circa 550 mL and the MTBE was solvent exchanged to ethanol (EtOH) at constant volume (Tj max 55° C.). The crude aldehyde suspension was diluted with EtOH (250 mL). 33% Methylamine in EtOH (150 g, 1.59 mol, Eq: 3) was added and the reaction mixture was stirred for >2 h at 25° C. (until <2% aldehyde are left, IPC). If required, the reaction mixture is seeded at 20° C. The resulting suspension was cooled over 1 h to −10° C. After 3 h at −10° C., the suspension was filtered. The filter cake was washed with cold (circa −10° C.) EtOH and was dried at 60° C./5 mbar to give 109 g of title compound as light yellow crystals.

THF Process

Alternatively, tert-butyl 4-chlorophenylcarbamate (120 g, 511 mmol, Eq: 1.00) was dissolved in tetrahydrofuran (THF) (745 g, 840 mL). The solution was cooled to −30° C. N,N,N',N'-tetramethylethylenediamine (129 g, 168 mL, 1.1 mol, Eq: 2.15) was added. N-Butyllithium 2.5 M in hexanes (613 mL, 1.53 mol, Eq: 3.00) was added over 60 min between −30° C. and −20° C. After 5 h at −30° C., DMF (112 g, 118 mL, 1.53 mol, Eq: 3.00) was added over 45 min between −30° and −20° C. 25% HCl (522 g, 435 mL, 3.58 mol, Eq: 7.0) was added over 30 min at −30° C. to 0° C. (pH 4-5). The aqueous phase was separated and extracted with a mixture of THF (106 g, 120 mL) and hexanes (79.1 g, 120 mL). The organic phases were washed sequentially with half saturated aqueous NaCl (240 mL), 5% aqueous NaHCO₃ (240 mL) and half saturated aqueous NaCl (240 mL). The organic phases were combined and concentrated to circa 300 mL and split in two.

Part 1 was diluted with THF (887 g, 1 L) and azeotroped at 45° C./400 mbar. The solution was solvent exchanged to methanol to give 285 g of a yellow suspension (residual water: 0.14%). 9.8 M Methylamine in methanol (36.5 mL, 358 mmol, Eq: 1.4 relative to theoretical aldehyde content) were added. A clear yellow solution was obtained. After 15 min the imine started to crystallize (in case no spontaneous crystallization is observed, seeding is performed). After 2 h at 20-25° C. the suspension was stirred for 1 h at 40° C., cooled to −10° C. for 1 h and filtered. The filter cake was washed with cold (−10° C.) methanol (47.5 g, 60 mL) and dried at 40° C. under reduced pressure to give 57 g of the title compound as a light yellow powder.

Part 2 was azeotroped and solvent exchanged to ethanol at 45° C./200 mbar to give 281 g of a yellow suspension (water: <0.1%). 9.8 M Methylamine in methanol (36.5 mL, 358 mmol, Eq: 1.4 to theoretical aldehyde content) was added at RT. After 4 h at RT and 1 h at −10° C., the suspension was filtered. The filter cake was washed with cold (−10° C.) ethanol (47.4 g, 60 mL) and was dried at 40° C. under reduced pressure to give 51.5 g of the title compound as a yellow powder.

tert-Butyl N-[4-chloro-2-[(E)-methyliminomethyl]phenyl]carbamate IX

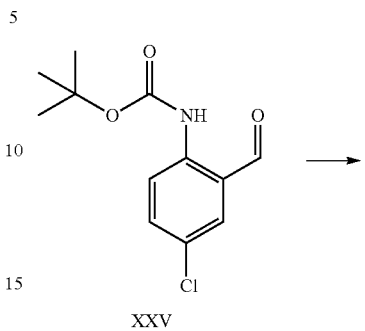

XXV

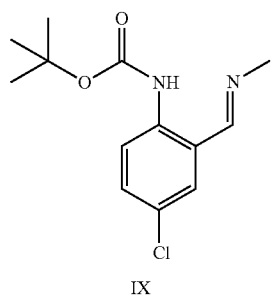

IX tert-Butyl 4-chloro-2-formylphenylcarbamate (38 g, 149 mmol, Eq: 1.00) was suspended in methanol (195 g, 247 mL). 9.8 M methylamine solution in methanol (21.2 mL, 208 mmol, Eq: 1.40) was added over 30 min at RT. The reaction mixture was stirred 1 h and the resulting solution was cooled to −10° C. (at circa 0° C. the product started to crystallized spontaneously). After 2 h at −10° C., the suspension was filtered. The filter cake was washed with cold (−10° C.) methanol (15.0 g, 19.0 mL) and dried under reduced pressure (10 mbar/50° C. to give) 36.4 g of the title compound as a white crystalline powder.

tert-Butyl N-[4-chloro-2-(methylaminomethyl)phenyl]carbamate VIII

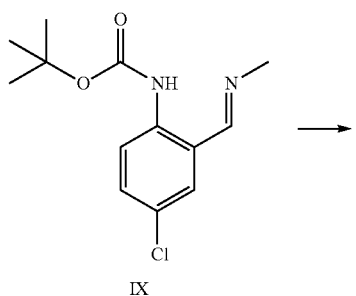

IX

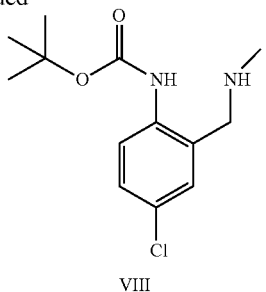

VIII tert-Butyl N-[4-chloro-2-[(E)-methyliminomethyl]phenyl]carbamate (50 g, 184 mmol, Eq: 1.00) was dissolved in a mixture of methanol (253 g, 320 mL) and THF (142 g, 160 mL). The solution was cooled to RT. 40% Methylamine in methanol (MeOH) (14.4 g, 185 mmol, Eq: 1.01) was added followed by acetic acid (AcOH) (22.0 g, 21.0 mL, 365 mmol, Eq: 1.98). Venpure 20-20 (sodium borohydride (NaBH$_4$) 20%/sodium hydroxide (NaOH) 20% in water, 35 g, 28.8 mL, 185 mmol, Eq: 1.00) was added at 0° C. for 45-60 min. After 30 min, acetone (21.4 g, 27.0 mL, 366 mmol, Eq: 1.99) was added over 30 min at 0° C. After >0.5 h at 0° C., the reaction mixture was added to a mixture consisting of 5% aqueous Na$_2$CO$_3$ (500 mL), half saturated aqueous NaCl (125 mL) and MTBE (370 g, 500 mL). The organic phase was separated and washed with 10% aqueous NaCl (210 g, 200 mL). The organic phase was extracted twice with a mixture consisting of 9 mL formic acid in 0.5 L water. The aqueous phases were combined and washed twice with MTBE (370 g, 500 mL). The organic phases were discarded. MTBE (0.5 L) was added and the pH was adjusted to 12-13 by addition of 32% aqueous NaOH (41.9 g, 31 mL, 335 mmol, Eq: 1.82). The aqueous phase was separated and extracted with MTBE (250 mL). The organic phases were combined and washed with saturated aqueous NaHCO$_3$ (209 g, 200 mL) and 10% aqueous NaCl (210 g, 200 mL) (pH: 7-8). The crude product solution was concentrated to circa half the volume (KFT<0.5% water). The crude product mixture was filtered to remove salts. The solution was concentrated under reduced pressure to give 51 g of crude product (>99.5 a % by high-performance liquid chromatography (HPLC), contains circa 8% residual MTBE). The crude product solution is solvent exchanged to ethyl acetate (AcOEt) and introduced in the next step without further purification.

The product can be crystallized from isopropanol (iPrOH)/water:

1.0 g tert-Butyl N-[4-chloro-2-(methylaminomethyl)phenyl]carbamate was dissolved at 40° C. in 2-propanol (3.92 g, 5 mL). The clear solution was cooled to RT and water (3.00 g, 3 mL) was added. The solution was seeded (crude, dried product did slowly crystallize upon standing providing the first seed crystals) and the crystallization started slowly. After 30 min, water (7.00 g, 7 mL) was added dropwise over 10 min. The white suspension was stirred 1 h at RT and filtered. The filter cake was washed with water and dried at 40° C./5 mbar to give 1 g of product as white crystals.

Alternatively, tert-butyl N-[4-chloro-2-[(E)-methyliminomethyl]phenyl]carbamate (2 g, 7.29 mmol, Eq.: 1) was suspended in methanol (20 mL). Pt/C 5% (185 mg) was added, the mixture was pressurized with hydrogen (5 bar) and stirred at RT. After completion of the reaction, the catalyst was filtered and the solution was concentrated under reduced pressure to give 1.85 g of crude tert-butyl N-[4-chloro-2-(methylaminomethyl)-phenyl]carbamate. The title compound can be crystallized as described above.

tert-Butyl N-[4-chloro-2-[[cyanomethyl(methyl)amino]methyl]phenyl]carbamate VII

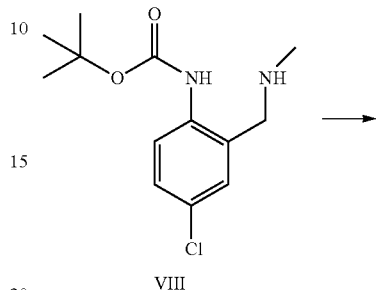

VIII

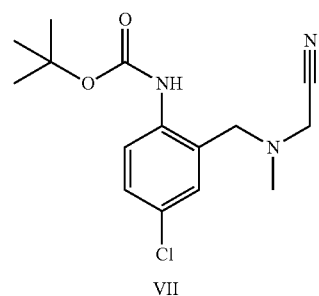

VII tert-Butyl N-[4-chloro-2-(methylaminomethyl)phenyl]carbamate (49.9 g, 184 mmol, Eq: 1.00) was dissolved in AcOEt (226 g, 250 mL). Sodium hydrogen carbonate (16.6 g, 198 mmol, Eq: 1.07) and potassium iodide (KI) (6 g, 36.0 mmol, Eq: 0.196) were added in one portion. 2-chloroacetonitrile (15.4 g, 13.0 mL, 200 mmol, Eq: 1.09) was added in one portion and the reaction mixture was heated at reflux for 15 h (<2% starting material). The reaction mixture was cooled to RT. 10% Aqueous NaCl (262 g, 250 mL) was added. The organic phase was separated and washed with half saturated aqueous NaHCO$_3$ (261 g, 250 mL). The organic phase was stirred overnight together with 10% aqueous sodium thiosulfate (291 g, 250 mL, 184 mmol, Eq: 1.00) and tetrabutylamonium chloride (1 g, 3.6 mmol, Eq: 0.02). The organic phase was separated and washed with 10% aqueous NaCl (262 g, 250 mL). The organic phase was concentrated to circa half the volume and was filtered. The volume was adjusted to circa 200 mL with EtOH and the solution was solvent exchanged to EtOH at constant volume. The solution was cooled to circa 28-30° C. and was seeded. After 30 min, the suspension was cooled to RT and water (40 mL) was added dropwise. The suspension was stirred overnight at RT and 2 h at 0-5° C. The suspension was filtered. The filter cake was washed with EtOH/water 1:1 (100 mL) and was dried at 60° C./5 mbar to give 46.8 g of title compound as white crystals.

41 tert-Butyl N-[4-chloro-2-[[cyanomethyl(methyl)amino]methyl]phenyl]carbamate VI

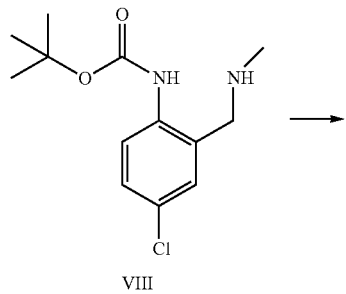

VIII

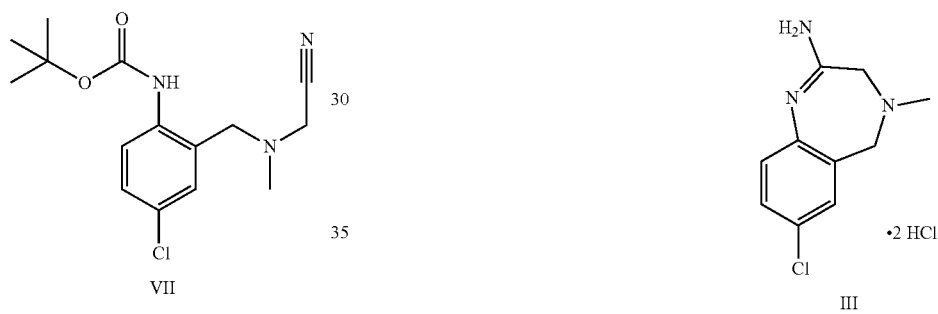

VII

42

7-Chloro-4-methyl-3,5-dihydro-1,4-benzodiazepin-2-amine dihydrochloride III

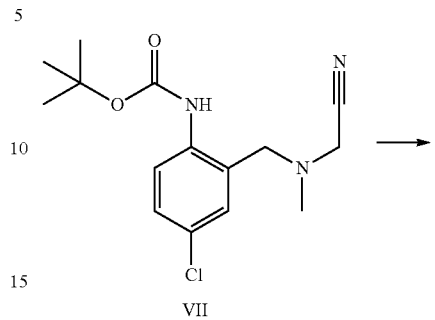

VII

III tert-Butyl 4-chloro-2-((methylamino)methyl)phenylcarbamate (9.0 g, 31.6 mmol, Eq: 1.00) was dissolved in ethyl acetate (40.6 g, 45.0 mL). Sodium bicarbonate (3.18 g, 37.9 mmol, Eq: 1.2) was added followed by potassium iodide (1.06 g, 6.34 mmol, Eq: 0.201). 2-chloroacetonitrile (2.92 g, 2.46 mL, 37.9 mmol, Eq: 1.2) was added, the suspension was heated up to 78° C. (oil bath 80° C.) and stirred overnight. The reaction mixture was cooled to RT, and water (22.5 g, 22.5 mL) was added. The organic phase was separated and washed with half saturated aqueous NaHCO$_3$ (22.5 mL), a 10% aqueous sodiumthiosulfate solution (22.5 mL) and water (22.5 g, 22.5 mL). The organic phase was concentrated under reduced pressure (45° C./180 mbar, circa 50 mL) to circa half the volume. The crude product solution was solvent exchanged to 2-propanol (final volume circa 30 mL). The 2-propanol-solution was seeded and stirred for 1 h at RT, then the white suspension was cooled to 0°-2° C., stirred for another hour and filtered over a glass sintered funnel. The crystals were washed with cold 2-propanol (7.84 g, 10 mL) and dried until constant weight (5 mbar/50° C.) to give 8.8 g of the title compound as a white crystalline powder.

2-Propanol (312 g, 400 mL) was charged in the reactor at 20-25° C. Acetyl chloride (AcCl) (255 g, 231 mL, 3.22 mol, Eq: 9.97) was added dropwise over 45 min. After 15 min a warm (45-55° C.) solution of tert-butyl N-[4-chloro-2-[[cyanomethyl(methyl)amino]methyl]phenyl]carbamate in 2-propanol (468 g, 600 mL) was added over 45-60 min keeping the temperature between 20-40° C. during which most of the Boc-deprotection happens and the cyclization step started. After 2 h at 40° C., AcCl (127 g, 115 mL, 1.6 mol, Eq: 4.97) was added dropwise at 35-40° C. After 4 h at 40° C., AcCl (127 g, 115 mL, 1.6 mol, Eq: 4.97) was added at 35-40° C. The suspension was stirred overnight at 40° C. The reaction mixture was concentrated at Tj=60° C., under reduced pressure to a volume of circa 400 mL. The suspension was solvent exchanged at constant volume with further 2-propanol (936 g, 1.2 l) and was stirred >1 h at RT. The suspension was filtered and the filter cake was washed with 2-propanol (195 g, 250 mL). The crystals were dried at 60° C./10 mbar to give 85.8 g of product as white crystals (99.2 a % purity by HPLC).

8-Chloro-5-methyl-1-[4-(2-pyridyloxy)cyclohexyl]-4,6-dihydro-[1,2,4]triazolo[4,3-a][1,4]benzodiazepine I, form A

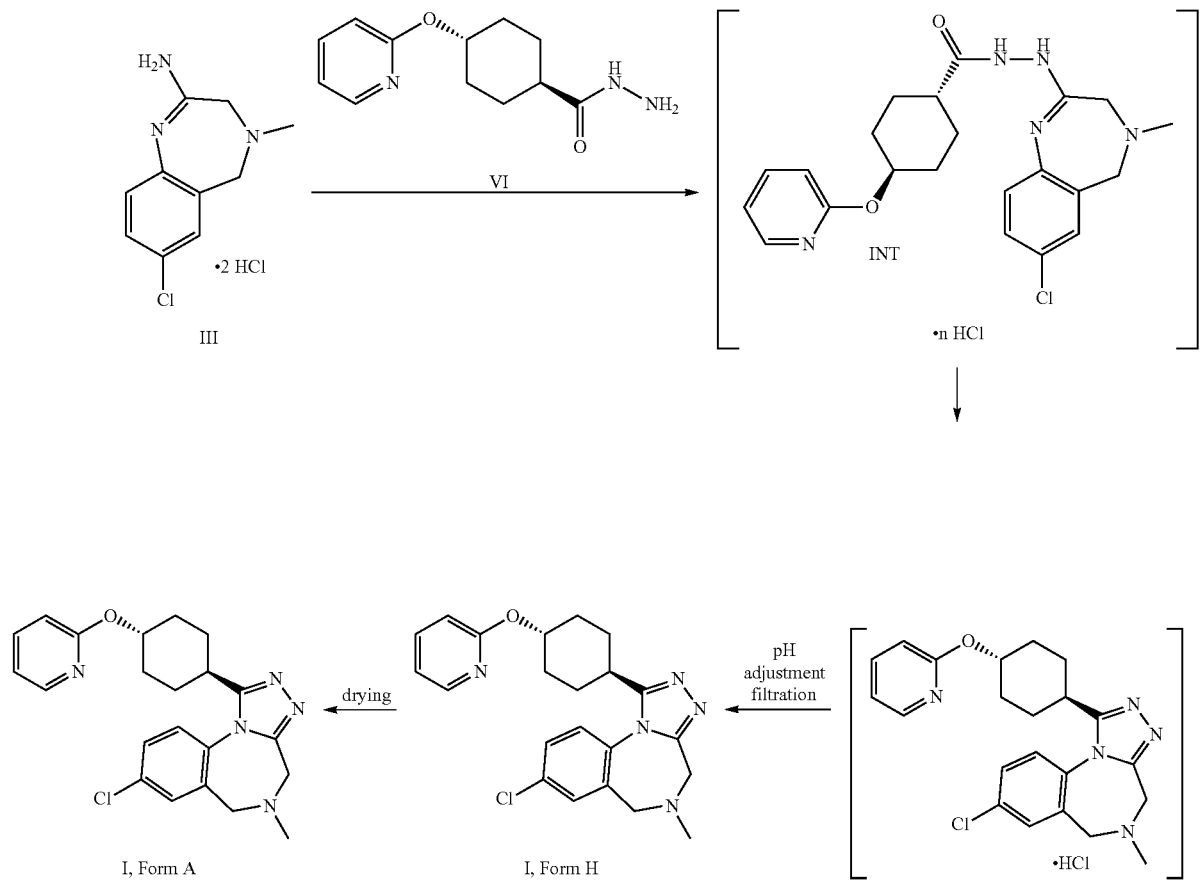

7-Chloro-4-methyl-3,5-dihydro-1,4-benzodiazepin-2-amine dihydrochloride (92.3 g, 326 mmol, Eq: 1.00) and 4-(2-pyridyloxy)cyclohexanecarbohydrazide (76.8 g, 326 mmol, Eq: 1.00) were charged in the reactor followed by 2-propanol (504 g, 646 mL). The suspension was heated at reflux for 18 h at 80-83° C. (until complete conversion of the amidine and the intermediate). The reaction mixture was cooled down to RT while water (775 g, 775 mL) was added. The almost clear solution was filtered. The filter was washed with water (24.9 g, 24.9 mL) to give 1.5 L of crude product solution (pH 4).

The filtrate (1.5 L) was split in 2 portions: 1 L into reactor B (217 mmol theory) and 0.5 L into reactor A (109 mmol theory).

Compound I is best isolated as free base. However, its hydrochloride can also be isolated: after complete conversion of the amidine and the intermediate, the reaction mixture is cooled to 0-5° C. The resulting suspension is stirred for 1 h at 0-5° C. and filtered. The filter cake is washed with cold isopropanol and dried under reduced pressure 50° C./10 mbar to give I.HCl.

Reactor a, pH 9-10 Crystallization.—1.7 Equiv NaOH
8% Aqueous NaOH (Ca. 95 g, corresponds to circa 1.7 equiv.) was added over 15 min, maintaining the temperature between 20–25° C. (spontaneous cryst. at 79 g addition, pH 10 at end of addition). Seed crystals of I, form A (75 mg) were added (in case the crystallization is not spontaneous). The light yellow suspension was stirred for 1.5 h at RT and was cooled to 0-5° C. within 30 min. After 5 h stirring at 0-5° C., the suspension was filtered. The filter cake (form H) was washed with cold (0-5° C.) 2-propanol/water 1:2 (123 mL), and water (42.0 g, 42 mL), and dried at 60° C. under reduced pressure to give 38.4 g of the title compound as a white crystalline powder (crystalline form A by powder X-Ray analysis, 99.3 a % purity by HPLC, 0.4 a % compound of formula VI').

Reactor B. pH≥12 Crystallization:
The pH was set to ≥12 by addition of 222 g of a circa 8% aqueous NaOH (circa 2 equiv.) over 30 min maintaining the temperature between 20-25° C. (pH 10-11 after 201 g added, spontaneous cryst. after addition of 130 g). Seed crystals of I, form A (75 mg) were added (in case the crystallization is not spontaneous). The yellow suspension was stirred for 2 h at RT then cooled to 0-5° C. for 30 min. After 5 h stirring at 0-5° C., the suspension was filtered. The filter cake (form H) was washed with cold (0-5° C.) 2-propanol/water 1:2 (246 mL), and water (83.0 g, 83 mL), and dried at 60° C. under reduced pressure to give 74.6 g of the title compound as white crystalline powder (99.7a % purity by HPLC, compound of formula VI' was not detected, form A by powder X-Ray analysis).

8-chloro-5-methyl-[4-methyl-(2-pyridyloxy)cyclohexyl]-4,6-dihydro-[1,2,4]triazolo[4,3-a][1,4]benzodiazepine I, form F

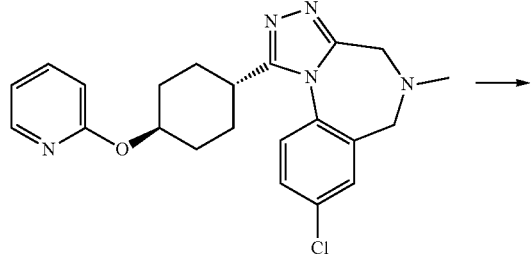

I, Form A

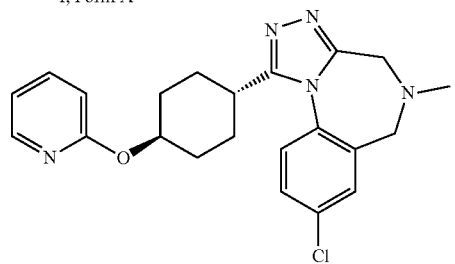

I, Form F

8-Chloro-5-methyl-1-[4-(2-pyridyloxy)cyclohexyl]-4,6-dihydro-[1,2,4]triazolo[4,3-a][1,4]benzodiazepine (38.1 g, 92.8 mmol, Eq: 1.00) was suspended in methyl acetate (698 g, 750 mL), the suspension was heated to 55° C. The resulting turbid solution was filtered and cooled to 43-45° C. within 30 min. The solution was seeded with 0.75 g of compound with formula I, form F and cooled over 2 h to RT. The suspension was stirred overnight and circa 550 mL methyl acetate (MeOAc) was exchanged at constant volume (Tj max 45° C./400-450 mbar) with n-heptane (374 g, 550 mL) targeting circa 45-55% m/m MeOAc content. The suspension was cooled to 0° C. and stirred at 0° C. for >4 h. The suspension was filtered. The filter cake was washed with n-heptane (102 g, 150 mL) and dried at 60° C. under reduced pressure to give 36 g of the title compound as crystalline form F (by powder X-ray analysis).

8-Chloro-5-methyl-1-[4-(2-pyridyloxy)cyclohexyl]-4,6-dihydro-[1,2,4]triazolo[4,3-a][1,4]benzodiazepine I, form F 8-Chloro-5-methyl-1-[4-(2-pyridyloxy)cyclohexyl]-4,6-dihydro-[1,2,4]triazolo[4,3-a][1,4]benzodiazepine (13.6 g) was dissolved in 2-propanol (213 g, 272 mL) at 55° C. The hot solution was filtered. The solution was concentrated to circa 130-140 mL. n-Heptane (93.0 g, 136 mL) was added at 55° C. for 15 min. The clear solution was cooled to circa 45° C. and was seeded with 300 mg of crystalline I, form F. The mixture was cooled within 20 h to 0° C. The resulting suspension was filtered. The filter cake was washed with cold (0° C.) 2-propanol/n-heptane 1:1 (54.4 mL) and dried to give 11.7 g of the title compound as crystalline form F (by powder X-ray analysis).

Trans-4-(2-pyridyloxy)cyclohexanecarboxylic acid XXIII

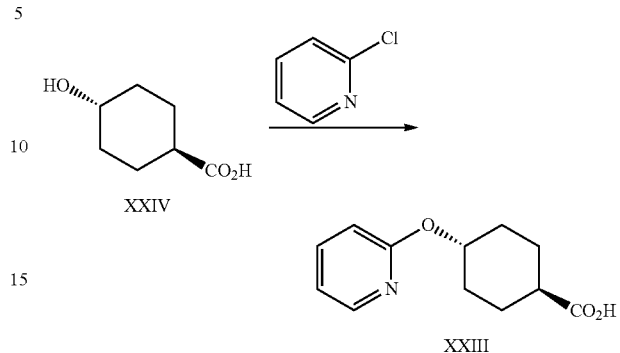

Sodium tert-amyloxide (tAmONa) (444 g, 3.83 mol, Eq: 2.26) was charged in the reactor followed by N-methyl-2-pyrrolidone (NMP) (2.06 kg, 2 L) and heated at Tj=90° C. A solution of trans-4-hydroxycyclohexanecarboxylic acid (244 g, 1.69 mol, Eq: 1.00) in NMP (515 g, 500 mL) was added over 15 min at 80-85° C. 2-Chloropyridine (239 g, 2.11 mol, Eq: 1.24) was added over 5 min at 80-85° C. After >60 h, the reaction mixture was cooled to 50° C. and water (8.00 kg, 8 L) at 50° C. The reaction mixture was cooled to RT. The pH was adjusted to circa 5 with 25% aqueous HCl (280 g, 250 mL). The suspension was cooled to 0-5° C., stirred for >2 h and was filtered. The filter cake was washed with water (8.00 kg, 8 L) and was dried at 50° C. under reduced pressure to give 245 g of the title compound (>99 a % purity by gas chromatography (GC)).

Trans-4-(2-pyridyloxy)cyclohexanecarbohydrazide VI

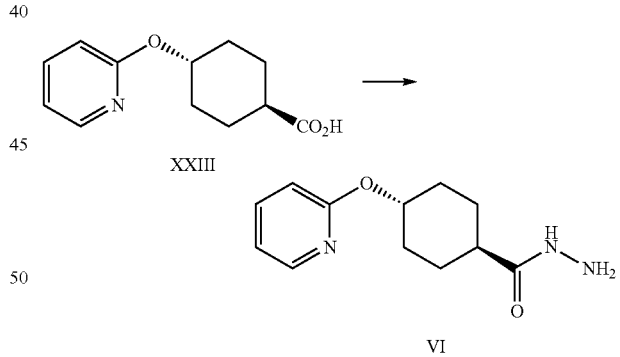

1,1'-Carbonyldiimidazole (CDI) (215 g, 1.32 mol, Eq: 1.21) was suspended in THF (1.07 kg, 1.2 L) at 20° C. A solution of trans-4-(2-pyridyloxy)cyclohexanecarboxylic acid (243 g, 1.1 mol, Eq: 1.00) in THF (1.07 kg, 1.2 L, Eq: -) was added over 70 min. After 16 h, the reaction mixture was degassed (vacuum/N2 cycles). About 100 mL of solvent were distilled off under reduced pressure at Tr<30° C. The resulting activated acid solution was added at 15-25° C. to a solution of hydrazine monohydrate (75.2 g, 73 mL, 1.5 mol, Eq: 1.4) in THF (1.07 kg, 1.3 L)/water (1.2 kg, 1.3 L). After >2 h stirring at 20-25° C., 3.2 L of solvent were distilled at Tj 50-55° C./300-200 mbar while continuously adding 3.5 L of water. The resulting suspension was stirred overnight at RT and filtered. The filter cake was washed with water (750 g, 0.75 L) and dried at 50° C. under reduced pressure to give 223 g of the title compound (98.9 a % by HPLC, 0.4% of compound of formula VI').

1-(5-Chloro-2-nitro-phenyl)-N-methyl-methanimine XIV

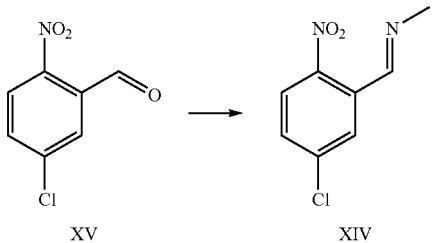

5-Chloro-2-nitrobenzaldehyde (45 g, 243 mmol, Eq: 1.00) was treated with 2 M methylamine in MeOH (141 g, 180 mL, 360 mmol, Eq: 1.48). The reaction mixture was stirred at RT for 5 h and concentrated under reduced pressure to give 48.06 g of the title compound. The crude product is introduced directly in the next step without further purification.

1-(5-Chloro-2-nitro-phenyl)-N-methyl-methanamine XIII

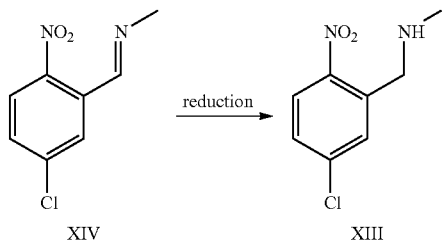

(E)-N-(5-Chloro-2-nitrobenzylidene)methanimine (47.5 g, 239 mmol, Eq: 1.00) was dissolved in methanol (447 g, 565 mL). The solution was cooled to 0° C. and sodium borohydride (7.64 g, 194 mmol, Eq: 0.811) was added in portions over 25 min. The reaction mixture was stirred overnight at RT (circa 98% conversion). Further sodium borohydride (1.77 g, 44.9 mmol, Eq: 0.19) was added and the reaction mixture was stirred for 3 h. The solvent exchanged to dichloromethane (DCM) (final volume circa 400 mL) and washed with saturated aqueous NaHCO₃ (200 mL). The aqueous phase was separated and extracted twice with DCM (318 g, 240 mL). The organic phases were washed sequentially twice with half saturated aqueous NaHCO₃ (200 mL). The organic phases were combined, dried over magnesium sulfate (MgSO₄) and concentrated under reduced pressure to give 47.1 g of the title compound.

4-Chloro-2-(methylaminomethyl)aniline XII

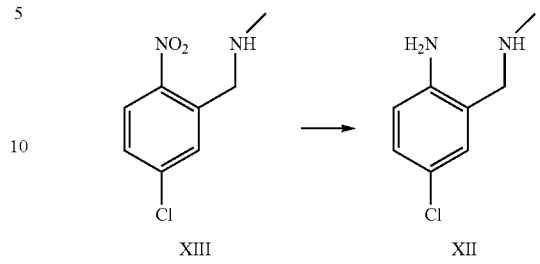

1-(5-Chloro-2-nitro-phenyl)-N-methyl-methanamine (23 g, 109 mmol, Eq.: 1) was dissolved in methanol (690 mL), 46% Raney-Nickel (6.91 g, 55 mmol, 0.5 equiv.) was added and the mixture was stirred under a hydrogen atmosphere (1 bar) at RT. After completion of the reaction, the suspension was filtered and the filtrate was concentrated under reduced pressure to give 19 g of the crude title compound.

1-(5-Chloro-2-nitro-phenyl)-N-methyl-methanamine hydrochloride XIII.HCl

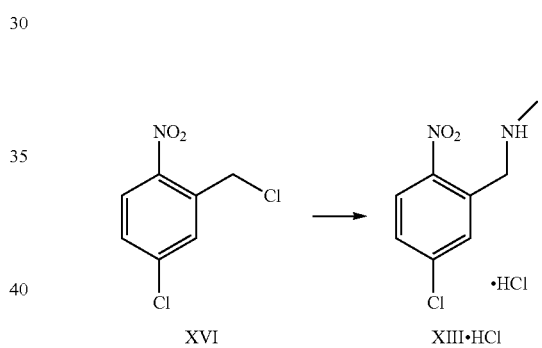

40% Methylamine in methanol (90.0 mL, 882 mmol, Eq: 12.1) was charged in the reactor and a solution of 4-chloro-2-(chloromethyl)-1-nitrobenzene (15 g, 72.8 mmol, Eq: 1.00) in MeOH (94.8 g, 120 mL) was added dropwise over 50 min at RT The light yellow solution was stirred at RT for 5.5 h (until completion of the reaction). The reaction mixture was concentrated under reduced pressure to give 21.5 g of a yellow solid which was taken up in AcOEt (108 g, 120 mL). The resulting suspension was filtered. The filter cake (methylamine hydrochloride) was washed three times with AcOEt (135 g, 150 mL). The filtrate was evaporated to afford 14.6 g of a yellow oil. The crude 1-(5-chloro-2-nitrophenyl)-N-methyl-methanamine was dissolved in AcOEt (108 g, 120 mL). 4.4 M Hydrogen chloride (HCl) in AcOEt (33.6 mL, 147 mmol, Eq: 2.02) was added slowly. The resulting pale yellow suspension was stirred overnight at RT. The suspension was filtered. The filter cake was washed twice with AcOEt and dried at 10 mbar, 50° C. to give 15.6 g of the title compound as a light yellow powder.

4-Chloro-2-(methylaminomethyl)aniline hydrochloride XII.HCl

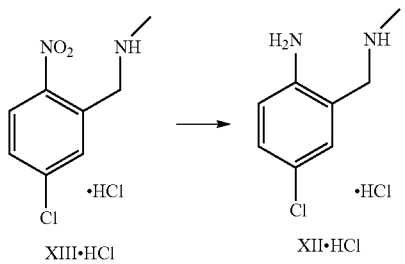

1-(5-Chloro-2-nitro-phenyl)-N-methyl-methanamine hydrochloride (50 g, 208 mmol, Eq.: 1) was dissolved in methanol (790 mL), 46% Raney-Nickel (13 g, 104 mmol, 0.5 equiv.) was added and the mixture was stirred under a hydrogen atmosphere (1 bar) at RT. After completion of the reaction, the suspension was filtered and the filtrate was concentrated under reduced pressure to give 43 g of the crude title compound.

The crude product can be crystallized:

The crude product (22.5 g) was dissolved in methanol (400 mL). Water (3.7 mL) and activated charcoal (2.5 g) were added. The suspension was heated to 50° C., then cooled to RT and filtered. The filtrate was concentrated under reduced pressure to circa half the volume. Isopropanol (200 mL) was added and the solution was concentrated under reduced pressure to circa 220 g during which crystallization started leading to a thick suspension. Isopropanol (50 mL) was added. The suspension was stirred 2 h at RT and was filtered. The filter cake was washed with isopropanol (30 mL) and was dried at 50° C./10 mbar to give 15 g of the title compound as an off-white powder.

2-[(2-Amino-5-chloro-phenyl)methyl-methyl-amino]acetonitrile XI

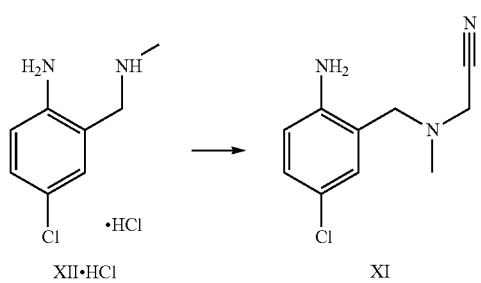

4-Chloro-2-((methylamino)methyl)aniline hydrochloride (10 g, 48.3 mmol, Eq: 1.00) was suspended in acetonitrile (78.0 g, 100 mL). Sodium hydrogen carbonate (8.92 g, 106 mmol, Eq: 2.2) was added and the suspension was heated to 85° C. 2-chloroacetonitrile (3.91 g, 3.28 mL, 50.7 mmol, Eq: 1.05) was added and the reaction mixture was stirred for 24 h. The reaction mixture was cooled to RT and water (150 g, 150 mL) was added. Toluene (173 g, 200 mL) was added and most of the acetonitrile was removed at the rotavapor. The aqueous phase was separated and extracted with toluene (86.7 g, 100 mL). The organic phases were washed with half saturated aqueous NaHCO₃ (100 mL) and half saturated aqueous NaCl. The organic phases were combined, dried over MgSO₄, filtered and concentrated under reduced pressure to give 9.95 g of the title compound as a light yellow solid. Alternatively, the alkylation can also be performed using the free base XII as starting material.

Trans-N'-(2-chloroacetyl)-4-(2-pyridyloxy)cyclohexanecarbohydrazide XXI

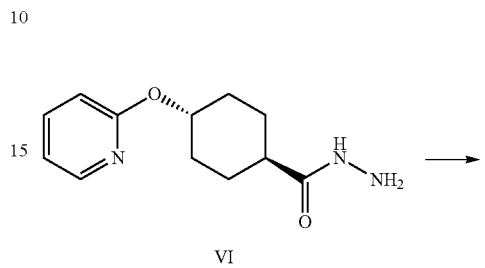

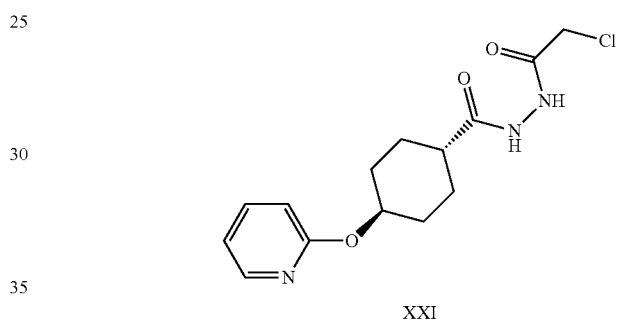

Trans-4-(2-pyridyloxy)cyclohexanecarbohydrazide (4 g, 17.0 mmol, Eq: 1.00) was suspended in DCM (66.2 g, 50.0 mL). 2,4,6-Trimethylpyridine (sym-collidine) (2.29 g 2.5 mL, 18.7 mmol, Eq: 1.1) was added. The suspension was cooled to 0° C. and 2-chloroacetyl chloride (2.04 g 1.43 mL, 17.9 mmol, Eq: 1.05) was added dropwise over 30 min at 0-5° C. After 1 h at 0-5° C., the suspension was filtered. The filter cake was washed with cold dichloromethane (40 mL) and dried under reduced pressure at 40° C. to give 5.1 g of the title compound.

Trans-2-(chloromethyl)-5-[4-(2-pyridyloxy)cyclohexyl]-1,3,4-oxadiazole XX

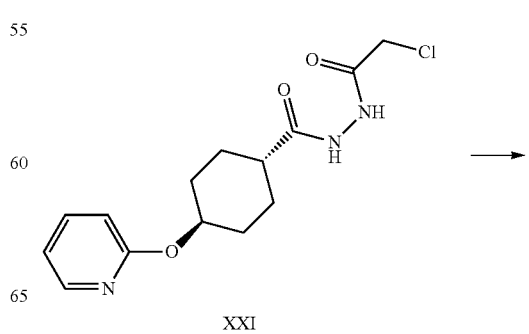

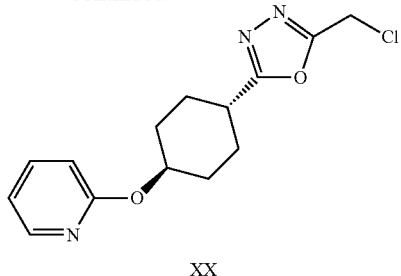

XX

N'-(2-Chloroacetyl)-4-(2-pyridyloxy)cyclohexanecarbohydrazide (44 g, 141 mmol, Eq: 1.00) was suspended in acetonitrile (257 g, 330 m, Eq: -). The suspension was cooled to 0° C. and triflic anhydride (48.8 g 28.7 mm, 169 mmol, Eq: 1.2) was added over 30 min. The reaction was stirred at RT until >95% conversion (>15 h). The resulting solution was cooled to 0° C. and a solution of sodium hydrogen carbonate (27.0 g, 322 mmol, Eq: 2.28) in water (440 g, 440 mL) was added followed by dichloromethane (437 g 330 mL). The aqueous phase was extracted twice with dichloromethane (662 g, 500 mL). The organic phases were washed sequentially with half saturated aqueous NaCl (500 mL). The organic phases were combined, dried over MgSO$_4$, filtered and concentrated under reduced pressure to give 44.0 g of the crude title compound.
Crystallization: The crude product (39.0 g) was crystallized from isopropanol to give 19.08 g of the title compound.

Trans-4-chloro-2-[[methyl-[[5-[4-(2-pyridyloxy)cyclohexyl]-1,3,4-oxadiazol-2-yl]methyl]amino]methyl]aniline XIX

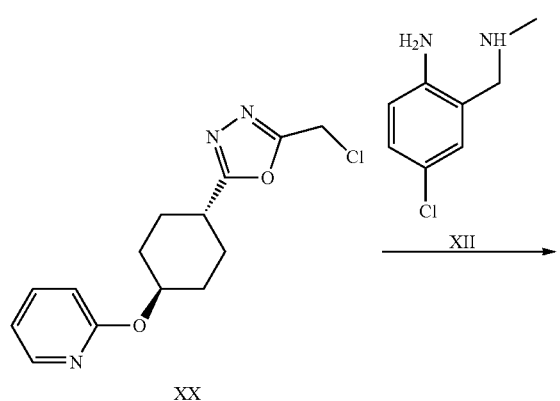

Trans-2-(chloromethyl)-5-[4-(2-pyridyloxy)cyclohexyl]-1,3,4-oxadiazole (6.7 g, 21.9 mmol, Eq: 1.00), 4-chloro-2-((methylamino)methyl)aniline (4.33 g, 24.1 mmol, Eq: 1.1), sodium hydrogen carbonate (2.21 g, 26.3 mmol, Eq: 1.2) and acetonitrile (54.8 g, 70.3 mL) were charged in the reactor and heated at reflux for 4 h. Additional 4-chloro-2-((methylamino)methyl)aniline (393 mg, 2.19 mmol, Eq: 0.1) was added and the reaction mixture was stirred for 20 h at reflux. The reaction mixture was cooled to RT. Water (20.0 g, 20.0 mL) and dichloromethane (79.5 g, 60.0 mL) were added. The aqueous phase was separated and extracted with dichloromethane (26.5 g, 20.0 mL). The organic phases were washed sequentially with saturated aqueous ammonium chloride (NH$_4$Cl) (25.0 mL), 10% aqueous NaCl (25.0 mL) and saturated aqueous NaCl (25.0 mL). The organic phases were combined, dried over MgSO$_4$ and filtered. The filtrate was filtered over 25 g of silica gel (SiO$_2$) and concentrated under reduced pressure to give 5.3 g of the title compound.

Trans-8-chloro-5-methyl-1-[4-(2-pyridyloxy)cyclohexyl]-4,6-dihydro-[1,2,4]triazolo[4,3-a][1,4]benzodiazepine I

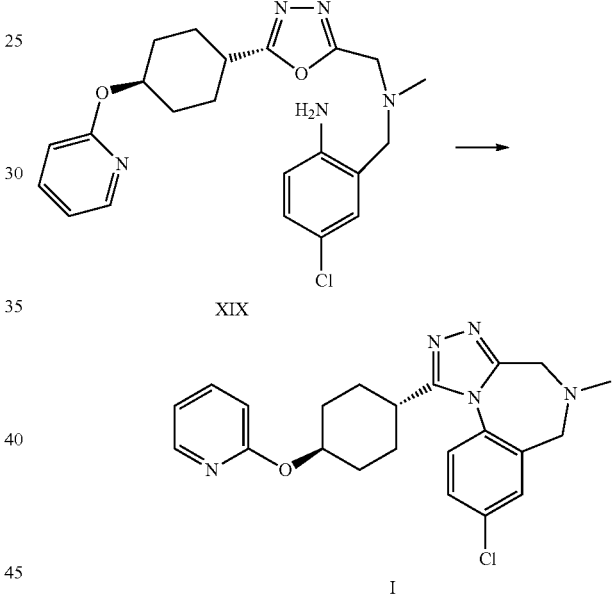

Trans-4-chloro-2-[[methyl-[[5-[4-(2-pyridyloxy)cyclohexyl]-1,3,4-oxadiazol-2-yl]methyl]amino]methyl]aniline (5 g, 10.1 mmol, Eq: 1.00) was dissolved in tetrahydrofuran (44.4 g, 50 mL). Trifluoroacetic acid (2.02 g, 1.36 mL, 17.4 mmol, Eq: 1.72) was added and the reaction mixture was heated to 60° C. for 2.5 h. The reaction was cooled to RT, saturated aqueous NaHCO$_3$ (25 mL) was added (pH=8) and the mixture was stirred for 15 min (formation of a yellow suspension). Water (25.0 g, 25 mL) and AcOEt (36.1 g, 40 mL) were added. After 30 min stirring, the aqueous phase was separated and extracted with AcOEt (18.0 g, 20 mL). The organic phases were washed twice with saturated aqueous NaCl (17 mL) (pH~7). The organic phases were combined, dried over MgSO$_4$, filtered and concentrated under reduced pressure to give 5.03 g of the crude title compound. The crude product was taken up in isopropanol (20 mL) and evaporated, redissolved again in isopropanol (20 mL) and evaporated. The residue was dissolved in isopropanol (11.8 g, 15 mL) and seeded with I, form F. The crystallization started and the suspension was stirred for 18 h at RT. The suspension was filtered. The filter cake was washed twice with isopropanol (7.84 g, 10 mL) and dried under reduced pressure to give 3.11 g of the title compound (form F by X-Ray powder diffraction).

4-Chloro-2-(methylaminomethyl)aniline dihydrochloride XII.2HCl

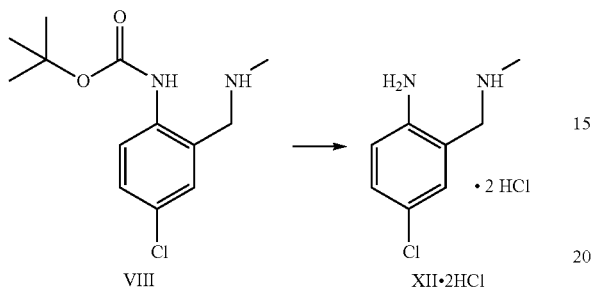

tert-Butyl 4-chloro-2-((methylamino)methyl)phenylcarbamate (1.0 g, 3.69 mmol, Eq: 1.00) was dissolved in AcOEt (4.5 g, 5.00 mL). 4 M HCl in AcOEt (4.62 mL, 18.5 mmol, Eq: 5.00) was added. The resulting suspension was heated overnight at 40° C. The suspension was cooled to RT, stirred for 1 h and filtered. The filter cake was washed with AcOEt (20 mL) and was dried under reduced pressure at 50° C. to give 0.9 g of the title compound.

2-[(2-Amino-5-chloro-phenyl)methyl-methyl-amino]acetonitrile

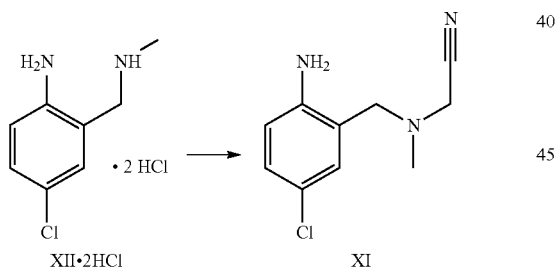

4-Chloro-2-((methylamino)methyl)aniline dihydrochloride from previous step (0.8 g, 3.28 mmol, Eq: 1.00) was suspended in acetonitrile (6.24 g, 8.00 mL). Sodium hydrogen carbonate (883 mg, 10.5 mmol, Eq: 3.2) was added. The white suspension was heated to 85° C. 2-chloroacetonitrile (266 mg, 223 µl, 3.45 mmol, Eq: 1.05) was added and stirred overnight at 85° C. The reaction mixture was cooled to RT, water (12.0 g, 12.0 mL) was added and the mixture was stirred for 10 min. Toluene (13.9 g, 16.0 mL) was added and most of the acetonitrile was removed under reduced pressure. The aqueous phase was separated and extracted with toluene (6.94 g, 8.00 mL). The organic phases were washed with half saturated aqueous NaHCO₃ (8.00 mL) and half saturated NaCl (8.00 mL), dried over MgSO₄, filtered and concentrated under reduced pressure to give 840 mg of the title compound. The crude product was dissolved in MTBE (5 mL) at reflux. The colorless solution was slowly cooled to RT. The resulting white suspension was filtered. The filter cake was washed with n-heptane (20 mL) and dried under reduced pressure to give 410 mg of the title compound as a white powder.

4-Chloro-2-(methylaminomethyl)aniline XII

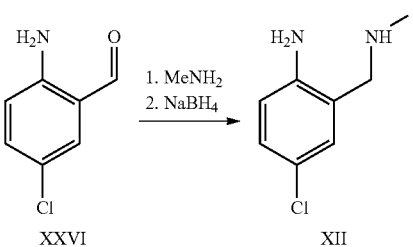

2-Amino-5-chlorobenzaldehyde (500 mg, 3.12 mmol, Eq: 1.00) was dissolved at RT in ethanol (5.93 g, 7.50 mL). 41% Aqueous methylamine solution (472 mg, 527 µl, 6.23 mmol, Eq: 2.00) was added and the yellow solution was stirred for 1 h at RT. NaBH₄ (118 mg, 3.12 mmol, Eq: 1.00) was added and the suspension was stirred for 18 h at RT. Ethylacetate (18.0 g, 20 mL) and half saturated aqueous NaCl (20 mL) were added. The organic phase was separated, dried over MgSO₄, filtered and was evaporated to dryness to give 550 mg of the title compound.

7-Chloro-4-methyl-3,5-dihydro-1,4-benzodiazepin-2-amine II

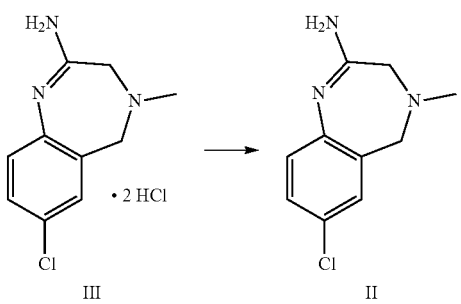

7-Chloro-4-methyl-4,5-dihydro-1H-benzo[e][1,4]diazepin-2(3H)-imine dihydrochloride (1.75 g, 6.19 mmol, Eq: 1.00) was suspended in AcOEt (50 mL). Saturated aqueous sodium hydrogen carbonate (30 mL) was added and the mixture was stirred for 30 min at RT. The aqueous phase was separated and extracted twice with AcOEt (20 mL). The organic phases were combined, dried over MgSO₄, filtered and concentrated under reduced pressure to give 930 mg of the title compound.

7-Chloro-4-methyl-3,5-dihydro-1,4-benzodiazepin-2-amine dihydrochloride III

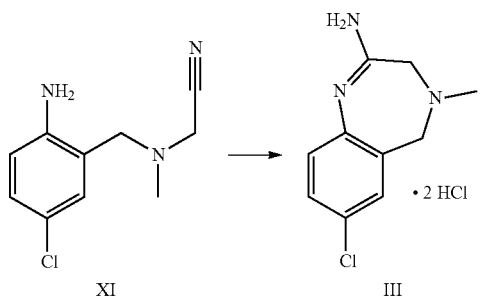

2-((2-Amino-5-chlorobenzyl)(methyl)amino)acetonitrile (11.1 g, 51.4 mmol, Eq: 1.00) was dissolved with trifluoroethanol (138 g, 100 mL). 4M HCl in dioxane (38.5 mL, 154 mmol, Eq: 3.0) was added. The reaction mixture was stirred 6 h at 40° C. until completion then concentrated under reduced pressure to give 17.95 g of the title compound (contains ca 9% dioxane and 11% residual trifluoroethanol).

Alternatively, compound of formula XI can be reacted to compound of formula III under conditions similar to the one used for the direct transformation of compound of formula VII to compound of formula III as described in a previous example.

tert-Butyl N-[4-chloro-2-(methylaminomethyl)phenyl]carbamate acetic acid salt VIII.AcOH

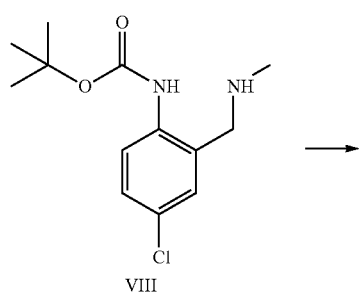

tert-Butyl 4-chloro-2-((methylamino)methyl)phenylcarbamate (1.0 g, 3.1 mmol, Eq: 1.00) was dissolved in MTBE (8.21 g, 12 mL) at RT. Acetic acid (206 mg, 196 µl, 3.41 mmol, Eq: 1.1) was added dropwise during which the product started to crystallize. After 2 h at RT, the suspension was filtered. The filter cake was washed with MTBE and dried under reduced pressure (10 mbar/50° C.) to give 0.58 g of the title compound.

The invention claimed is:

1. A process to synthesize compound formula I, comprising reacting compound formula III with compound formula VI

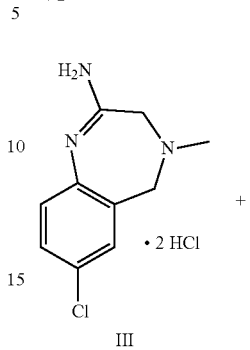

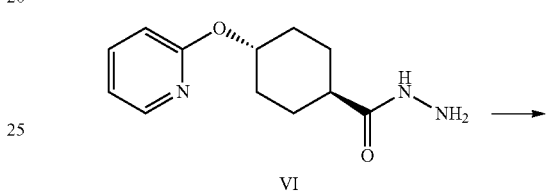

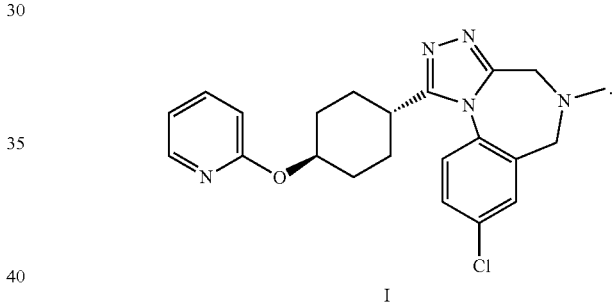

2. The process according to claim 1, further comprising reacting compound formula XI to form compound formula III:

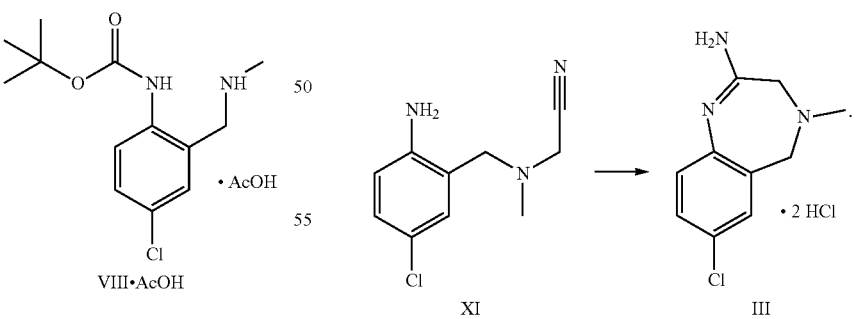

3. The process according to claim 2 further comprising reacting compound formula X to form compound of formula IX; reacting compound formula IX to form compound of formula VIII; reacting compound formula VIII to form compound of formula VII; and reacting compound formula VII to form compound of formula XI or a pharmaceutically acceptable salt thereof via the following series of steps:

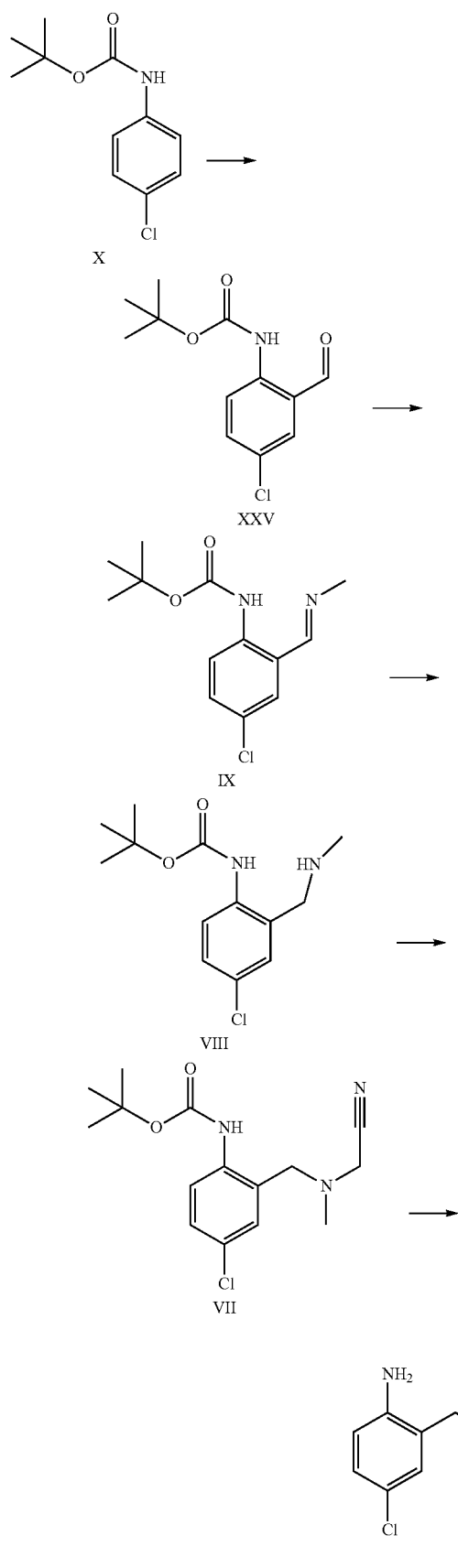

4. The process according to claim 2 further comprising reacting compound formula XV to form compound formula XIV; reacting compound formula XIV to form compound formula XIII; reacting compound formula XIII to form compound formula XII; and reacting compound formula XII to form compound formula XI or a pharmaceutically acceptable salt thereof via the following series of steps:

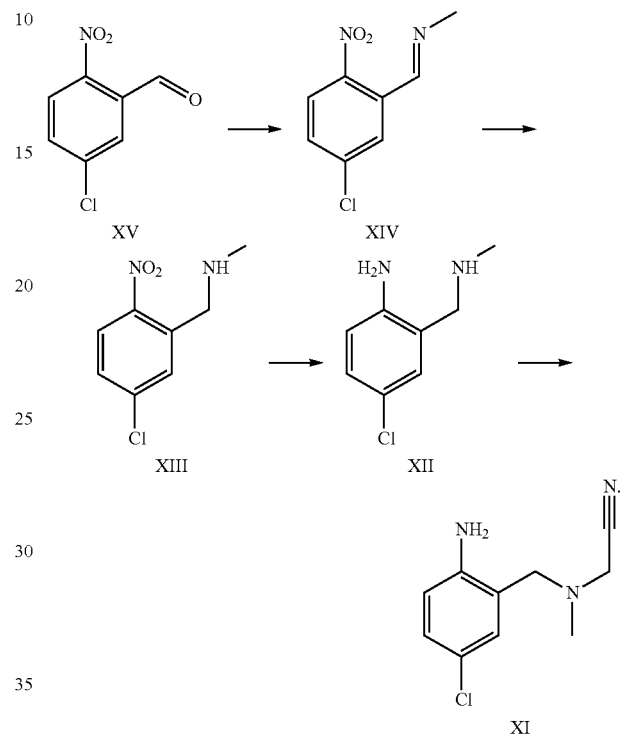

5. The process according to claim 2 further comprising reacting compound formula XXVI to form compound formula XII and reacting compound formula XII to form compound formula XI or a pharmaceutically acceptable salt thereof via the series of following steps

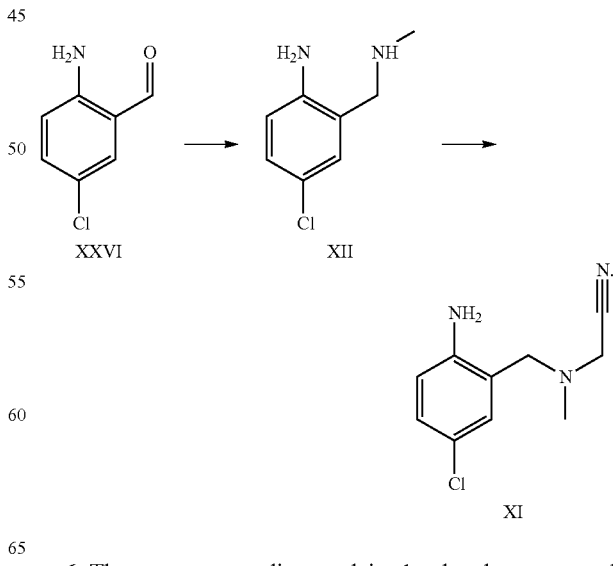

6. The process according to claim 1, whereby compound formula INT is formed as intermediate from the reaction of compound formula III and compound formula VI according to the following steps, and wherein compound formula INT is reacted to form compound formula I:
III
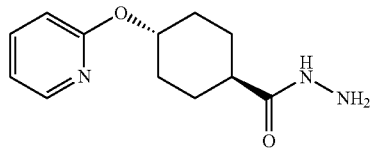
VI
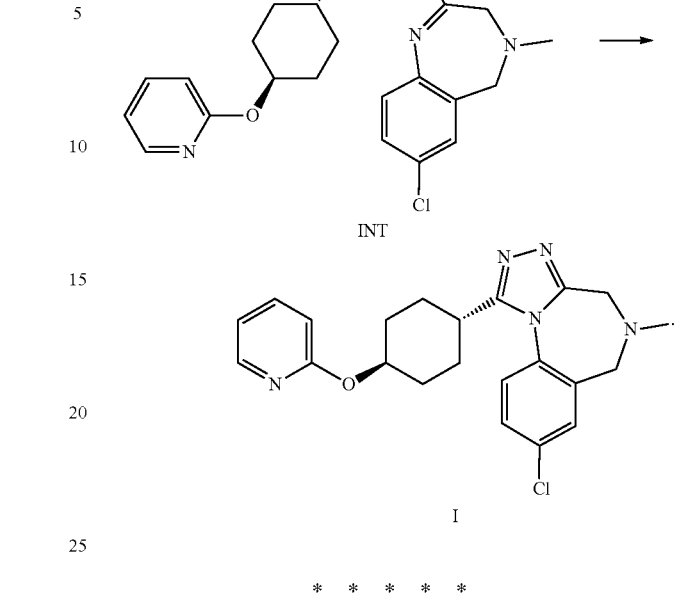
* * * * *